US007279491B2

(12) United States Patent
Apodaca et al.

(10) Patent No.: US 7,279,491 B2
(45) Date of Patent: Oct. 9, 2007

(54) PHENYLPIPERIDINES AND PHENYLPYRROLIDINES

(75) Inventors: Richard L. Apodaca, San Diego, CA (US); Curt A. Dvorak, San Diego, CA (US); Chandravadan R. Shah, San Diego, CA (US); Wei Xiao, San Diego, CA (US)

(73) Assignee: Janssen Pharmaceutica N.V. (BE)

( * ) Notice: Subject to any disclaimer, the term of this patent is extended or adjusted under 35 U.S.C. 154(b) by 259 days.

(21) Appl. No.: 10/692,080

(22) Filed: Oct. 23, 2003

(65) Prior Publication Data

US 2004/0087573 A1 May 6, 2004

Related U.S. Application Data

(60) Provisional application No. 60/420,494, filed on Oct. 23, 2002.

(51) Int. Cl.
*A61K 31/445* (2006.01)
*C07D 401/10* (2006.01)

(52) U.S. Cl. .................. 514/316; 514/231.5; 514/255; 514/318; 514/326; 540/467; 544/124; 544/360; 546/187; 546/194; 546/208

(58) Field of Classification Search ............. 514/231.5, 514/255, 316, 318, 326; 540/467; 544/124, 544/360; 546/187, 194, 208
See application file for complete search history.

(56) References Cited

U.S. PATENT DOCUMENTS

| 3,714,179 A | | 1/1973 | Tweit | |
|---|---|---|---|---|
| 3,886,160 A | | 5/1975 | Tweit | |
| 4,659,716 A | * | 4/1987 | Villani et al. | 514/290 |
| 5,030,644 A | | 7/1991 | Baldwin et al. | |
| 5,217,986 A | | 6/1993 | Pomponi et al. | |
| 5,352,707 A | | 10/1994 | Pompni et al. | |
| 5,869,479 A | | 2/1999 | Kreutner et al. | |
| 2005/0222408 A1 | * | 10/2005 | Lee et al. | 544/60 |

FOREIGN PATENT DOCUMENTS

| EP | 0 952 154 A2 | 10/1999 |
|---|---|---|
| EP | 0978512 A1 | 2/2000 |
| EP | 1 074 543 A1 | 2/2001 |
| JP | 02306237 A2 | 12/1990 |
| WO | WO99/42458 | 8/1999 |
| WO | WO 02/012190 A2 | 2/2002 |
| WO | WO 02/012214 A2 | 2/2002 |
| WO | WO 02/024695 A2 | 3/2002 |
| WO | WO 02/076925 A2 | 10/2002 |
| WO | WO 03/047520 A2 | 6/2003 |
| WO | WO 03/050099 A1 | 6/2003 |
| WO | WO 03/053912 A1 | 7/2003 |
| WO | WO 03/066604 A2 | 8/2003 |

OTHER PUBLICATIONS

Apodaca et al. Preparation of phenylpiperidines . . . CA 140:375080 (2004).*
PCT International Search Report, dated Mar. 29, 2004, for PCT Int'l Appln. No. PCT/US03/33809.
Albengres, E. et al. Systemic Antifungal Agents. Drug Safety (Feb. 1998) 18(2):83-97.
Ali, S.M. et al. Design, Synthesis, and Structure-Activity Relationships of Acetylene-Based Histamine H3 Receptor Antagonists. J. Med. Chem. (1999) 42(5):903-909.
Arrang, J.-M. et al. Auto-inhibition of Brain Histamine Release Mediated by a Novel Class (H3) of Histamine Receptor. Nature (Apr. 1983) 302:832-837.
Ash, A.S.F.; Schild, H.O. Receptors Mediating Some Actions of Histamine. Br. J. Pharmac. Chemother. (1966) 27:427-439.
Back, D.J.; Tjia, J.F. Inhibition of Tolbutamide Metabolism by Substituted Imidazole Drugs In Vivo: Evidence for a Structure-Activity Relationship. Br. J. Pharmacol. (1985) 85:121-126.
Barnes, J.C. et al. The Selective Histamine H3 Receptor Antagonist Thioperamide Improves Cognition and Enhances Hippocampal Acetylcholine Release In Vivo. Soc. Neurosci. Abstr. (1993) 19:1813.
Bioworld Today, Mar. 2, 1999, p. 3.
Black, J.W. et al. Definition and Antagonism of Histamine H2-Receptors. Nature (Apr. 1972) 236:385-390.
Ding, Y.-S. et al. Synthesis of High Specific Activity (+)- and (-)-6-[18F]Fluoronorepinephrine via the Nucleophilic Aromatic Substitution Reaction. J. Med. Chem. (1991) 34(2):767-771.
Ganellin, C.R. et al. Synthesis of Potent Non-Imidazole Histamine H3-Receptor Antagonists. Arch. Pharm. Pharm. Med. Chem. (Weinheim, Ger.) (1998) 331:395-404.
Garbarg, M. et al. S-[2-(4-Imidazolyl)ethyl]isothiourea, a Highly Specific and Potent Histamine H3 Receptor Agonist. J. Pharmacol. Exp. Ther. (1992) 263(1):304-310.
Gliatech Inc. Press Release Nov. 5, 1998.
Gonzalez, F. Garcia, et al. Synthesis of 3-aryl(alkyl)-4(D-arabino-tetrahydroxybutyl)imidazoline-2-thiones. Carbohydrate Research, 22(2), 436-40 (English) 1968.
Ichinose, M.; Barnes, P.J. Histamine H3-Receptors Modulate Nonadrenergic Noncholinergic Neural Bronchoconstriction in Guinea-Pig In Vivo. Eur. J. Pharmacol. (1989) 174(1):49-55.
Imamura, M. et al. Unmasking of Activated Histamine H3-Receptors in Myocardial Ischemia: Their Role as Regulators of Exocytotic Norepinephrine Release. J. Pharmacol. Exp. Ther. (1994) 271(3):1259-1266.
Jones, R.G. Studies on Imidazoles. II. The Synthesis of 5-Imidazolecarboylates from Glycine and Substituted Glycine Esters. J. Am. Chem. Soc. (1949) 71:644-647.

(Continued)

*Primary Examiner*—Celia Chang

(57) ABSTRACT

Substituted phenylpiperidines and phenylpyrrolidines of formula (I), compositions containing them, and methods of making and using them to treat histamine-mediated conditions.

22 Claims, No Drawings

OTHER PUBLICATIONS

Jordaan, A., Arndt, R.R., The Synthesis of 1-Methyl-5-(α-indolyl)imidazole and 1-Methyl-2-ethylthiol-5-(α-indolyl)imidazole. Journal of Heterocyclic Chemistry 5(5), 723-5 (English) 1968.

Kapetanovic, I.M.; Kupferberg, H.J. Nafimidone, an Imidazole Anticonvulsant, and Its Metabolite as Potent Inhibitors of Microsomal Metabolism of Phenytoin and Carbamazepine. Drug Metab. Dispos. (1984) 12(5):560-564.

Korte, A. et al. Characterization and Tissue Distribution of H3 Histamine Receptors in Guinea Pigs by N alpha-Methylhistamine. Biochem. Biophys. Res. Commun. (May 1990) 168(3):979-986.

Krause, M. et al. Medicinal Chemistry of Histamine H3 Receptor Agonists; In The Histamine H3 Receptor—A Target for New Drugs Leurs, R.; Timmerman, H. (Eds.) Elsevier (1998) 175-196.

Lavrijsen, K. et al. Induction Potential of Antifungals Containing an Imidazole or Triazole Moiety. Biochem. Pharmacol. (1986) 35(11):1867-1878.

Leurs, R. et al. The Medicinal Chemistry and Therapeutic Potentials of Ligands of the Histamine H3 Receptor. Prog. Drug Res. (1995) 45:107-165.

Leurs, R. et al; "Therapeutic potential of histamine H3 recepto agonists and antagonitsts" Trends n Pharmacological sciences, Elsevier Trends Journal, Cambridge, BG, vol. 19, No. 5, May 1, 1998; pp. 177-184, XP004121095.

Lin, J.-S. et al. Involvement of Histaminergic Neurons in Arousal Mechanisms Demonstrated with H3-Receptor Ligands in the Cat. Brain Res. (1990) 523:325-330.

Linney, I.D. et al. Design, Synthesis, and Structure-Activity Relationships of Novel Non-Imidazole Histamine H3 Receptor Antagonists. J. Med. Chem. (2000) 43(12):2362-2370.

Lovenberg, T.W. et al. Cloning and Functional Expression of the Human Histamine H3 Receptor. Mol. Pharmacol. (1999) 55:1101-1107.

Lovenberg, T.W. et al. Cloning of Rat Histamine H3 Receptor Reveals Distinct Species Pharmacological Profiles. J. Pharmacol. Exp. Ther. (2000) 293(3):771-778.

Machidori, H. et al. Zucker Obese Rats: Defect in Brain Histamine Control of Feeding. Brain Res. (1992) 590:180-186.

McLeod, R.L. et al. Antimigraine and Sedative Activity of SCH 50971: A Novel Orally-Active Histamine H3 Receptor Agonist. Soc. Neuroscl. Abstr. (1996) 22:2010.

Meier, G. et al. Piperidino-Hydrocarbon Compounds as Novel Non-Imidazole Histamine H3-Receptor Antagonists. Bioorg. Med. Chem. (2002) 10:2535-2542.

Monti, J.M. et al. Effects of Selective Activation or Blockade of the Histamine H3 Receptor on Sleep and Wakefulness. Eur. J. Pharmacol. (1991) 205(3):283-287.

Morisset, S. et al. High Constitutive Activity of Native H3 Receptors Regulates Histamine Neurons in Brain. Nature (Dec. 2000) 408:860-864.

Oda, T. et al. Molecular Cloning and Characterization of a Novel Type of Histamine Receptor Preferentially Expressed in Leukocytes. J. Biol. Chem. (2000) 275(47):36781-36786.

Panula, P. et al. Significant Changes in the Human Brain Histaminergic System in Alzheimer's Disease. Soc. Neurosci. Abstr. (1995) 21:1977.

Phelps, M.E. Positron Emission Tomography Provides Molecular Imaging of Biological Processes. Proc. Natl. Acad. Sci. (2000) 97(16):9226-9233.

Phillips, J.G.; Ali, S.M. Medicinal Chemistry of Histamine H3 Receptor Antagonists: In The Histamine H3 Receptor—A Target for New Drugs Leurs, R.; Timmerman, H. (Eds.) Elsevier (1998) 197-222.

Phillips, J.G. et al. Chapter 4, Recent Advances in Histamine $H_3$ Receptor Agents. Ann. Reports in Med. Chem., 31, 1998, pp. 31-40.

Rouleau, A. et al. Bioavailability, Antinociceptive and Antiinflammatory Properties of BP 2-94, a Histamine H3 Receptor Agonist Prodrug. J. Pharmacol. Exp. Ther. (1997) 281(3):1085-1094.

Sabbatini, Renato,M.E., The Cyclotron and PET, In Brain & Mind an electronic magazine about Neuroscience [online], Mar. 1997. Retrived from the internet, <http:www.epub.org.br/cm/n01/pet/petcyclo.htm.

Schlicker, E.; Marr, I. The Moderate Affinity of Clozapine at H3 Receptors is Not Shared by Its Two Major Metabolites and by Structurally Related and Unrelated Atypical Neuroleptics. Naunyn-Schmiedebergs's Arch. Pharmacol. (1996) 353:290-294.

Sheets, J.J.; Mason. J.I. Ketoconazole: a Potent Inhibitor of Cytochrome P-450-Dependent Drug Metabolism in Rat Liver. Drug Metab. Dispos. (1984) 12(5):603-606.

Stark, H. et al. Developments of Histamine H3-Receptor Antagonists. Drugs Future (1996) 21(5):507-520.

Tozer, M.J., et al.: "From Histamine to Imidazolylalkylsulfonamides: the design of a novel series of histamine H3 receptor antagonists"; Bioorganic & Medicinal CHemistry Letters, OXFORD, GB. vol. 9, No. 13, Jul. 5, 1999, pp. 1825-1830, XP004168846.

Tozer, M.J.; Kalindjian, S.B. Histamine H3 Receptor Antagonists. Exp. Opin. Ther. Patents (2000) 10(7):1045-1055.

Walczynski, K. et al. Non-Imidazole Histamine H3 Ligands, Part 2: New 2-Substituted Benzothiazoles as Histamine H3 Antagonists. Arch. Pharm. Pharm. Med. Chem. (Weinheim, Ger.) (1999) 332:389-398.

Walczynski, K. et al. Non-Imidazole Histamine H3 Ligands. Part I. Synthesis of 2-(1-Piperazinyl)- and 2-(Hexahydro-1H-1,4-diazepin-1-yl)benzothiazole Derivatives as H3-Antagonists with H1 Blocking Activities. Farmaco (1999) 54:684-694.

West, R.E. et al. Identification of Two H3-Histamine Receptor Subtypes. Mol. Pharmacol. (1990) 38(5):610-613.

West, R.E., Jr. et al. The Profiles of Human and Primate [3H]N alpha-methylhistamine Binding Differ from That of Rodents. Eur. J. Pharmacol. (1999) 377:233-239.

Yokoyama, H. et al. Effect of Thioperamide, a Histamine H3 Receptor Antagonists, on Electrically Induced Convulsions in Mice. Eur. J. Pharmacol. (1993) 234:129-133.

Anjaneyulu, B. et al. Synthesis of 14-C-Labelled 1-Methanesulphonyl-3-(1-methyl-5-nitro-1H-imidazol-2-yl)-2-imidazolidinone, (Go 10213). J. Labelled Compd. Radiopharm. (1983) 20(8):951-961.

Iemura, R. et al. Synthesis of Benzimidazole Derivatives as Potential H1-Antihistaminic Agents. J. Heterocycl. Chem. (1987) 24:31-37.

Iwata, R. et al. Synthesis of 3-[1H-Imidazol-4-yl]propyl 4-[18F]fluorobenzyl Ether ([18F]Fluoroproxyfan): A Potential Radioligand for Imaging Histamine H3 Receptors. J. Labelled Compd. Radiopharm. (2000) 43:873-882.

Jarosinski, M.A.; Anderson, W.K. Preparation of Noncondensed 2-Substituted 1-Methylimidazoles via Ipso Substitution Reaction on 2-Sulfinyl or 2-Sulfonyl Derivatives of 4.5-Disubstituted 1-Methylimidazoles. J. Org. Chem. (1991) 56(12):4058-4062.

Ohta, S. et al. Synthesis and Application of Imidazole Derivatives. Introduction of Carbogenic Substituents into the 5-Position of 1-Methyl-1H-imidazole. Chem. Pharm. Bull. (1992) 40(10):2681-2685.

Phillips, B.T. et al. Preparation of 5-Substituted 2-Mercapto-1-methylimidazoles. Direct Metalation of 2-Mercapto-1-methylimidazoles. Synthesis (1990) :761-763.

Schnettler, R.A. et al. 4-Aroyl-1,3-dihydro-2Himidazol-2-ones, a New Class of Cardiotonic Agents. J. Med. Chem. (1982) 25:1477-1481.

Shapiro, G.; Marzi, M. Synthesis of 2,5-Dilithio-1-methylimidazole. Terahedron Lett. (1993) 34(21):3401-3404.

Apodaca, R. et al. A New Class of Diamine-based Histamine H3 Receptor Antagonists: 4-(Aminoalkoxy)benzylamines. J. Med. Chem. (2003) 46(18):3938-3944.

Stark, H. Recent Advances in Histamine H3/H4 Receptor Ligands. Expert Opin. Ther. Patents (2003) 13(6):851-865.

Phenylalkynes to Treat Histamine-Mediated Conditions. Expert Opin. Ther. Patents (2003) 13(11):1759-1762.

Kiec-Kononowicz, K. et al. Importance of the Lipophilic Group in Carbamates Having Histamine H3-Receptor Antagonists Activity. Phamazie (2000) 55(5):349-355.

Mor, M. et al. Synthesis and Biological Assays of New H3-Antagonists with Imidazole and Imidazoline Polar Groups. II Farmaco (2000) 55:27-34.

Windshorst, A.D. et al. Characterization of the Binding Site of the Histamine H3 Receptor. 2. Synthesis, in vitro Phamacology and QSAR of a Series of Monosubstituted Benzyl Analogues of Thioperamide. J. Med. Chem. (2000) 43(9):1754-1761.

* cited by examiner

PHENYLPIPERIDINES AND PHENYLPYRROLIDINES

CROSS-REFERENCE TO RELATED APPLICATIONS

Provisional Application No. 60/420,494, filed Oct. 23, 1902, hereby incorporated by reference.

STATEMENT REGARDING FEDERALLY SPONSORED RESEARCH OR DEVELOPMENT

The research and development of the invention described below was not federally sponsored.

FIELD OF THE INVENTION

The present invention relates to phenylpiperidines and phenylpyrrolidines, their synthesis and their use, for example, for the treatment of disorders and conditions mediated by the histamine receptor.

BACKGROUND OF THE INVENTION

Histamine {2-(imidazol-4-yl)ethylamine} is a transmitter substance. Histamine exerts a physiological effect via multiple distinct G-protein coupled receptors. It plays a role in immediate hypersensitivity reactions and is released from mast cells following antigen IgE antibody interaction. The actions of released histamine on the vasculature and smooth muscle system account for the symptoms of the allergic response. These actions occur at the $H_1$ receptor (Ash, A. S. F. and Schild, H. O., Br. J. Pharmac. Chemother. 1966, 27:427-439) and are blocked by the classical antihistamines (e.g. diphenhydramine). Histamine is also an important regulator of gastric acid secretion through its action on parietal cells. These effects of histamine are mediated via the $H_2$ receptor (Black, J. W. et al., Nature 1972, 236:385-390) and are blocked by $H_2$ receptor antagonists (e.g. cimetidine). The third histamine receptor —$H_3$— was first described as a presynaptic autoreceptor in the central nervous system (CNS) (Arrang, J.-M. et al., Nature 1983, 302:832-837) controlling the synthesis and release of histamine. Recent evidence has emerged showing that the $H_3$ receptors are also located presynaptically as heteroreceptors on serotonergic, noradrenergic, dopaminergic, cholinergic, and GABAergic (gamma-aminobutyric acid containing) neurons. These $H_3$ receptors have also recently been identified in peripheral tissues such as vascular smooth muscle. Consequently there are many potential therapeutic applications for histamine $H_3$ agonists, antagonists, and inverse agonists. (See: "The Histamine $H_3$ Receptor—A Target for New Drugs", Leurs, R., and Timmerman, H., (Eds.), Elsevier, 1998; Morisset, S. et al., Nature 2000, 408:860-864.) A fourth histamine receptor —$H_4$— was recently described by Oda, T. et al. (J. Biol. Chem. 2000, 275(47):36781-36786).

The potential use of histamine $H_3$ agonists in sleep/wake and arousal/vigilance disorders is suggested based on animal studies (Lin, J.-S. et al., Brain Res. 1990, 523:325-330; Monti, J. M. et al., Eur. J. Pharmacol. 1991, 205:283-287). Their use in the treatment of migraine has also been suggested (McLeod, R. L. et al., Soc. Neurosci. Abstr. 1996, 22:2010) based on their ability to inhibit neurogenic inflammation. Other applications could be a protective role in myocardial ischemia and hypertension where blockade of norepinephrine release is beneficial (Imamura, M. et al., J. Pharmacol. Exp. Ther. 1994, 271(3):1259-1266). It has been suggested that histamine $H_3$ agonists may be beneficial in asthma due to their ability to reduce non-adrenergic non-cholinergic (NANC) neurotransmission in airways and to reduce microvascular leakage (Ichinose, M. and Barnes, P. J., Eur. J. Pharmacol. 1989, 174:49-55).

Several indications for histamine $H_3$ antagonists and inverse agonists have similarly been proposed based on animal pharmacology experiments with known histamine $H_3$ antagonists (e.g. thioperamide). These include dementia, Alzheimer's disease (Panula, P. et al., Soc. Neurosci. Abstr. 1995, 21:1977), epilepsy (Yokoyama, H. et al., Eur. J. Pharmacol. 1993, 234:129-133) narcolepsy, eating disorders (Machidori, H. et al., Brain Res. 1992, 590:180-186), motion sickness, vertigo, attention deficit hyperactivity disorders (ADHD), learning and memory (Barnes, J. C. et al., Soc. Neurosci. Abstr. 1993, 19:1813), and schizophrenia (Schlicker, E. and Marr, I., Naunyn-Schmiedeberg's Arch. Pharmacol. 1996, 353:290-294). (Also see: Stark, H. et al., Drugs Future 1996, 21(5):507-520; and Leurs, R. et al., Prog. Drug Res. 1995, 45:107-165 and references cited therein.) Histamine $H_3$ antagonists, alone or in combination with a histamine $H_1$ antagonist, are reported to be useful for the treatment of upper airway allergic response (U.S. Pat. Nos. 5,217,986; 5,352,707 and 5,869,479). Recently, a histamine $H_3$ antagonist (GT-2331) was identified and is being developed by Gliatech Inc. (Gliatech Inc. Press Release Nov. 5, 1998; Bioworld Today, Mar. 2, 1999) for the treatment of CNS disorders.

As noted, the literature related to histamine $H_3$ ligands has been comprehensively reviewed ("The Histamine $H_3$ Receptor—A Target for New Drugs", Leurs, R. and Timmerman, H., (Eds.), Elsevier, 1998). Within this reference the medicinal chemistry of histamine $H_3$ agonists and antagonists was reviewed (see Krause, M. et al., and Phillips, J. G. and Ali, S. M., respectively). The importance of an imidazole moiety containing only a single substitution in the 4-position was noted together with the deleterious effects of additional substitution on activity. Particularly, methylation of the imidazole ring at any of the remaining unsubstituted positions was reported to strongly decrease activity. Additional publications support the hypothesis that an imidazole function is essential for high affinity histamine $H_3$ receptor ligands (see Ali, S. M. et al., J. Med. Chem. 1999, 42:903-909, and Stark, H. et al., and references cited therein). However many imidazole-containing compounds are substrates for histamine methyl transferase, the major histamine metabolizing enzyme in humans, which leads to shortened half-lives and lower bioavailability (see Rouleau, A. et al., J. Pharmacol. Exp. Ther. 1997, 281(3):1085-1094). In addition, imidazole-containing drugs, via their interaction with the cytochrome P450 monooxygenase system, can be targets of unfavorable biotransformations due to enzyme induction or enzyme inhibition (see: Kapetanovic, I. M. and Kupferberg, H. J., Drug Metab. Dispos. 1984, 12(5):560-564; Sheets, J. J. and Mason, J. I., Drug Metab. Dispos. 1984, 12(5):603-606; Back, D. J. and Tjia, J. F., Br. J. Pharmacol. 1985, 85:121-126; Lavrijsen, K. et al., Biochem. Pharmacol. 1986, 35(11):1867-1878; Albengres, E. et al., Drug Safety 1998,18(2):83-97). The poor blood brain barrier penetration of earlier histamine $H_3$ receptor ligands may also be associated with the imidazole fragment (Ganellin, C. R. et al., Arch. Pharm. Pharm. Med. Chem. (Weinheim, Ger.) 1998, 331:395-404).

More recently, several publications have described histamine $H_3$ ligands that do not contain an imidazole moiety, for example: Ganellin, C. R. et al.; Walczynski, K. et al., Arch. Pharm. Pharm. Med. Chem. (Weinheim, Ger.) 1999, 332:

389-398; Walczynski, K. et al., Farmaco 1999, 54:684-694; Linney, I. D. et al., *J. Med. Chem.* 2000, 43:2362-2370; Tozer, M. J. and Kalindjian, S. B., *Exp. Opin. Ther. Patents* 2000, 10:1045-1055; U.S. Pat. No. 5,352,707; PCT Application WO 99/42458, Aug. 26, 1999; PCT Application WO 02/076925; and European Patent Application 0978512, Feb. 9, 2000.

The compounds of the present invention do not contain the imidazole moiety, and its inherent liabilities, and yet maintain potency at the human $H_3$ receptor as determined by receptor binding to the human histamine $H_3$ receptor (see Lovenberg, T. W. et al., *Mol. Pharmacol.* 1999, 55:1101-1107). Screening using the human receptor is particularly important for the identification of new therapies for the treatment of human disease. Conventional binding assays are determined using rat synaptosomes (Garbarg, M. et al., *J. Pharmacol. Exp. Ther.* 1992, 263(1):304-310), rat cortical membranes (West, R. E. et al., *Mol. Pharmacol.* 1990, 38:610-613), and guinea pig brain (Korte, A. et al., *Biochem. Biophys. Res. Commun.* 1990, 168(3):979-986). Only limited studies have been performed previously using human tissue but these allude to significant differences in the pharmacology of rodent and primate receptors (West, R. E. et al., *Eur. J. Pharmacol.* 1999, 377:233-239).

We now describe a series of phenylpiperidines and phenylpyrrolidines with the ability to modulate the activity of the histamine receptor, specifically the $H_3$ receptor, without the inherent problems associated with the presence of an imidazolyl moiety.

SUMMARY OF THE INVENTION

The present invention is directed to pharmaceutically active phenylpiperidines and phenylpyrrolidines, methods of making them, and methods of using them. The invention features a compound of formula (I):

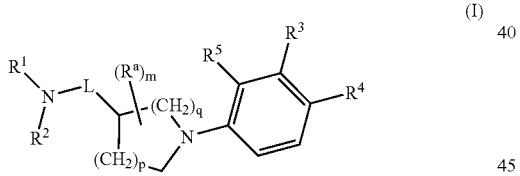

(I)

wherein

L is a direct bond, or an optionally $C_{1-4}$alkyl substituted radical selected from the group consisting of $C_{1-4}$alkylene or $C_{3-4}$alkenylene wherein $NR^1R^2$ is attached to an sp$^3$ hybridized carbon, $C_{3-4}$alkynylene wherein $NR^1R^2$ is attached to an sp$^3$ hybridized carbon, $C_{2-4}$alkylidene wherein $NR^1R^2$ is attached to an sp$^3$ hybridized carbon, aryloxy wherein $NR^1R^2$ is not attached to the oxygen, arylthio wherein $NR^1R^2$ is not attached to the sulfur, $C_{2-4}$alkoxy wherein $NR^1R^2$ is not attached to the oxygen or a carbon attached to the oxygen, $C_{2-4}$alkylthio wherein $NR^1R^2$ is not attached to the sulfur or a carbon attached to the sulfur, and —$C_{2-3}$alkyl-X—$C_{1-2}$alkyl- wherein X is O, S or NH and wherein $NR^1R^2$ is not attached to a carbon attached to X;

p is 0, 1 or 2;

q is 1 or 2; provided that $2 \leq p+q \leq 4$;

$R^1$ is a substituent independently selected from the group consisting of hydrogen, $C_{1-6}$ alkyl, $C_{3-6}$ alkenyl, $C_{3-9}$ carbocyclyl, 3-12 membered heterocyclyl (preferably 5-9 or 5-8-membered heterocyclyl), phenyl, (5-9-membered heterocyclyl)$C_{1-6}$ alkylene, and (phenyl)$C_{1-6}$ alkylene;

$R^2$ is a substituent independently selected from the group consisting of $C_{1-6}$ alkyl, $C_{3-6}$ alkenyl, $C_{3-9}$ membered carbocyclyl, 3-12 membered heterocyclyl (preferably 5-9 or 5-8-membered heterocyclyl), phenyl, (5-9-membered heterocyclyl)$C_{1-6}$ alkylene, and (phenyl)$C_{1-6}$ alkylene;

or $R^1$ and $R^2$ taken together with the nitrogen to which they are attached form a saturated 3-13 membered N-linked heterocyclyl, wherein, in addition to the N-linking nitrogen, the 3-13 membered heterocyclyl may optionally contain between 1 and 3 additional heteroatoms independently selected from O, S, and NH;

wherein $R^1$ and $R^2$ are optionally and independently substituted with 1-3 substituents selected from the group consisting of tert-butyloxycarbonyl, hydroxy, halo, nitro, amino, cyano, carboxamide, $C_{1-6}$ alkyl, $C_{1-6}$ acyl, 5-9-membered heterocyclyl, —N($C_{1-6}$ alkyl)(5-9 membered heterocyclyl), —NH(5-9 membered heterocyclyl), —O(5-9 membered heterocyclyl), (5-9 membered heterocyclyl)$C_{1-3}$ alkylene, $C_{1-2}$-hydroxyalkylene, $C_{1-6}$ alkoxy, ($C_{3-6}$ cycloalkyl)-O—, phenyl, (phenyl)$C_{1-3}$ alkylene, and (phenyl)$C_{1-3}$ alkylene-O—; and wherein each of the preceding substituents of $R^1$ and $R^2$ may optionally have between 1 and 3 substituents independently selected from the group consisting of trifluoromethyl, halo, nitro, cyano, hydroxy, and $C_{1-3}$ alkyl;

one of $R^3$, $R^4$ and $R^5$ is G and the other two independently are hydrogen, fluoro, chloro, bromo, nitro, trifluoromethyl, methyl, or $C_{1-3}$ alkoxy;

G is $L^2Q$;

$L^2$ is unbranched —$(CH_2)_n$— wherein n is an integer from 1 to 7 (preferably n is 1 to 4, more preferably n is 1);

Q is $NR^8R^9$ wherein R is independently selected from hydrogen, $C_{1-6}$ alkyl, $C_{3-6}$ alkenyl, $C_{3-9}$ carbocyclyl, 3-12 membered heterocyclyl (preferably 5-9 or 5-8-membered heterocyclyl), phenyl, (5-9-membered heterocyclyl)$C_{1-6}$ alkylene, and (phenyl)$C_{1-6}$ alkylene; and $R^9$ is independently selected from $C_{1-6}$ alkyl, $C_{3-6}$ alkenyl, 3-9 membered carbocyclyl, 3-13 membered heterocyclyl (preferably 5-9 or 5-8-membered heterocyclyl), phenyl, (5-9-membered heterocyclyl)$C_{1-6}$ alkylene, and (phenyl)$C_{1-6}$ alkylene; or Q is a saturated 3-15 membered N-linked heterocyclyl, wherein, in addition to the N-linking nitrogen, the 3-15 membered heterocyclyl may optionally contain between 1 and 4 additional heteroatoms independently selected from O, S, and NH;

wherein Q is optionally substituted with 1-3 substituents selected (in addition to the preceding paragraph) from the group consisting of tert-butyloxycarbonyl, hydroxy, halo, nitro, amino, cyano, carboxamide, $C_{1-6}$ alkyl, $C_{1-6}$ acyl, 5-9-membered heterocyclyl, —N($C_{1-6}$ alkyl)(5-9 membered heterocyclyl), —NH(5-9 membered heterocyclyl), —O(5-9 membered heterocyclyl), (5-9 membered heterocyclyl)$C_{1-3}$ alkylene, $C_{1-2}$-hydroxyalkylene, $C_{1-6}$ alkoxy, ($C_{3-6}$ cycloalkyl)-O—, phenyl, (phenyl)$C_{1-3}$ alkylene, and (phenyl)$C_{1-3}$ alkylene-O—; and where said substituent groups of Q may optionally have between 1 and 3 substituents independently selected from trifluoromethyl, halo, nitro, cyano, hydroxy, and $C_{1-3}$ alkyl;

$R^a$ are independently $C_{1-3}$ alkyl, triflouromethyl;

m is 0, 1, 2 or 3; and wherein each of the above alkyl, alkylene, alkenyl, heterocyclyl, cycloalkyl, carbocyclyl, and aryl groups may each be independently and optionally substituted with between 1 and 3 substituents independently selected from methoxy, halo, amino, nitro, hydroxy, and $C_{1-3}$ alkyl;

or a pharmaceutically acceptable salt, ester, tautomer, solvate or amide thereof.

The invention also features a pharmaceutical composition comprising a compound of the invention and a pharmaceutically acceptable carrier; and methods of preparing or formulating such compositions. A composition of the invention may further include more than one compound of the invention, or a combination therapy (combination formulation or combination of differently formulated active agents).

The invention also provides methods of treating certain conditions and diseases, each of which methods includes administering a therapeutically effective (or jointly effective) amount of a compound or composition of the invention to a subject in need of such treatment. The disclosed compounds are useful in methods for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof. For example, the invention features methods for preventing, inhibiting the progression of, or treating upper airway allergic response, asthma, itch, nasal congestion and allergic rhinitis.

In yet another embodiment, the disclosed compounds may be used in a combination therapy method including administering a jointly effective dose of an $H_3$ antagonist and administering a jointly effective dose of a histamine $H_1$ antagonist, such as loratidine (CLARITIN™), desloratidine (CLARINEX™), fexofenadine (ALLEGRA™) and cetirizine (ZYRTEC™), for the treatment of allergic rhinitis, nasal congestion, and allergic congestion.

In yet another embodiment, the disclosed compounds may be used in a combination therapy method, including administering a jointly effective dose of an $H_3$ antagonist and administering a jointly effective dose of a neurotransmitter re-uptake blocker, such as a selective serotonin re-uptake inhibitor (SSRI) or a non-selective serotonin, dopamine or norepinephrine re-uptake inhibitor, including fluoxetine (PROZAC™), sertraline (ZOLOFT™), paroxetine (PAXIL™) and amitryptyline, for the treatment of depression, mood disorders or schizophrenia.

Additional features and advantages of the invention will become apparent from the detailed description and examples below, and the appended claims.

DETAILED DESCRIPTION OF THE INVENTION

The present invention provides phenylpiperidine and phenylpyrrolidine compounds useful for the treatment of disorders and conditions modulated by a histamine receptor.

A. Terms Certain terms are defined below and by their usage throughout this disclosure.

As used herein, "$C_{a-b}$" (where a and b are integers) refers to a radical containing from a to b carbon atoms inclusive. For example, $C_{1-3}$ denotes a radical containing 1, 2 or 3 carbon atoms.

As used herein, "halo" or "halogen" shall mean monovalent radicals of chlorine, bromine, fluorine and iodine.

As used herein, the term "alkyl", whether used alone or as part of a substituent group, shall include straight and branched saturated carbon chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms. "Alkylene" refers to a divalent hydrocarbyl group, such as methylene (—$CH_2$—), ethylene (—$CH_2$—$CH_2$—) or propylene (—$CH_2CH_2CH_2$—), and so on.

As used herein, unless otherwise noted, "alkenyl" shall mean an alkylene group with at least two hydrogen atoms replaced with a pi bond to form a carbon-carbon double bond, such as propenyl, butenyl, pentenyl, and so on. Where the alkenyl group is $R^8$ or $R^9$, the open radical (point of attachment to the rest of the molecule) is on an $sp^3$ carbon, as illustrated by allyl, and the double bond or bonds is therefore at least alpha (if not beta, gamma, etc.) to the open radical.

As used herein, "alkylidene" refers to a saturated or unsaturated, branched, straight-chain or cyclic divalent hydrocarbon radical derived by removal of two hydrogen atoms from the same carbon atom of a parent alkane, alkene or alkyne. The divalent radical center forms a double bond with a single atom on the rest of the molecule. Typical alkylidene radicals include, but are not limited to, ethanylidene; propylidenes such as propan-1-ylidene, propan-2-ylidene, cyclopropan-1-ylidene; butylidenes such as butan-1-ylidene, butan-2-ylidene, 2-methyl-propan-1-ylidene, cyclobutan-1-ylidene; and the like.

As used herein, unless otherwise noted, "alkoxy" shall denote an oxygen ether radical of the above-described straight or branched chain alkyl groups. For example, methoxy, ethoxy, n-propoxy, sec-butoxy, t-butoxy, n-hexyloxy and the like.

As used herein, unless otherwise noted, "cycloalkyl" shall denote a three- to eight-membered, saturated monocyclic carbocyclic ring structure. Suitable examples include cyclopropyl, cyclobutyl, cyclopentyl, cyclohexyl, cycloheptyl and cyclooctyl.

As used herein, unless otherwise noted, "cycloalkenyl" shall denote a three- to eight-membered, partially unsaturated, monocyclic, carbocyclic ring structure, wherein the ring structure contains at least one double bond. Suitable examples include cyclohexenyl, cyclopentenyl, cycloheptenyl, cyclooctenyl, cyclohex-1,3-dienyl and the like.

As used herein, unless otherwise noted, "aryl" shall refer to carbocyclic aromatic groups such as phenyl, naphthyl, and the like. Divalent radicals include phenylene (—$C_6H_4$—) which is preferably phen-1,4-diyl, but may also be phen-1,3-diyl.

As used herein, unless otherwise noted, "aralkyl" shall mean any alkyl group substituted with an aryl group such as phenyl, naphthyl, and the like. Examples of aralkyls include benzyl, phenethyl, and phenylpropyl.

As used herein, unless otherwise noted, "carbocyclyl" shall mean any cyclic group consisting of 3-15 carbon atoms, and preferably 6-9 carbon atoms, in the skeleton ring or rings, if the carbocycle is a fused or spiro bicyclic or tricyclic group. A carbocycle may be saturated, unsaturated, partially unsaturated, or aromatic. Examples include cycloalkyl, cycloalkenyl, cycloalkynyl; specific examples include phenyl, benzyl, indanyl, and biphenyl. A carbocycle may have substituents that are not carbon or hydrogen, such as hydroxy, halo, halomethyl, and so on as provided elsewhere herein.

As used herein, unless otherwise noted, the terms "heterocycle", "heterocyclyl" and "heterocyclo" shall denote any three- to fifteen-membered monocyclic, nine- or ten-membered bicyclic or thirteen- or fourteen-membered tricyclic ring structure containing at least one heteroatom moiety selected from the group consisting of NH, O, SO, $SO_2$, (C=O), and S, and preferably NH, O, or S, optionally containing one to four additional heteroatoms in each ring. In some embodiments, the heterocyclyl contains between 1 and 4 or between 1 and 2 additional heteroatoms. Unless otherwise specified, a heterocyclyl may be saturated, partially unsaturated, aromatic or partially aromatic. The heterocyclyl group may be attached at any heteroatom or carbon atom that results in the creation of a stable structure.

Exemplary monocyclic heterocyclic groups can include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, hexahydroazepinyl, 4-piperidinyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1,1-dioxothienyl, dioxanyl, isothiazolidinyl, thietanyl, thiiranyl, triazinyl, triazolyl, tetrazolyl, azatricyclodecanyl, 1,4,7,10-tetraoxa-13-aza-cyclopentadecanyl, azetidinyl and the like.

For example, where Q is a saturated 3-15 membered N-linked heterocyclyl, Q necessarily contains at least one nitrogen, and the carbon atoms are sp$^3$ hybridized. Where Q is a fused bicyclic heterocyclyl, the carbon atom of the ring linked to L is sp$^3$ hybridized, provided the adjacent ring (and the common carbon atoms) may be sp$^2$, such as an indanyl where one of the carbon atoms has been replaced with nitrogen.

In general, exemplary bicyclic heterocyclyls include benzthiazolyl, benzoxazolyl, benzoxazinyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopridyl, furopyridinyl (such as furo{2,3-c}pyridinyl, furo{3,1-b}pyridinyl), or furo{2,3-b}pyridinyl), dihydroisoindolyl, dihydroquinazolinyl (such as 3,4-dihydro-4-oxo-quinazolinyl), tetrahydroquinolinyl (such as 1,2,3,4-tetrahydroquinolinyl), tetrahydroisoquinolinyl(such as 1,2,3,4-tetrahydroisoquiunolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isoindolyl, tetrahydroindoazolyl (such as 4,5,6,7-tetrahydroindazolyl), isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl,

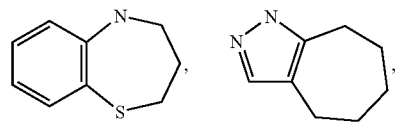

and the like.

Exemplary tricyclic heterocylclic groups include acridinyl, phenoxazinyl, phenazinyl, phenothiazinyl, carbozolyl, perminidinyl, phenanthrolinyl, carbolinyl, naphthothienyl, thianthrenyl, and the like.

Preferred heterocyclyl groups include morpholinyl, thiomorpholinyl, piperidinyl, piperazinyl, pyrrolidinyl, pyrimidinyl, pyridyl, pyrrolyl, imidazolyl, oxazolyl, isoxazolyl, acridinyl, azepinyl, hexahydroazepinyl, azatricyclodecanyl, 1,4,7,10-tetraoxa-13-aza-cyclopentadecanyl, azetidinyl, indolyl, isoindolyl, thiazolyl, thiadiazolyl, quinolinyl, isoquinolinyl, 1,2,3,4-tetrahydroquinolinyl, 1,3,4-trihydroisoquinolinyl, 4,5,6,7-tetrahydroindadolyl, benzoxazinyl, benzoaxzolyl, benzthiazolyl, benzimidazolyl, tetrazolyl, oxadiazolyl,

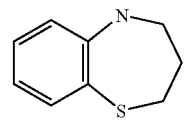

and

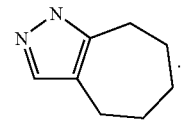

As used herein, unless otherwise noted, the term "heterocyclyl-alkyl" or "heterocyclyl-alkylene" shall denote any alkyl group substituted with a heterocyclyl group, wherein the heterocyclyl-alkyl group is bound through the alkyl portion to the central part of the molecule. Suitable examples of heterocyclyl-alkyl groups include, but are not limited to piperidinylmethyl, pyrrolidinylmethyl, piperidinylethyl, piperazinylmethyl, pyrrolylbutyl, piperidinylisobutyl, pyridylmethyl, pyrimidylethyl, and the like.

When a particular group is "substituted" (e.g., alkyl, alkylene, cycloalkyl, aryl, heterocyclyl, heteroaryl), that group may have one or more substituents, preferably from one to five substituents, more preferably from one to three substituents, most preferably from one to two substituents, independently selected from the list of substituents.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Under standard nomenclature used throughout this disclosure, the terminal portion of the designated side chain is described first, followed by the adjacent functionality toward the point of attachment. Thus, for example, a "phenyl (alkyl)amido(alkyl)" substituent refers to a group of the formula

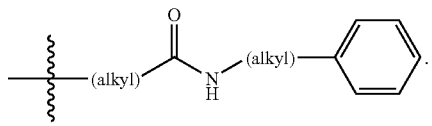

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes prevention, inhibition of onset, or alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Abbreviations used in the specification, particularly in the Schemes and Examples, are as follows:

| | |
|---|---|
| DBAD = | Di-tert-butyl azodicarboxylate |
| DCE = | 1,2-dichloroethane |
| DCM = | Dichloromethane |
| DEAD = | Diethyl azodicarboxylate |
| DMA = | N,N-dimethylacetamide |
| DMAP = | 4-N,N-dimethylamino-pyridine |
| DME = | 1,2-dimethoxyethane |
| DMF = | Dimethylformamide |
| DMSO = | Dimethylsulfoxide |
| RT = | Room temperature |
| TEA = | Triethylamine |
| TFA = | Trifluoroacetic acid |
| THF = | Tetrahydrofuran |

B. Compounds The invention features a compound of formula (I):

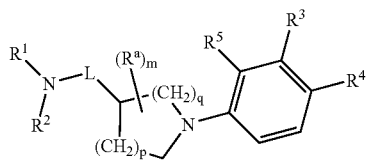

wherein

L is a direct bond, or an optionally $C_{1-4}$alkyl substituted radical selected from the group consisting of $C_{1-4}$alkylene or $C_{3-4}$alkenylene wherein $NR^1R^2$ is attached to an sp$^3$ hybridized carbon, $C_{3-4}$alkynylene wherein $NR^1R^2$ is attached to an sp$^3$ hybridized carbon, $C_{2-4}$alkylidene wherein $NR^1R^2$ is attached to an sp$^3$ hybridized carbon, aryloxy wherein $NR^1NR^2$ is not attached to the oxygen, arylthio wherein $NR^1R^2$ is not attached to the sulfur, $C_{2-4}$alkoxy wherein $NR^1R^2$ is not attached to the oxygen or a carbon attached to the oxygen, $C_{2-4}$alkylthio wherein $NR^1R^2$ is not attached to the sulfur or a carbon attached to the sulfur, and —$C_{2-3}$alkyl-X—$C_{1-2}$alkyl- wherein X is O, S or NH and wherein $NR^1R^2$ is not attached to a carbon attached to X;

p is 0, 1 or 2;

q is 1 or 2; provided that 2<p+q<4;

$R^1$ and $R^2$ are independently selected from hydrogen, $C_{1-3}$ alkyl, allyl, $C_{3-8}$ cycloalkyl, 5-9 membered heterocyclyl, phenyl, and (phenyl)$C_{1-3}$ alkylene, or taken together with the nitrogen to which they are attached, they form a non-aromatic 4-13 membered heterocyclyl optionally including up to two additional heteroatoms independently selected from O, S, and NH; and wherein $R^1$ and $R^2$ are optionally and independently substituted with substituents selected from the group consisting of trifluoromethyl, halo, nitro, cyano, hydroxy, and $C_{1-3}$ alkyl;

one of $R^3$, $R^4$ and $R^5$ is G and the other two independently are hydrogen, fluoro, chloro, bromo, nitro, trifluoromethyl, methyl, or $C_{1-3}$ alkoxy;

G is $L^2Q$;

$L^2$ is unbranched —$(CH_2)_n$— wherein n is an integer from 1 to 7 (preferably n is 1 to 4, more preferably n is 1);

Q is $NR^8R^9$ wherein $R^8$ is independently selected from hydrogen, $C_{1-6}$ alkyl, $C_{3-6}$ alkenyl, $C_{4-9}$ carbocyclyl, 3-12 membered heterocyclyl (preferably 5-9 or 5-8-membered heterocyclyl), phenyl, (5-9-membered heterocyclyl)$C_{1-6}$ alkylene, and (phenyl)$C_{1-6}$ alkylene; and $R^9$ is independently selected from $C_{1-6}$ alkyl, $C_{3-6}$ alkenyl, $C_{4-9}$ membered carbocyclyl, 3-12 membered heterocyclyl (preferably 5-9 or 5-8-membered heterocyclyl), phenyl, (5-9-membered heterocyclyl)$C_{1-6}$ alkylene, and (phenyl)$C_{1-6}$ alkylene; or Q is a saturated 3-15 membered N-linked heterocyclyl, wherein, in addition to the N-linking nitrogen, the 3-15 membered heterocyclyl may optionally contain between 1 and 4 additional heteroatoms independently selected from O, S, and NH;

and wherein Q is optionally substituted with 1-3 substituents selected (in addition to the preceding paragraph) from the group consisting of tert-butyloxycarbonyl, hydroxy, halo, nitro, amino, cyano, carboxamide, $C_{1-6}$ alkyl, $C_{1-6}$ acyl, 5-9-membered heterocyclyl, —N($C_{1-6}$ alkyl)(5-9 membered heterocyclyl), —NH(5-9 membered heterocyclyl), —O(5-9 membered heterocyclyl), (5-9 membered heterocyclyl)$C_{1-3}$ alkylene, $C_{1-2}$-hydroxyalkylene, $C_{1-6}$ alkoxy, ($C_{3-6}$ cycloalkyl)-O—, phenyl, (phenyl)$C_{1-3}$ alkylene, and (phenyl)$C_{1-3}$ alkylene-O—; and where said substituent groups of Q may optionally have between 1 and 3 substituents independently selected from trifluoromethyl, halo, nitro, cyano, hydroxy, and $C_{1-3}$ alkyl;

$R^a$ are independently $C_{1-3}$ alkyl, triflouromethyl;

m is 0, 1, 2 or 3; and wherein each of the above alkyl, alkylene, alkenyl, heterocyclyl, cycloalkyl, carbocyclyl, and aryl groups may each be independently and optionally substituted with between 1 and 3 substituents independently selected from methoxy, halo, amino, nitro, hydroxyl, and $C_{1-3}$ alkyl;

or a pharmaceutically acceptable salt, ester, tautomer, solvate or amide thereof.

The invention features compounds of formula (I). Preferred compounds include those wherein:

(a) NR¹R² taken together form substituted or unsubstituted morpholinyl, thiomorpholinyl, piperidinyl, methylpiperidinyl, piperazinyl, N-methylpiperazinyl, dimethylamino, pyrrolidinyl, azatricyclodecanyl, cyclohexylmethylamino, methylphenethylamino, pyridylamino, anilino, diethylamino, methylethylamino, ethylpropylamino, or dipropylamino;

(b) NR¹R² taken together form a saturated N-linked nitrogen-containing heterocyclyl;

(c) NR¹R² taken together form a substituent selected from substituted or unsubstituted piperidinyl, substituted or unsubstituted piperazinyl, pyrrolinyl, pyrrolidinyl, thiomorpholinyl, and morpholinyl;

(d) NR¹R² taken together form a substituent selected from N-($C_{1-6}$ alkyl)piperazinyl, N-phenyl-piperazinyl, 1,3,8-triaza-spiro{4.5}decyl, and 1,4-dioxa-8-aza-spiro{4.5}decyl;

(e) NR¹R² taken together form a monovalent radical of an amine selected from aziridine, 1,4,7-trioxa-10-aza-cyclododecane, thiazolidine, 1-phenyl-1,3,8-triaza-spiro{4.5}decan-4-one, piperidine-3-carboxylic acid diethylamide, 1,2,3,4,5,6-hexahydro-{2,3'}bipyridinyl, 4-(3-trifluoromethyl-phenyl)-piperazine, 2-piperazin-1-yl-pyrimidine, piperidine-4-carboxylic acid amide, methyl-(2-pyridin-2-yl-ethyl)-amine, {2-(3,4-dimethoxy-phenyl)-ethyl}-methyl-amine, thiomorpholinyl, allyl-cyclopentyl-amine, {2-(1H-indol-3-yl)-ethyl}-methyl-amine, 1-piperidin-4-yl-1,3-dihydro-benzoimidazol-2-one, 2-(piperidin-4-yloxy)-pyrimidine, piperidin-4-yl-pyridin-2-yl-amine, phenylamine, pyridin-2-ylamine;

(f) NR¹R² taken together form a substituent selected from the group consisting of morpholinyl and piperidinyl, wherein said substituent is optionally substituted with between 1 and 3 substituents selected from hydroxy, halo, carboxamide, $C_{1-6}$ alkyl, $C_{1-6}$ acyl, 5-9 membered heterocyclyl, —N($C_{1-6}$ alkyl)(5-9 membered heterocyclyl), —NH(5-9 membered heterocyclyl), —O(5-9 membered heterocyclyl), (5-9 membered heterocyclyl)$C_{1-3}$ alkylene, $C_{1-2}$-hydroxyalkylene, $C_{1-6}$ alkoxy, ($C_{3-6}$ cycloalkyl)-O—, phenyl, (phenyl)$C_{1-3}$ alkylene, and (phenyl)$C_{1-3}$ alkylene-O— where each of above heterocyclyl, phenyl, and alkyl groups may be optionally substituted with from 1 to 3 substituents independently selected from trifluoromethyl, halo, nitro, cyano, hydroxy, and $C_{1-3}$ alkyl;

(g) NR¹R² taken together form a saturated N-linked nitrogen-containing heterocyclyl substituted with a substituent selected from the group consisting of pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl)$C_{1-6}$ alkylene, pyrrolidinyl, and pyrrolyl;

(h) NR¹R² taken together form morpholinyl, piperidinyl, pyrrolidinyl, or diethylamino;

(i) NR¹R² taken together form morpholinyl, piperidinyl, or pyrrolidinyl;

(j) NR¹R² taken together form morpholinyl;

(k) one of R³ and R⁴ is G;

(l) R³ is G;

(m) R⁴ is G;

(n) q is 2 and p is 1;

(O) q is 1 and p is 1;

(p) q is 2 and p is 2;

(q) L is —CH₂—;

(r) L is a direct bond;

(s) L is —CH₂CH₂—;

(t) L² is —CH₂—;

(u) Q is selected from substituted or unsubstituted pyrrolidinyl, piperidinyl, methylpiperidinyl, morpholinyl, thiomorpholinyl, azatricyclodecanyl, cyclohexylamino, cyclohexylmethylamino, piperazinyl, N-methylpiperazinyl, dimethylamino, methylphenethylamino, pyridylamino, anilino, diethylamino, methylethylamino, ethylpropylamino, dipropylamino, or 1,4,7,10-tetraoxa-13-aza-cyclopentadecanyl;

(v) Q is a saturated N-linked nitrogen-containing heterocyclyl;

(w) Q is selected from substituted or unsubstituted piperidinyl, substituted or unsubstituted piperazinyl, pyrrolinyl, pyrrolidinyl, thiomorpholinyl, and morpholinyl;

(x) substituted Q are selected from N-($C_{1-6}$ alkyl)piperazinyl, N-phenyl-piperazinyl, 1,3,8-triaza-spiro{4.5}decyl, and 1,4-dioxa-8-aza-spiro{4.5}decyl;

(y) Q is a monovalent radical of an amine selected from aziridine, 1,4,7-trioxa-10-aza-cyclododecane, thiazolidine, 1-phenyl-1,3,8-triaza-spiro{4.5}decan-4-one, piperidine-3-carboxylic acid diethylamide, 1,2,3,4,5,6-hexahydro-{2,3'}bipyridinyl, 4-(3-trifluoromethyl-phenyl)-piperazine, 2-piperazin-1-yl-pyrimidine, piperidine-4-carboxylic acid amide, methyl-(2-pyridin-2-yl-ethyl)-amine, {2-(3,4-dimethoxy-phenyl)-ethyl}-methyl-amine, thiomorpholinyl, allyl-cyclopentyl-amine, {2-(1H-indol-3-yl)-ethyl}-methyl-amine, 1-piperidin-4-yl-1,3-dihydro-benzoimidazol-2-one, 2-(piperidin-4-yloxy)-pyrimidine, piperidin-4-yl-pyridin-2-yl-amine, phenylamine, and pyridin-2-ylamine;

(z) Q is selected from morpholinyl, pyridyl and piperidinyl, optionally substituted with between 1 and 3 substituents independently selected from hydroxy, halo, carboxamide, $C_{1-6}$ alkyl, $C_{1-6}$ acyl, 5-9 membered or 6-9 membered heterocyclyl, —N($C_{1-6}$ alkyl)(5-9 membered or 6-9 membered heterocyclyl), —NH(5-9 membered or 6-9 membered heterocyclyl), —O(5-9 or 6-9 membered heterocyclyl), (5-9 membered or 6-9 membered heterocyclyl)$C_{1-3}$ alkylene, $C_{1-2}$-hydroxyalkylene, $C_{1-6}$ alkoxy, ($C_{3-6}$ cycloalkyl)-O—, phenyl, (phenyl)$C_{1-3}$ alkylene, and (phenyl)$C_{1-3}$ alkylene-O— where each of above heterocyclyl, phenyl, and alkyl groups may be optionally substituted with from 1 to 3 substituents independently selected from trifluoromethyl, halo, nitro, cyano, hydroxy, and $C_{1-3}$ alkyl;

(aa) Q is substituted with a substituent comprising a 5-9 membered or 6-9 membered heterocyclyl group selected from: pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl)$C_{1-6}$ alkylene, pyrrolidinyl, and pyrrolyl;

(bb) Q is morpholinyl, piperidinyl, pyrrolidinyl, or diethylamino;

(cc) Q is morpholinyl, piperidinyl, or pyrrolidinyl;

(dd) R⁸ is hydrogen;

(ee) R⁹ is $C_{1-6}$ alkyl;

(ff) R⁹ is cyclohexyl;

(gg) R⁸ and R⁹ independently are $C_{1-6}$ alkyl;

(hh) R⁸ and R⁹ are methyl;

(ii) R⁸ and R⁹ are ethyl;

(jj) R⁹ is selected from phenyl or 5-9 membered aromatic heterocyclyl, wherein said phenyl or aromatic heterocyclyl is optionally substituted with 1-3 substituents selected from hydroxy, halo, nitro, cyano, trifluoromethyl, and $C_{1-3}$ alkyl;

(kk) R⁹ is selected from substituted or unsubstituted phenyl, pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl)$C_{1-6}$ alkylene, and pyrrolyl;

(ll) R⁹ is substituted or unsubstituted phenyl;

(mm) R⁹ is substituted or unsubstituted pyridyl;

(nn) wherein $R^1$ and $R^2$ are independently selected from $C_2$ alkyl, or taken together with the nitrogen to which they are attached, they form a non-aromatic 5-6 membered heterocyclyl optionally including an additional heteroatom independently selected from O, S, and NH; one of $R^3$, $R^4$, and $R^5$ is G and the two remaining are H; G is $L^2Q$; $L^2$ is methylene; Q is $NR^1R^9$ wherein $R^8$ is independently selected from hydrogen, $C_{1-2}$ alkyl, $C_3$ alkenyl, $C_{5-9}$ carbocyclyl, 3-12 membered heterocyclyl (preferably 5-9 or 6-9), phenyl, (5-9-membered heterocyclyl)$C_2$ alkylene, and (phenyl)$C_2$ alkylene; and R⁹ is independently selected from $C_{1-2}$ alkyl, $C_3$ alkenyl, $C_{5-9}$ carbocyclyl, 3-12 membered heterocyclyl (for example, 5-9 membered or 6-9 membered heterocyclyl, and in some cases preferably 6-membered), phenyl, (5-9-membered heterocyclyl)$C_{1-6}$ alkylene, and (phenyl)$C_{1-6}$ alkylene; or Q is a saturated 3-15 membered N-linked heterocyclyl (preferably 5-9 or 6-9), wherein, in addition to the N-linking nitrogen, the 3-15 membered heterocyclyl may optionally contain between 1 and 4 additional heteroatoms independently selected from O, S, and NH; wherein each of the above alkyl, alkylene, alkenyl, alkenylene, heterocyclyl, cycloalkyl, and aryl groups may each be independently and optionally substituted with substituents selected from tert-butyloxycarbonyl, hydroxy, halo, nitro, amino, cyano, carboxamide, 6-9-membered heterocyclyl, —NH(6-membered heterocyclyl), —O(6-membered heterocyclyl), $C_{1-2}$ hydroxyalkylene, $C_{1-2}$ alkoxy, phenyl, and benzyl, and where each of above heterocyclyl, phenyl, and alkyl substituent groups of Q may be optionally substituted with trifluoromethyl; or a pharmaceutically acceptable salt, ester, tautomer, solvate or amide thereof;

(oo) (1) $NR^1R^2$ taken together form morpholinyl, piperidinyl, pyrrolidinyl, or diethylamino, and (2) Q is selected from substituted or unsubstituted piperidinyl, piperazinyl, pyrrolinyl, pyrrolidinyl, thiomorpholinyl, and morpholinyl;

(pp) (1) $NR^1R^2$ taken together form piperidinyl or pyrrolidinyl, (2) n is 1, and (3) Q is selected from morpholinyl and piperidinyl;

(qq) Q is piperidinyl or substituted piperidinyl;

(rr) $NR^1R^2$ taken together form piperidinyl, pyrrolidinyl, or diethylamino, n is 1, and wherein Q is $NR^8R^9$ and $R^8$ is H and R⁹ is selected from phenyl or aromatic 5-9 membered heterocyclyl, wherein said phenyl or heterocyclyl is optionally substituted with 1-3 substituents selected from trifluoromethyl, halo, nitro, cyano, hydroxy, and $C_{1-3}$ alkyl;

(ss) $R^a$ is hydrogen; or (tt) combinations of (a) through (ss) above.

Examples of compounds of the invention include:

4-{2-(4-Piperidin-1-ylmethyl-piperidin-1-yl)-benzyl}-morpholine;

Cyclohexyl-{1-(4-pyrrolidin-1-ylmethyl-phenyl)-piperidin-4-ylmethyl}-amine;

1-{1-(4-Pyrrolidin-1-ylmethyl-phenyl)-piperidin-4-ylmethyl}-azacyclotridecane;

Diethyl-{1-(4-pyrrolidin-1-ylmethyl-phenyl)-piperidin-4-ylmethyl}-amine;

Dimethyl-{1-(4-pyrrolidin-1-yl methyl-phenyl)-piperidin-4-ylmethyl}-amine;

1-Methyl-4-{1-(4-pyrrolidin-1-ylmethyl-phenyl)-piperidin-4-ylmethyl}-piperazine;

1-{1-(4-Pyrrolidin-1-ylmethyl-phenyl)-piperidin-4-ylmethyl}-piperidin-4-ol;

4-{1-(4-Pyrrolidin-1-ylmethyl-phenyl)-piperidin-4-ylmethyl}-thiomorpholine;

1-{1-(4-Pyrrolidin-1-ylmethyl-phenyl)-piperidin-4-ylmethyl}-piperidine;

4-{1-(4-Pyrrolidin-1-ylmethyl-phenyl)-piperidin-4-ylmethyl}-morpholine;

4-{3-(4-Pyrrolidin-1-ylmethyl-piperidin-1-yl)-benzyl}-thiomorpholine;

4-{3-(4-Pyrrolidin-1-ylmethyl-piperidin-1-yl)-benzyl}-morpholine;

4-Pyrrolidin-1-ylmethyl-1-(3-pyrrolidin-1-ylmethyl-phenyl)-piperidine;

1-{3-(4-Pyrrolidin-1-ylmethyl-piperidin-1-yl)-benzyl}-piperidine;

1-{4-(4-Pyrrolidin-1-ylmethyl-piperidin-1-yl)-benzyl}-azacyclotridecane;

Cyclohexyl-{4-(4-pyrrolidin-1-ylmethyl-piperidin-1-yl)-benzyl}-amine;

1-{4-(4-Pyrrolidin-1-ylmethyl-piperidin-1-yl)-benzyl}-piperidin-4-ol;

1-Methyl-4-{4-(4-pyrrolidin-1-ylmethyl-piperidin-1-yl)-benzyl}-piperazine;

4-{4-(4-Pyrrolidin-1-ylmethyl-piperidin-1-yl)-benzyl}-thiomorpholine;

4-{4-(4-Pyrrolidin-1-ylmethyl-piperidin-1-yl)-benzyl}-morpholine;

Dimethyl-{4-(4-pyrrolidin-1-ylmethyl-piperidin-1-yl)-benzyl}-amine;

4-{2-(4-Pyrrolidin-1-ylmethyl-piperidin-1-yl)-benzyl}-morpholine;

4-{1-(4-Piperidin-1-ylmethyl-phenyl)-piperidin-4-ylmethyl}-morpholine;

1-{4-(4-Pyrrolidin-1-ylmethyl-piperidin-1-yl)-benzyl}-piperidine;

Cyclohexyl-{1-(4-morpholin-4-ylmethyl-phenyl)-piperidin-4-yl}-amine;

Cyclohexyl-methyl-{1-(4-morpholin-4-ylmethyl-phenyl)-piperidin-4-yl}-amine;

4-{4-{4-(4-Methyl-piperazin-1-yl)-piperidin-1-yl}-benzyl}-morpholine;

Ethyl-methyl-{1-(4-morpholin-4-ylmethyl-phenyl)-piperidin-4-yl}-amine;

4-{1-(4-Morpholin-4-ylmethyl-phenyl)-piperidin-4-yl}-morpholine;

4-{4-(4-Pyrrolidin-1-yl-piperidin-1-yl)-benzyl}-morpholine;

1'-(4-Morpholin-4-ylmethyl-phenyl)-{1,4'}bipiperidinyl;

1'-(4-Piperidin-1-ylmethyl-phenyl)-{1,4'}bipiperidinyl;

(4-{1,4'}Bipiperidinyl-1'-yl-benzyl)-pyridin-2-yl-amine;

Phenyl-{1-(4-pyrrolidin-1-ylmethyl-phenyl)-piperidin-4-ylmethyl}-amine;

Pyridin-2-yl-{1-(4-pyrrolidin-1-ylmethyl-phenyl)-piperidin-4-ylmethyl}-amine;

1-{1-(4-Piperidin-1-ylmethyl-phenyl)-piperidin-4-ylmethyl}-piperidine;

4-Pyrrolidin-1-ylmethyl-1-(4-pyrrolidin-1-ylmethyl-phenyl)-piperidine;

(4-Fluoro-phenyl)-{4-(4-pyrrolidin-1-ylmethyl-piperidin-1-yl)-benzyl}-amine;

4-{2-{1-(4-Piperidin-1-ylmethyl-phenyl)-pyrrolidin-3-yl}-ethyl}-morpholine;

Diethyl-{2-{1-(4-piperidin-1-ylmethyl-phenyl)-pyrrolidin-3-yl}-ethyl}-amine;

Methyl-phenethyl-{2-{1-(4-piperidin-1-ylmethyl-phenyl)-pyrrolidin-3-yl}-ethyl}-amine;

1-[4-(4-Pyrrolidin-1-ylmethyl-piperidin-1-yl)-3-trifluoromethyl-benzyl]-piperidine;

1-(2-Nitro-4-pyrrolidin-1-ylmethyl-phenyl)-4-pyrrolidin-1-ylmethyl-piperidine;

4-[3-Nitro-4-(4-pyrrolidin-1-ylmethyl-piperidin-1-yl)-benzyl]-morpholine;

1-[3-Nitro-4-(4-pyrrolidin-1-ylmethyl-piperidin-1-yl)-benzyl]-piperidin-4-ol;

1-[4-(Pyrrolidin-1-ylmethyl-piperidin-1-yl)-2-trifluoromethyl-benzyl]-piperidine;

1-Isopropyl-4-[3-methyl-4-(4-pyrrolidin-1-ylmethyl-piperidin-1-yl)-benzyl]-piperazine;

1-(2-Methyl-4-pyrrolidin-1-ylmethyl-phenyl)-4-pyrrolidin-1-ylmethyl-pyrrolidine;

1-[3-Methyl-4-(4-pyrrolidin-1-ylmethyl-piperidin-1-yl)-benzyl]-pyrrolidine;

1-{1-[4-(4-Pyrrolidin-1-yl-piperidin-1-ylmethyl)-2-trifluoromethyl-phenyl]-piperidin-4-ylmethyl}-pyrrolidine;

1-(1-{3-Trifluoromethyl-4-[4-(4-trifluoromethyl-phenyl)-piperidin-1-ylmethyl]-phenyl}-piperidin-4-ylmethyl)-pyrrolidine;

1-{1-[2-Fluoro-4-(4-phenyl-piperidin-1-ylmethyl)-phenyl]-piperidin-4-ylmethyl}-pyrrolidine;

[3-Fluoro-4-(4-pyrrolidin-1-ylmethyl-piperidin-1-yl)-benzyl]-dimethyl-amine;

1-[3-Fluoro-4-(4-pyrrolidin-1-ylmethyl-piperidin-1-yl)-benzyl]-piperidine;

13-[4-(4-Pyrrolidin-1-ylmethyl-piperidin-1-yl)-2-trifluoromethyl-benzyl]-1,4,7,10-tetraoxa-13-aza-cyclopentadecane ditrifluoromethanesulfonate; and {1-[4-(4-Pyrrolidin-1-ylmethyl-piperidin-1-yl)-3-trifluoromethyl-benzyl]-piperidin-4-yl}-methanol.

Preferred example compounds include:

(4-{1,4'}Bipiperidinyl-1'-yl-benzyl)-pyridin-2-yl-amine;

1'-(4-Morpholin-4-ylmethyl-phenyl)-{1,4'}bipiperidinyl;

1'-(4-Piperidin-1-ylmethyl-phenyl)-{1,4'}bipiperidinyl;

1-{1-(4-Piperidin-1-ylmethyl-phenyl)-piperidin-4-ylmethyl}-piperidine;

4-{1-(4-Piperidin-1-ylmethyl-phenyl)-piperidin-4-ylmethyl}-morpholine;

1-{1-(4-Pyrrolidin-1-ylmethyl-phenyl)-piperidin-4-ylmethyl}-piperidin-4-ol;

1-{1-(4-Pyrrolidin-1-ylmethyl-phenyl)-piperidin-4-ylmethyl}-piperidine;

1-{3-(4-Pyrrolidin-1-ylmethyl-piperidin-1-yl)-benzyl}-piperidine;

1-{4-(4-Pyrrolidin-1-ylmethyl-piperidin-1-yl)-benzyl}-azacyclotridecane;

1-{4-(4-Pyrrolidin-1-ylmethyl-piperidin-1-yl)-benzyl}-piperidin-4-ol;

1-{4-(4-Pyrrolidin-1-ylmethyl-piperidin-1-yl)-benzyl}-piperidine;

1-Methyl-4-{1-(4-pyrrolidin-1-ylmethyl-phenyl)-piperidin-4-ylmethyl}-piperazine;

1-Methyl-4-{4-(4-pyrrolidin-1-ylmethyl-piperidin-1-yl)-benzyl}-piperazine;

4-{1-(4-Pyrrolidin-1-ylmethyl-phenyl)-piperidin-4-ylmethyl}-morpholine;

4-{1-(4-Pyrrolidin-1-ylmethyl-phenyl)-piperidin-4-ylmethyl}-thiomorpholine;

4-{3-(4-Pyrrolidin-1-ylmethyl-piperidin-1-yl)-benzyl}-thiomorpholine;

4-{4-(4-Pyrrolidin-1-ylmethyl-piperidin-1-yl)-benzyl}-thiomorpholine;

4-{2-{1-(4-Piperidin-1-ylmethyl-phenyl)-pyrrolidin-3-yl}-ethyl}-morpholine;

4-Pyrrolidin-1-ylmethyl-1-(3-pyrrolidin-1-ylmethyl-phenyl)-piperidine;

4-Pyrrolidin-1-ylmethyl-1-(4-pyrrolidin-1-ylmethyl-phenyl)-piperidine;

Cyclohexyl-{1-(4-pyrrolidin-1-ylmethyl-phenyl)-piperidin-4-ylmethyl}-amine;

Cyclohexyl-{4-(4-pyrrolidin-1-ylmethyl-piperidin-1-yl)-benzyl}-amine;

Cyclohexyl-methyl-{1-(4-morpholin-4-ylmethyl-phenyl)-piperidin-4-yl}-amine;

Diethyl-{1-(4-pyrrolidin-1-ylmethyl-phenyl)-piperidin-4-ylmethyl}-amine;

Diethyl-{2-{1-(4-piperidin-1-ylmethyl-phenyl)-pyrrolidin-3-yl}-ethyl}-amine;

Dimethyl-{1-(4-pyrrolidin-1-ylmethyl-phenyl)-piperidin-4-ylmethyl}-amine;

Dimethyl-{4-(4-pyrrolidin-1-ylmethyl-piperidin-1-yl)-benzyl}-amine;

Methyl-phenethyl-{2-{1-(4-piperidin-1-ylmethyl-phenyl)-pyrrolidin-3-yl}-ethyl}-amine;

Phenyl-{1-(4-pyrrolidin-1-ylmethyl-phenyl)-piperidin-4-ylmethyl}-amine;

Pyridin-2-yl-{1-(4-pyrrolidin-1-ylmethyl-phenyl)-piperidin-4-ylmethyl}-amine;

1-(2-Nitro-4-pyrrolidin-1-ylmethyl-phenyl)-4-pyrrolidin-1-ylmethyl-piperidine;

1-[3-Nitro-4-(4-pyrrolidin-1-ylmethyl-piperidin-1-yl)-benzyl]-piperidin-4-ol;

1-[4-(4-Pyrrolidin-1-ylmethyl-piperidin-1-yl)-2-trifluoromethyl-benzyl]-piperidine;

1-(2-Methyl-4-pyrrolidin-1-ylmethyl-phenyl)-4-pyrrolidin-1-ylmethyl-pyrrolidine;

1-[3-Methyl-4-(4-pyrrolidin-1-ylmethyl-piperidin-1-yl)-benzyl]-pyrrolidine;

1-{1-[4-(4-Pyrrolidin-1-yl-piperidin-1-ylmethyl)-2-trifluoromethyl-phenyl]-piperidin-4-ylmethyl}-pyrrolidine;

1-{1-[2-Fluoro-4-(4-phenyl-piperidin-1-ylmethyl)-phenyl]-piperidin-4-ylmethyl}-pyrrolidine;

[3-Fluoro-4-(4-pyrrolidin-1-ylmethyl-piperidin-1-yl)-benzyl]-dimethyl-amine; and 1-[3-Fluoro-4-(4-pyrrolidin-1-ylmethyl-piperidin-1-yl)-benzyl]-piperidine.

More preferred example compounds include:

1'-(4-Piperidin-1-ylmethyl-phenyl)-{1,4'}bipiperidinyl;

1-{1-(4-Piperidin-1-ylmethyl-phenyl)-piperidin-4-ylmethyl}-piperidine;

4-{1-(4-Piperidin-1-ylmethyl-phenyl)-piperidin-4-ylmethyl}-morpholine;

1-{1-(4-Pyrrolidin-1-ylmethyl-phenyl)-piperidin-4-ylmethyl}-piperidin-4-ol;

1-{1-(4-Pyrrolidin-1-ylmethyl-phenyl)-piperidin-4-ylmethyl}-piperidine;

1-{4-(4-Pyrrolidin-1-ylmethyl-piperidin-1-yl)-benzyl}-piperidin-4-ol;

1-{4-(4-Pyrrolidin-1-ylmethyl-piperidin-1-yl)-benzyl}-piperidine;

1-Methyl-4-{1-(4-pyrrolidin-1-ylmethyl-phenyl)-piperidin-4-ylmethyl}-piperazine;

4-{1-(4-Pyrrolidin-1-ylmethyl-phenyl)-piperidin-4-ylmethyl}-morpholine;

4-{1-(4-Pyrrolidin-1-ylmethyl-phenyl)-piperidin-4-ylmethyl}-thiomorpholine;

4-{4-(4-Pyrrolidin-1-ylmethyl-piperidin-1-yl)-benzyl}-thiomorpholine;

4-{2-{1-(4-Piperidin-1-ylmethyl-phenyl)-pyrrolidin-3-yl}-ethyl}-morpholine;

4-Pyrrolidin-1-ylmethyl-1-(4-pyrrolidin-1-ylmethyl-phenyl)-piperidine;

Cyclohexyl-{1-(4-pyrrolidin-1-ylmethyl-phenyl)-piperidin-4-ylmethyl}-amine;

Cyclohexyl-{4-(4-pyrrolidin-1-ylmethyl-piperidin-1-yl)-benzyl}-amine;

Diethyl-{1-(4-pyrrolidin-1-ylmethyl-phenyl)-piperidin-4-ylmethyl}-amine;

Diethyl-{2-{1-(4-piperidin-1-ylmethyl-phenyl)-pyrrolidin-3-yl}-ethyl}-amine;

Dimethyl-{1-(4-pyrrolidin-1-ylmethyl-phenyl)-piperidin-4-ylmethyl}-amine;

Dimethyl-{4-(4-pyrrolidin-1-ylmethyl-piperidin-1-yl)-benzyl}-amine;

Methyl-phenethyl-{2-{1-(4-piperidin-1-ylmethyl-phenyl)-pyrrolidin-3-yl}-ethyl}-amine;

Pyridin-2-yl-{1-(4-pyrrolidin-1-ylmethyl-phenyl)-piperidin-4-ylmethyl}-amine;

1-(2-Nitro-4-pyrrolidin-1-ylmethyl-phenyl)-4-pyrrolidin-1-ylmethyl-piperidine;

1-[3-Nitro-4-(4-pyrrolidin-1-ylmethyl-piperidin-1-yl)-benzyl]-piperidin-4-ol;

1-(2-Methyl-4-pyrrolidin-1-ylmethyl-phenyl)-4-pyrrolidin-1-ylmethyl-pyrrolidine;

[3-Fluoro-4-(4-pyrrolidin-1-ylmethyl-piperidin-1-yl)-benzyl]-dimethyl-amine; and 1-[3-Fluoro-4-(4-pyrrolidin-1-ylmethyl-piperidin-1-yl)-benzyl]-piperidine.

Even more preferred example compounds include:

1-{1-(4-Pyrrolidin-1-ylmethyl-phenyl)-piperidin-4-ylmethyl}-piperidin-4-ol;

1-{1-(4-Pyrrolidin-1-ylmethyl-phenyl)-piperidin-4-ylmethyl}-piperidine;

1-Methyl-4-{1-(4-pyrrolidin-1-ylmethyl-phenyl)-piperidin-4-ylmethyl}-piperazine;

1-{4-(4-Pyrrolidin-1-ylmethyl-piperidin-1-yl)-benzyl}-piperidine;

4-{1-(4-Pyrrolidin-1-ylmethyl-phenyl)-piperidin-4-ylmethyl}-morpholine;

4-{1-(4-Pyrrolidin-1-ylmethyl-phenyl)-piperidin-4-ylmethyl}-thiomorpholine;

4-{2-{1-(4-Piperidin-1-ylmethyl-phenyl)-pyrrolidin-3-yl}-ethyl}-morpholine;

4-Pyrrolidin-1-ylmethyl-1-(4-pyrrolidin-1-ylmethyl-phenyl)-piperidine;

Cyclohexyl-{1-(4-pyrrolidin-1-ylmethyl-phenyl)-piperidin-4-ylmethyl}-amine;

Cyclohexyl-{4-(4-pyrrolidin-1-ylmethyl-piperidin-1-yl)-benzyl}-amine;

Diethyl-{1-(4-pyrrolidin-1-ylmethyl-phenyl)-piperidin-4-ylmethyl}-amine;

Diethyl-{2-{1-(4-piperidin-1-ylmethyl-phenyl)-pyrrolidin-3-yl}-ethyl}-amine;

Dimethyl-{1-(4-pyrrolidin-1-ylmethyl-phenyl)-piperidin-4-ylmethyl}-amine;

Methyl-phenethyl-{2-{1-(4-piperidin-1-ylmethyl-phenyl)-pyrrolidin-3-yl}-ethyl}-amine;

1-(2-Nitro-4-pyrrolidin-1-ylmethyl-phenyl)-4-pyrrolidin-1-ylmethyl-piperidine; and 1-(2-Methyl-4-pyrrolidin-1-ylmethyl-phenyl)-4-pyrrolidin-1-ylmethyl-pyrrolidine.

Yet even more preferred example compounds include:

1-{1-(4-Pyrrolidin-1-ylmethyl-phenyl)-piperidin-4-ylmethyl}-piperidin-4-ol;

1-{1-(4-Pyrrolidin-1-ylmethyl-phenyl)-piperidin-4-ylmethyl}-piperidine;

4-Pyrrolidin-1-ylmethyl-1-(4-pyrrolidin-1-ylmethyl-phenyl)-piperidine;

4-{2-{1-(4-Piperidin-1-ylmethyl-phenyl)-pyrrolidin-3-yl}-ethyl}-morpholine;

Cyclohexyl-{1-(4-pyrrolidin-1-ylmethyl-phenyl)-piperidin-4-ylmethyl}-amine;

Diethyl-{1-(4-pyrrolidin-1-ylmethyl-phenyl)-piperidin-4-ylmethyl}-amine;

Diethyl-{2-{1-(4-piperidin-1-ylmethyl-phenyl)-pyrrolidin-3-yl}-ethyl}-amine; and 1-(2-Methyl-4-pyrrolidin-1-ylmethyl-phenyl)-4-pyrrolidin-1-ylmethyl-pyrrolidine.

The invention also provides compounds that are useful as synthetic intermediates of the compounds of the invention. Such compounds, which themselves may or may not have pharmaceutical activity, include those provided in the schemes and synthetic examples.

The invention also contemplates compounds isotopically labelled to be detectable by positron emission tomography (PET) or single-photon emission computed tomography (SPECT) useful for studying $H_3$-mediated disorders.

During any of the processes for preparation of the compounds of the present invention, it may be necessary and/or desirable to protect sensitive or reactive groups on any of the molecules concerned. In addition, compounds of the invention may be modified by using protecting groups; such compounds, precursors, or prodrugs are also within the scope of the invention. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", $3^{rd}$ ed., John Wiley & Sons, 1999. The protecting groups may be removed at a convenient subsequent stage using methods known from the art.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-{(2-chloro-4-methyl)phenyl}-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(Imidazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate (levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate(tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate Sulfonates Examples of sulfonates include sulfate, methanesulfonate (mesylate), benzylsulfonate, and tosylate.

Protection for 1,2- and 1,3-Diols

Cyclic Acetals and Ketals

Examples of cyclic acetals and ketals include methylene, ethylidene, 1-t-butylethylidene, 1-phenylethylidene, (4-methoxyphenyl)ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Examples of cyclic ortho esters include methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Silyl Derivatives

Examples of silyl derivatives include di-t-butylsilylene group, and 1,3-(1,1,3,3-tetraisopropyldisiloxanylidene) derivative.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-{9-(10,10-dioxo-10,10,10,10-tetrahydrothioxanthyl)}methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, {2-(1,3-dithianyl)}methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of amides include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protective Groups

Examples of Special NH Protective Groups Include:

N-Alkyl and N-Aryl Amines

N-methyl, N-allyl, N-{2-(trimethylsilyl)ethoxy}methyl, N-3-acetoxypropyl, N-(1-isopropyl-4-nitro-2-oxo-3-pyrrolin-3-yl), quaternary ammonium salts, N-benzyl, N-4-methoxybenzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-{(2-pyridyl)mesityl}methylene, and N-(N',N'-dimethylaminomethylene).

Protection for the Carbonyl Group

Acyclic Acetals and Ketals

Examples of acyclic acetals and ketals include dimethyl, bis(2,2,2-trichloroethyl), dibenzyl, bis(2-nitrobenzyl) and diacetyl.

Cyclic Acetals and Ketals

Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy and 1,5-dihydro-3H-2,4-benzodioxepin.

Acyclic Dithio Acetals and Ketals

Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl and S,S'-diacetyl.

Cyclic Dithio Acetals and Ketals

Examples of cyclic dithio acetals and ketals include 1,3-dithiane, 1,3-dithiolane and 1,5-dihydro-3H-2,4-benzodithiepin.

Acyclic Monothio Acetals and Ketals

Examples of acyclic monothio acetals and ketals include O-trimethylsilyl-S-alkyl, O-methyl-S-alkyl or —S-phenyl and O-methyl-S-2-(methylthio)ethyl.

Cyclic Monothio Acetals and Ketals

Examples of cyclic monothio acetals and ketals include 1,3-oxathiolanes.

Miscellaneous Derivatives

O-Substituted Cyanohydrins

Examples of O-substituted cyanohydrins include O-acetyl, O-trimethylsilyl, O-1-ethoxyethyl and O-tetrahydropyranyl.

Substituted Hydrazones

Examples of substituted hydrazones include N,N-dimethyl and 2,4-dinitrophenyl.

Oxime Derivatives

Examples of oxime derivatives include O-methyl, O-benzyl and O-phenylthiomethyl.

Imines

Substituted Methylene Derivatives, Cyclic Derivatives

Examples of substituted methylene and cyclic derivatives include oxazolidines, 1-methyl-2-(1'-hydroxyalkyl)imidazoles, N,N'-dimethylimidazolidines, 2,3-dihydro-1,3-benzothiazoles, diethylamine adducts, and methylaluminum bis (2,6-di-t-butyl-4-methylphenoxide)(MAD)complex.

Monoprotection of Dicarbonyl Compounds

Selective Protection of α- and β-Diketones

Examples of selective protection of α- and β-diketones include enamines, enol acetates, enol ethers, methyl, ethyl, 1-butyl, piperidinyl, morpholinyl, 4-methyl-1,3-dioxolanyl, pyrrolidinyl, benzyl, S-butyl, and trimethylsilyl.

Cyclic Ketals, Monothio and Dithio Ketals Examples of cyclic ketals, monothio and dithio ketals include bismethylenedioxy derivatives and tetramethylbismethylenedioxy derivatives.

Protection for the Carboxyl Group

Esters

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaminocobalt(III) complex.

Stannyl Esters

Examples of stannyl esters include triethylstannyl and tri-n-butylstannyl.

Amides and Hydrazides

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl.

The compounds of the invention can be prepared according to the methods described in the next section.

C. Synthesis

The compounds of the invention can be prepared according to traditional synthetic organic methods and matrix or combinatorial chemistry methods, as shown in Schemes 1-7 below and in Examples 1-82. A person of ordinary skill will be aware of variations and adaptations of the schemes and examples provided to achieve the compounds of the invention.

One skilled in the art will recognize that synthesis of the compounds of the present invention may be effected by purchasing intermediate or protected intermediate compounds described in any of the schemes disclosed herein. Throughout the schemes when the reacting functionality is located at $R^3$, one skilled in the art will recognize that the choice of $R^3$ is illustrative only and that the reacting functionality could also be located at $R^4$ or $R^5$.

One skilled in the art will further recognize that during any of the processes for preparation of the compounds of the present invention, it may be necessary and/or desirable to protect sensitive or reactive groups on any of the molecules concerned. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", John Wiley & Sons, 1991. The protecting groups may be removed at a convenient subsequent stage using methods known from the art.

Compounds of formula (VIII) may be prepared according to the processes outlined in Scheme 1.

Scheme 1.

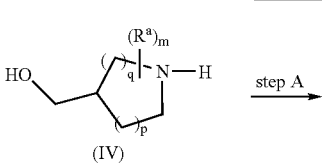

(IV) step A

-continued

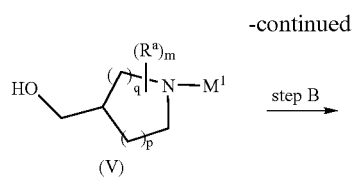

Scheme 2.

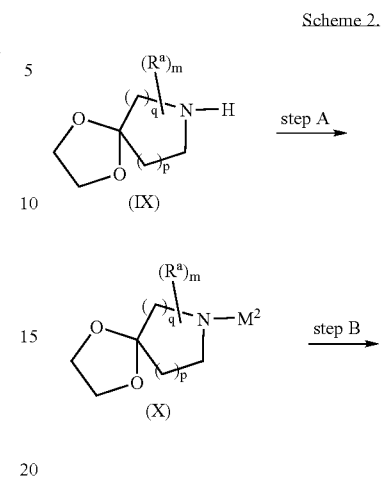

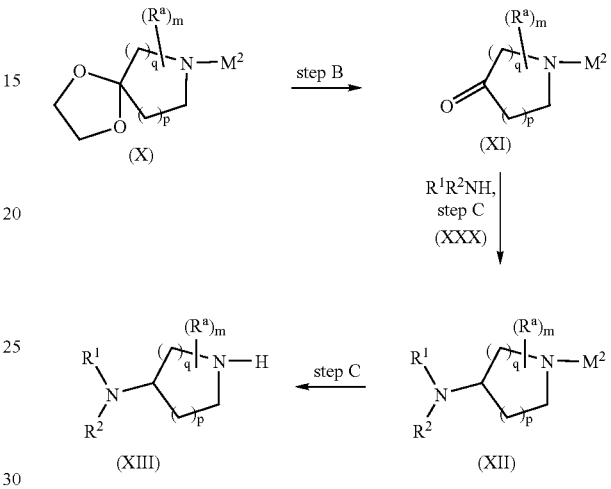

A compound of formula (VIII) is prepared as outlined in Scheme 1 from a compound of formula (IV). A compound of formula (IV) is reacted with a reagent capable of introducing a nitrogen-protecting group $M^1$ under nitrogen-protection conditions. In a particularly preferred embodiment, a compound of formula (IV) is reacted with di-tert-butyl dicarbonate in DCM at room temperature. A compound of formula (VI) is obtained from a compound of formula (V) by reacting a compound of formula (V) with an oxidizing agent in a solvent at room temperature under alcohol oxidizing conditions. In a preferred embodiment, a compound of formula (V) is reacted with 4-methylmorpholine N-oxide and tetrapropylammonium perruthenate in the presence of a dehydrating agent such as 4A molecular sieves in a solvent such as DCE or DCM. A compound of formula (VII) is obtained from a compound of formula (VI) by reacting a compound of formula (VI) with a compound of formula (XXX) under reductive amination conditions in the presence of a reductant such as sodium triacetoxyborohydride, sodium cyanoborohydride, or phenylsilane in a solvent such as THF, DCE, DCM, methanol, ethanol, or ether at a temperature between 0 and 80° C. One skilled in the art will recognize that the use of a promotor or catalyst with acidic character such as organometallic complexes or carboxylic acids may increase the rate of the reaction and/or reduce the formation of by-products. In a particularly preferred embodiment, a compound of formula (VI) is reacted with a compound of formula (XXX), acetic acid, and sodium triacetoxyborohydride in DCE at room temperature. A compound of formula (VIII) is obtained from a compound of formula (VII) by reacting a compound of formula (VII) with a reagent capable of removing the protecting group $M^1$ under nitrogen deprotection conditions. In a preferred embodiment a compound of formula (VII), in which the protecting group $M^1$ is tert-butyl carbamoyl, is reacted with an acid such as anhydrous hydrogen chloride in a solvent such as dioxane at room temperature.

Compounds of formula (XIII) may be prepared according to the processes outlined in Scheme 2.

A compound of formula (XIII) is prepared as outlined in Scheme 2 from a compound of formula (IX). A compound of formula (IX) is reacted with a reagent capable of converting a compound of formula (IX) to a compound of formula (X), in which $M^2$ represents a nitrogen-protecting group, under nitrogen-protecting conditions. In a preferred embodiment, the protecting group $M^2$ is benzyl and is introduced by reacting a compound of formula (IX) with benzaldehyde under reductive amination conditions as outlined in Scheme 1, step C. A compound of formula (XI) is obtained from a compound of formula (X) by reacting a compound of formula (X) with an acid in a solvent at a temperature from 0 to 100° C. under ketal hydrolysis conditions. In a particularly preferred embodiment, a compound of formula (X) is reacted with hydrochloric acid in water at 100° C. A compound of formula (XII) is obtained from a compound of formula (XI) by reacting a compound of formula (XI) with a compound of formula (XXX) under reductive amination conditions, as described in Scheme 1, step C. A compound of formula (XIII) is obtained from a compound of formula (XII) by reacting a compound of formula (XII) with a reagent capable of removing the protecting group $M^2$. In a preferred embodiment, a compound of formula (XII), in which $M^2$ represents the benzyl group, is reacted with a reducing agent such as hydrogen gas in the presence of a hydrogenation catalyst such as palladium on carbon at room temperature.

Compounds of formula (XVII) or formula (XX) may be prepared as outlined according to the processes outlined in Scheme 3.

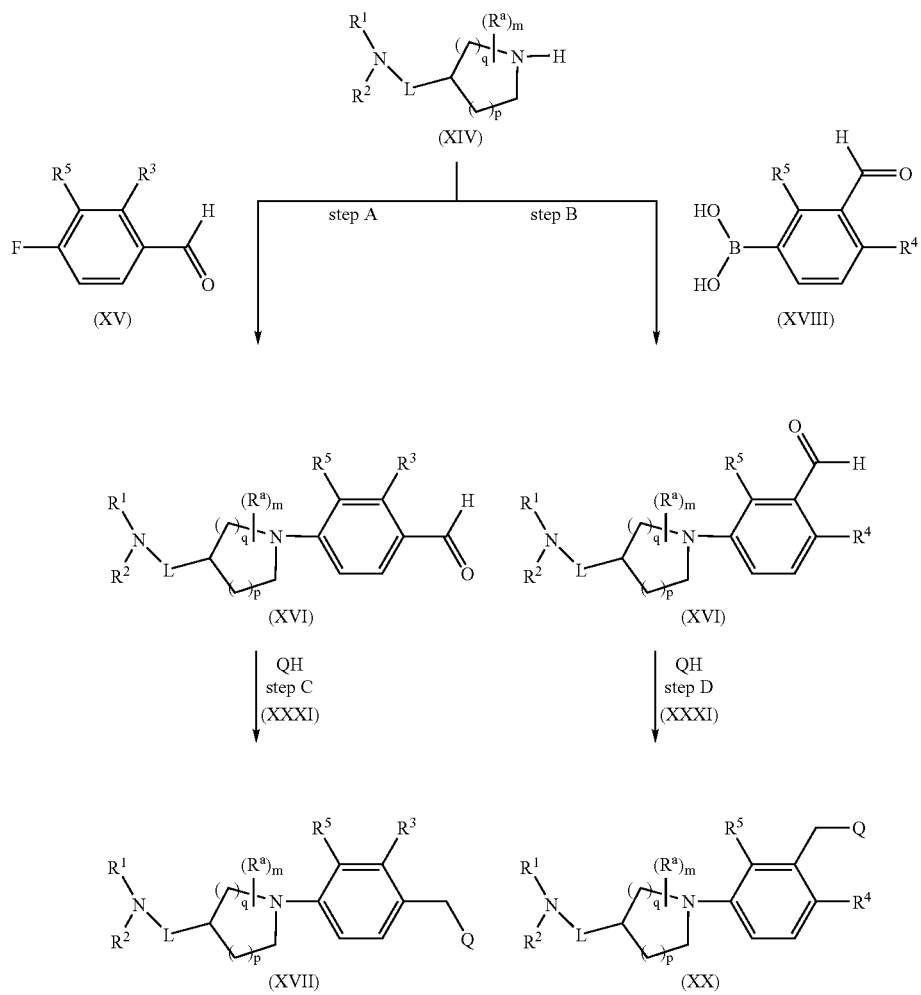

Scheme 3.

A compound of formula (XVII) or formula (XX) is prepared as outlined in Scheme 3 from a compound of formula (XIV). A compound of formula (XVI) is prepared from a compound of formula (XIV) by reacting a compound of formula (XIV) with a compound of formula (XV) under nucleophilic, aromatic substitution conditions. In a preferred embodiment, a compound of formula (XIV) is reacted with a compound of formula (XV) in the presence of a base such as sodium carbonate, potassium carbonate, cesium carbonate, sodium hydride, or tetramethylguanidine in a solvent such as DMF, DMAC, THF, DME, DCM, or ether at a temperature between 0 and 150° C. In a particularly preferred embodiment, a compound of formula (XIV) is reacted with a compound of formula (XV) in the presence of cesium carbonate or potassium carbonate in DMF at 100° C. A compound of formula (XVII) is prepared by reacting a compound of formula (XVI) with a compound of formula (XXXI) under reductive amination conditions, as described in Scheme 1, step C. A compound of formula (XIX) is obtained from a compound of formula (XIV) by reacting a compound of formula (XIV) with a compound of formula (XVIII) under amine N-arylation conditions. In a preferred embodiment, a compound of formula (XIV) is reacted with a compound of formula (XVIII) in the presence of a metal complex such as copper(II) acetate, a base such as triethylamine or 2,6-lutidine in the presence of an air atmosphere in a solvent such as toluene or DCM. One skilled in the art will recognize that the addition of a carboxylic acid such as myristic acid and/or a drying agent such as 4A molecular sieves may improve the yield of the reaction and/or reduce by-product formation. In a particularly preferred embodiment, the metal complex is copper(III) acetate, the base is triethylamine, the solvent is DCM, and the reaction is performed in the presence of 4A molecular sieves. A compound of formula (XX) is prepared by reacting a compound of formula (XIX) with a compound of formula (XXXI) under reductive amination conditions, as described in Scheme 1, step C.

Compounds of formula (XXIV) may be prepared according to the processes outlined in Scheme 4.

Scheme 4.

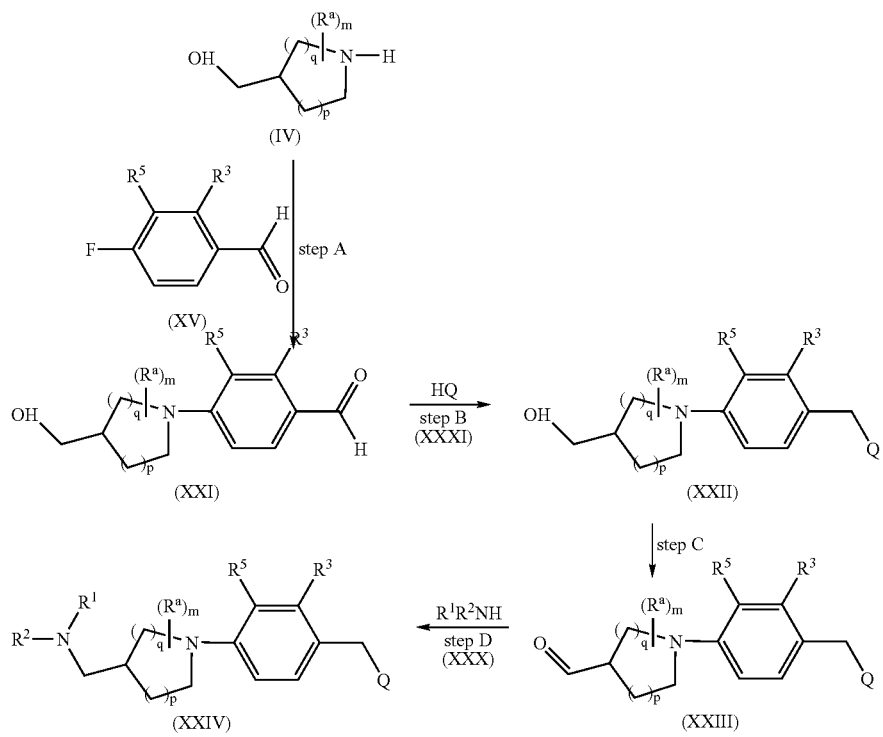

A compound of formula (XXIV) is prepared as outlined in Scheme 4 from a compound of formula (IV). A compound of formula (IV) is reacted with a compound of formula (XV) under nucleophilic aromatic substitution conditions, as described in Scheme 3, step A. A compound of formula (XXI) is reacted with a compound of formula (XXXI) under reductive amination conditions, as described in Scheme 1, step C. A compound of formula (XXIII) is prepared from a compound of formula (XXII) by reacting a compound of formula (XXII) with an oxidizing agent under alcohol oxidizing conditions. In a preferred embodiment, a compound of formula (XXII) is reacted with an oxidant such as DMSO in combination with oxalyl chloride in the presence of an organic base such as triethylamine in a solvent such as DCM at a temperature from −78° C. to room temperature. A compound of formula (XXIV) is obtained by reacting a compound of formula (XXIII) with a compound of formula (XXX) under reductive amination conditions, as described in Scheme 1, step C.

Compounds of formula (XXVI) may be prepared according to the processes outlined in Scheme 5.

Scheme 5.

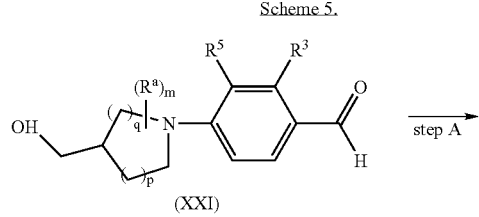

-continued

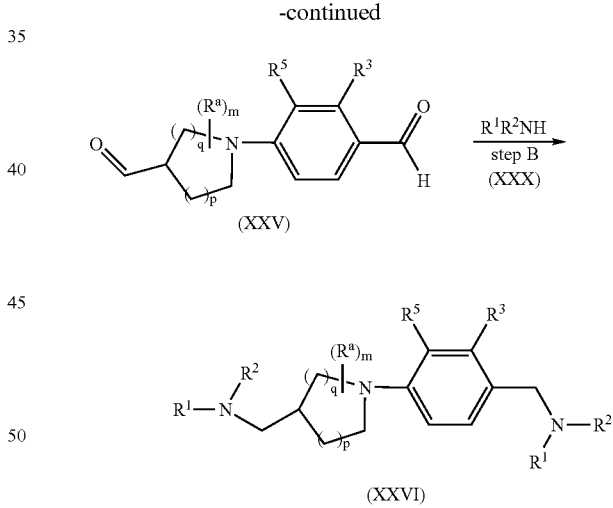

A compound of formula (XXVI) is prepared from a compound of formula (XXI) as shown in Scheme 5. A compound of formula (XXV) is prepared by reacting a compound of formula (XXI) under alcohol oxidation conditions as described in Scheme 4, step C. A compound of formula (XXVI) is prepared by reacting a compound of formula (XXV) with a compound of formula (XXX) under reductive amination conditions as described in Scheme 1, step C.

Compounds of formula (XXXIII) may be prepared according to the processes outlined in Scheme 6.

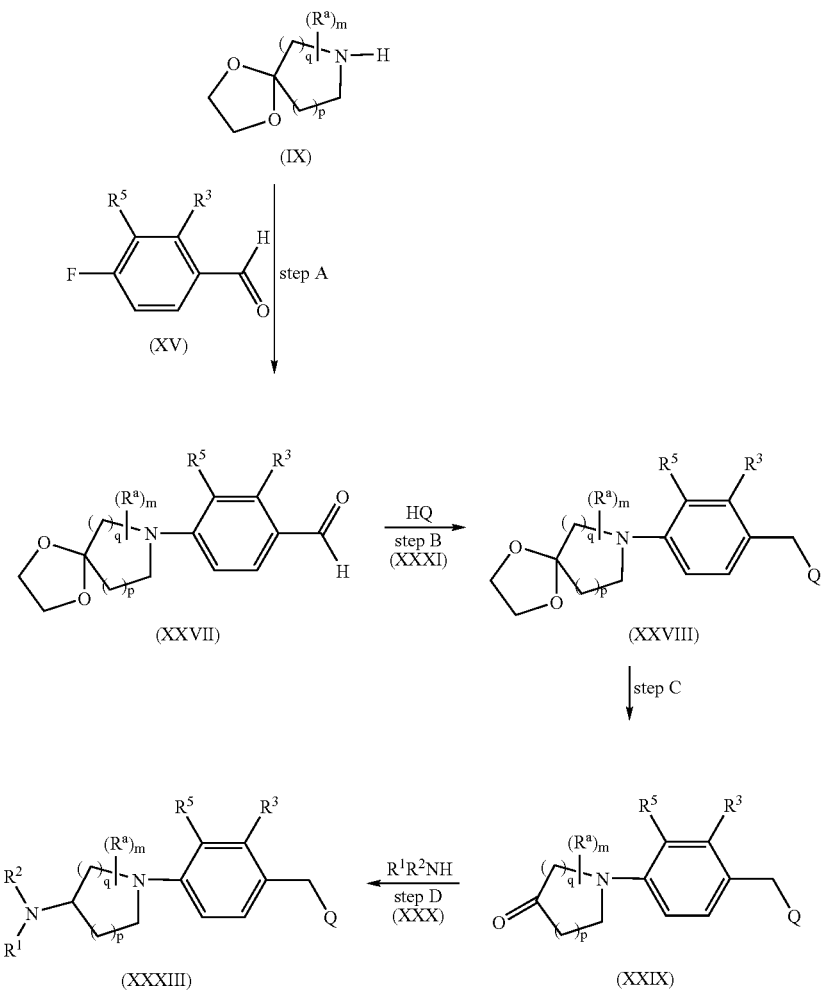

Scheme 6.

A compound of formula (XXXIII) is prepared as outlined in Scheme 6 from a compound of formula (IX). A compound of formula (XXVII) is prepared from a compound of formula (IX) by reacting a compound of formula (IX) with a compound of formula (XV) under nucleophilic, aromatic substitution conditions as described in Scheme 3, step A. A compound of formula (XXVIII) is prepared from a compound of formula (XXVII) by reacting a compound formula (XXVII) with a compound of formula (XXXI) under reductive amination conditions as described in Scheme 1, step C. A compound of formula (XXIX) is prepared from a compound of formula (XXVIII) by reacting a compound of formula (XXVIII) under ketal hydrolysis conditions as outlined in Scheme 2, step B. A compound of formula (XXXIII) is prepared by reacting a compound of formula (XXIX) with a compound of formula (XXX) under reductive amination conditions as described in Scheme 1, step C.

Compounds of formula (XXXIV) may be prepared according to the processes outlined in Scheme 7.

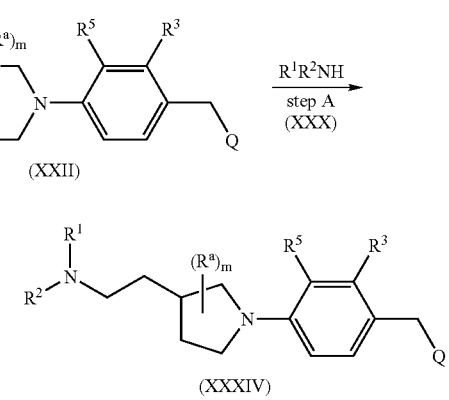

Scheme 7.

A compound of formula (XXXIV) is prepared from a compound of formula (XXII) as shown in Scheme 7. A compound of formula (XXXIV) is prepared by reacting a compound of formula (XXII) with a compound of formula (XXX) under rearranging, nucleophilic substitution conditions. In a preferred embodiment, a compound of formula (XXII) is reacted with a compound of formula (XXX) in the presence of a reagent capable of converting the hydroxyl functionality to a leaving group such as trimethylcyanomethylphosphonium iodide and a base such as N-ethyl-N,N-diisopropylamine in a solvent such as acetonitrile or propionitrile at a temperature from 0° C. to 100° C. In a particularly preferred embodiment, a compound of formula (XXII) is reacted with a compound of formula (XXX) in the presence of trimethylcyanomethylphosphonium iodide and N-ethyl-N,N-diisopropylamine in propionitrile at 90° C.

D. Formulation, Administration, and Therapy

The disclosed compounds, alone or in combination (with, for example, a histamine $H_1$ receptor antagonist), are useful for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof.

1. Formulation and Administration

The compounds or compositions of the invention may be formulated and administered to a subject by any conventional route of administration, including, but not limited to, intravenous, oral, subcutaneous, intramuscular, intradermal and parenteral administration. The quantity of the compound that is effective for treating each condition may vary, and can be determined by one of ordinary skill in the art.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts that may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Thus, representative pharmaceutically acceptable salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound that may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The present invention also provides pharmaceutical compositions comprising one or more compounds of this invention in association with a pharmaceutically acceptable carrier and optionally additional pharmaceutical agents such as $H_1$ antagonists or SSRIs. Preferably these compositions are in unit dosage forms such as pills, tablets, caplets, capsules (each including immediate release, timed release and sustained release formulations), powders, granules, sterile parenteral solutions or suspensions (including syrups and emulsions), metered aerosol or liquid sprays, drops, ampoules, autoinjector devices or suppositories; for oral, parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid pre-formulation composition containing a homogeneous mixture of a compound of the present invention, or a pharmaceutically acceptable salt thereof. When referring to these pre-formulation compositions as homogeneous, it is meant that the active ingredient is dispersed evenly throughout the composition so that the composition may be readily subdivided into equally effective dosage forms such as tablets, pills and capsules. This solid pre-formulation composition is then subdivided into unit dosage forms of the type described above containing from 5 to about 1000 mg of the active ingredient of the present invention. Examples include 5 mg, 7 mg, 10 mg, 15 mg, 20 mg, 35 mg, 50 mg, 75 mg, 100 mg, 120 mg, 150 mg, and so on. The tablets or pills of the disclosed compositions can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the compounds and compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolyl-ysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment is required.

The daily dosage of the products may be varied over a wide range from 1 to 1,000 mg per adult human per day. For oral administration, the compositions are preferably provided in the form of tablets containing 1.0, 5.0, 10.0, 15.0, 25.0, 50.0, 100, 250 and 500 milligrams of the active ingredient for the symptomatic adjustment of the dosage to the subject to be treated. An effective amount of the drug is ordinarily supplied at a dosage level of from about 0.01 mg/kg to about 20 mg/kg of body weight per day. Preferably, the range is from about 0.02 mg/kg to about 10 mg/kg of body weight per day, and especially from about 0.05 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

2. Combination Therapy

The disclosed compounds are useful in combination with other therapeutic agents, including $H_1$ receptor antagonists, $H_2$ receptor antagonists, and neurotransmitter modulators such as SSRIs and non-selective serotonin re-uptake inhibitors (NSSRIs).

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that inhibits in a subject the onset or progression of a disorder as being sought by a researcher, veterinarian, medical doctor or other clinician, the delaying of which disorder is mediated, at least in part, by the modulation of one or more histamine receptors. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together. Combinations of three or more drugs are analogously possible. Methods of combination therapy include co-administration of a single formulation containing all active agents; essentially contemporaneous administration of more than one formulation; and administration of two or more active agents separately formulated.

E. EXAMPLES

In order to illustrate the invention, the following examples are included. These examples do not limit the invention. They are only meant to suggest a method of practicing the invention. Those skilled in the art may find other methods of practicing the invention, which are obvious to them. However, those methods are deemed to be within the scope of this invention.

Protocol for Preparative Reversed-Phase HPLC

Gilson®
Column: YMC-Pack ODS-A, 5 μm, 75×30 mm
Flow rate: 25 mL/min
Detection: λ=220 & 254 nm
Gradient (acetonitrile/water, 0.05% trifluoroacetic acid)
1) 0.0 min 15% acetonitrile/85% water
2) 20.0 min 99% acetonitrile/1% water Protocol for HPLC (Reversed-Phase)

Hewlett Packard Series 1100
Column: Agilent ZORBAX® Bonus RP, 5 μm, 4.6×250 mm
Flow rate: 1 mL/min
Detection: λ=220 & 254 nm
Gradient (acetonitrile/water, 0.05% trifluoroacetic acid)
1) 0.0 min 1% acetonitrile/99% water
2) 20.0 min 99% acetonitrile/1% water Mass spectra were obtained on an Agilent series 1100 MSD using electrospray ionization (ESI) in either positive or negative modes as indicated.

Thin-layer chromatography was performed using Merck silica gel 60 $F_{254}$ 2.5 cm×7.5 cm 250 μm or 5.0 cm×10.0 cm 250 μm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone.

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration).

Example 1

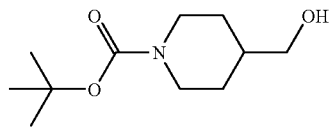

4-Hydroxymethyl-piperidine-1-carboxylic Acid Tert-butyl Ester

To a solution of 4-piperidinemethanol (37.2 g) in dichloromethane (DCM, 300 mL) was added di-tert-butyl dicarbonate (70.5 g) in several portions. The resulting mixture was stirred at room temperature overnight. The reaction mixture was diluted with DCM (700 mL), and washed with water (200 mL), saturated ammonium chloride (200 mL) and brine (200 mL). The combined extracts were dried (MgSO$_4$) and concentrated under reduced pressure, giving the title compound as a white solid (69.5 g).

Example 2

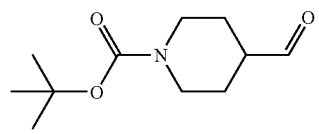

4-Formyl-piperidine-1-carboxylic Acid Tert-butyl Ester

To a mixture of the product of Example 1 (23.1 g), 4-methylmorpholine N-oxide (NMO, 18.9 g) and 4A molecular sieves (53.5 g) in DCM (214 mL) was added tetrapropylammonium perruthenate (TPAP, 1.9 g) portionwise at room temperature. The reaction mixture was stirred at room temperature for 1 h and filtered through a pad of silica gel. Evaporation of solvent gave the title compound as a light yellow oil (15.0 g).

Example 3

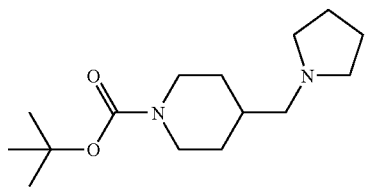

4-Pyrrolidin-1-ylmethyl-piperidine-1-carboxylic Acid Tert-butyl Ester

To a solution of the product of Example 2 (2.0 g) in DCM (40 mL) was added pyrrolidine (1.0 g) followed by sodium triacetoxyborohydride (2.8 g). The resulting mixture was stirred overnight, and treated with 10% NaOH (20 mL). The resulting mixture was extracted with DCM (300 mL). The combined extracts were washed with water (50 mL) and brine (50 mL), dried (MgSO$_4$), and concentrated under reduced pressure to give the title compound as a light pink-brown oil (2.4 g).

Example 4

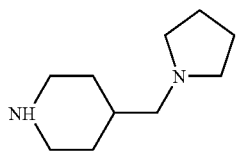

4-Pyrrolidin-1-ylmethyl-piperidine

To a solution of the product of Example 3 (2.4 g) in dioxane (30 mL) was added 4 N HCl in dioxane (30 mL). The resulting mixture was stirred at room temperature overnight, concentrated, and treated with 10% NaOH (50 mL). The resulting mixture was extracted with DCM (2×100 mL). The combined extracts were washed with water (30 mL) and brine (30 mL), and concentrated under reduced pressure to give the title compound as a brown-yellow oil (0.81 g).

Example 5

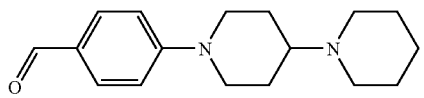

4-{1,4'}Bipiperidinyl-1'-yl-benzaldehyde

A mixture of 4-fluorobenzaldehyde (1 mL), {1,4'}bipiperidinyl (829.6 mg), and potassium carbonate (0.72 g) in DMF (3 mL) was heated to 100° C. for 6 h. The cooled reaction mixture was poured into water (200 mL) and then extracted with DCM. Removal of the solvent and chromatography of the residue on silica gel (1-7% 2 M methanolic ammonia/DCM) gave the title compound (838.3 mg).

Example 6

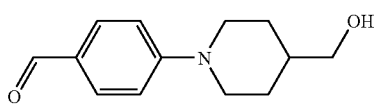

4-(4-Hydroxymethyl-piperidin-1-yl)-benzaldehyde

A suspension of 4-fluorobenzaldehyde (4.3 mL), 4-hydroxymethylpiperidine (4.8 g), and cesium carbonate (26 g) in DMF (80 mL) was heated to 100° C. for 24 h and cooled to room temperature. Water (400 mL) was added, and the resulting precipitate was collected by filtration to give the title compound as a tan amorphous powder (4.1 g).

The compounds of Example 7 through Example 9 were prepared according to the procedure of Example 6 from the specified fluorobenzaldehde and secondary amine.

Example 7

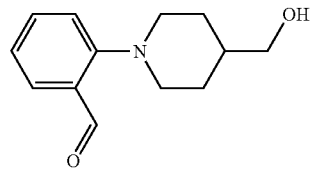

2-(4-Hydroxymethyl-piperidin-1-yl)-benzaldehyde

Prepared from 2-fluorobenzaldehyde and 4-hydroxymethylpiperidine.

Example 8

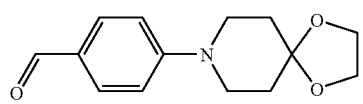

4-(1,4-Dioxa-8-aza-spiro{4,5}dec-8-yl)-benzaldehyde

Prepared from 4-fluorobenzaldehyde and 1,4-dioxa-8-aza-spiro{4.5}decane.

Example 9

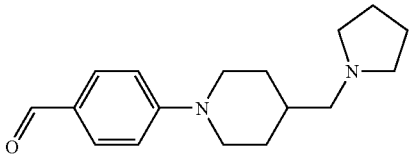

4-(4-Pyrrolidin-1-ylmethyl-pieridin-1-yl)-benzaldehyde

Prepared from 4-fluorobenzaldehyde and the product of Example 4.

Example 10

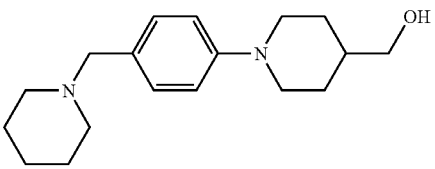

{1-(4-Piperidin-1-ylmethyl-phenyl)-piperidin-4-yl}-methanol

A solution of the product of Example 6 (1.3 g) and piperidine (0.70 mL) in DCM (11 mL) was treated with sodium triacetoxyborohydride (1.9 g). After 16 h, the resulting mixture was treated with 10% aqueous potassium hydroxide (10 mL). The aqueous phase was extracted with DCM (3×10 mL), and the combined organic phases were dried (MgSO₄), and concentrated under reduced pressure, giving the title compound as a white waxy solid (1.5 g).

The compounds of Example 11 through Example 14 were prepared according to the procedure of Example 10, using the specified aldehydes and amines.

Example 11

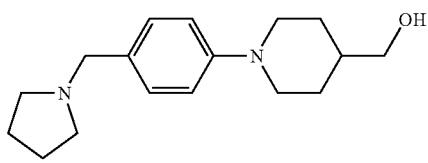

{1-(4-Pyrrolidin-1-ylmethyl-phenyl)-piperidin-4-yl}-methanol

Prepared from the product of Example 6 and pyrrolidine.

Example 12

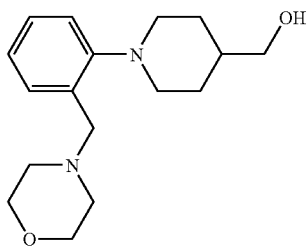

{1-(2-Morpholin-4-ylmethyl-phenyl)-piperidin-4-yl}-methanol

Prepared from the product of Example 7 and morpholine.

Example 13

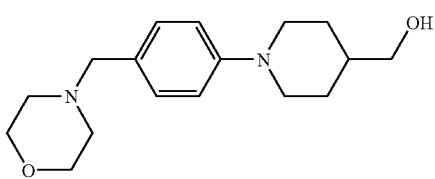

{1-(4-Morpholin-4-ylmethyl-phenyl)-piperidin-4-yl}-methanol

Prepared from the product of Example 6 and morpholine.

Example 14

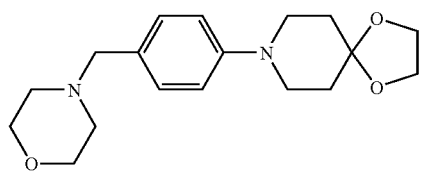

8-(4-Morpholin-4-ylmethyl-phenyl)-1,4-dioxa-8-aza-spiro{4,5}decane

Prepared from the product of Example 8 and morpholine.

Example 15

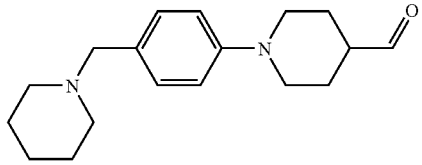

1-(4-Piperidin-1-ylmethyl-phenyl)-piperidine-4-carbaldehyde A solution of oxalyl chloride (1.0 mL) in DCM (4 mL) was cooled in a −78° C. bath and treated with DMSO (0.17 mL). After 5 min, a solution of the product of Example 10 in DCM (2 mL) was added dropwise. After 30 min, triethylamine (0.59 mL) was added, and the reaction mixture was allowed to warm to room temperature. Water (2 mL) was added, and the resulting mixture was extracted with DCM (3×3 mL). The combined extracts were dried (MgSO$_4$) and concentrated under reduced pressure, giving the title compound, which was used without further purification.

The compounds of Example 16 through Example 18 were prepared according to the procedure of Example 15 using the specified alcohol.

Example 16

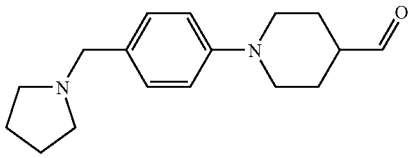

1-(4-Pyrrolidin-1-ylmethyl-phenyl)-piperidine-4-carbaldehyde

Prepared from the product of Example 11.

Example 17

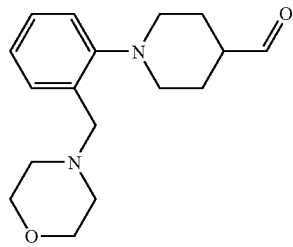

1-(2-Morpholin-4-ylmethyl-phenyl)-piperidine-4-carbaldehyde

Prepared from the product of Example 12.

Example 18

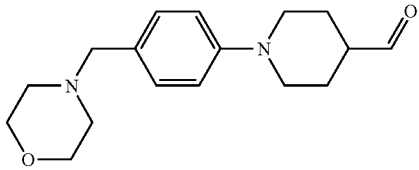

1-(4-Morpholin-4-ylmethyl-phenyl)-piperidine-4-carbaldehyde

Prepared from the product of Example 13.

Example 19

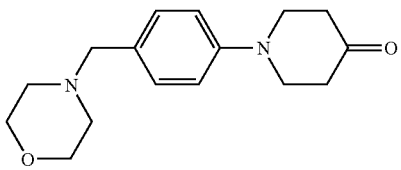

1-(4-Morpholin-4-ylmethyl-phenyl)-piperidin-4-one

The product of Example 14 (4.5 g) was treated with 6 M HCl (50 mL), heated to 100° C. for 90 min, and then cooled to room temperature. The resulting solution was basified with 10% aqueous NaOH to pH 11, and extracted with DCM (3×5 mL). The combined extracts were dried (MgSO$_4$), and concentrated under reduced pressure, giving the title compound as a brown gummy solid (4.3 g).

Example 20

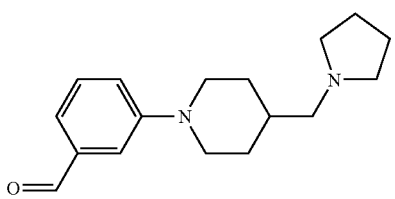

3-(4-Pyrrolidin-1-ylmethyl-piperidin-1-yl)-benzaldehyde

To a mixture of 3-formylphenylboronic acid (2.5 g) and piperidine (1.4 g) in DCM (200 mL) was added 4A molecular sieves (5 g) and copper(II) acetate (1.5 g) sequentially. The reaction mixture was stirred at room temperature for four days, filtered through a pad of Celite®, and concentrated under reduced pressure. Purification of the residue by silica gel chromatography (0-10% 2 M methanolic ammonia/DCM) afforded the title compound as a yellow solid (0.79 g).

Example 21

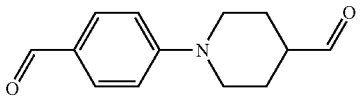

1-(4-Formyl-phenyl)-piperidine-4-carbaldehyde

Oxalyl chloride (2.5 mL, 2.0 M) was added to a cooled (−78° C.) solution of DMSO (0.7 mL) in DCM (3 mL). After 20 min a solution of the product from Example 6 (0.38 g) in DCM (3 mL) was added. This mixture was aged for an additional 20 min. Triethylamine was then added and the cold bath (CO$_2$/acetone) was removed. The mixture was allowed to reach ambient temperature. After 1 h the mixture was poured into water (100 mL) and extracted with DCM. Removal of the solvent gave the title compound (0.38 g), which was used without further purification.

Example 22

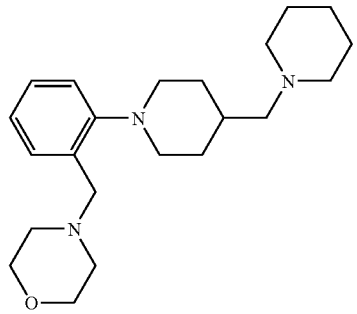

4-{2-(4-piperidin-1-ylmethyl-piperidin-1-yl)-benzyl}-morpholine

A solution of the product of Example 17 (288 mg) and piperidine (0.12 mL) in dichloroethane (DCE, 2 mL) was treated with sodium triacetoxyborohydride (297 mg). After 16 h, the resulting mixture was treated with 10% potassium hydroxide (2 mL), and extracted with DCM (2×2 mL). The combined extracts were dried (MgSO$_4$), and chromatographed on silica gel (0-8% 2 M methanolic ammonia/DCM), giving the title compound as a colorless oil (100 mg).

$^1$H NMR (400 MHz, CDCl$_3$): 7.42 (dd, J=7.6, 1.6 Hz, 1H), 7.21 (t, J=8.0, 1.8 Hz, 1H), 7.02 (ddd, J=8.0, 8.0, 1.0 Hz, 1H), 7.02 (ddd, J=7.4, 7.4, 1.2 Hz, 1H), 3.68 (t, J=4.7 Hz, 4H), 3.54 (s, 2H), 3.21-3.15 (m, 2H), 2.63 (ddd, J=11.7, 11.7, 2.2 Hz, 2H), 2.50-2.45 (br m, 4H), 2.41-2.37 (br m, 4H), 2.22 (d, J=7.0 Hz, 2H), 1.85-1.79 (m, 2H), 1.70-1.56 (m, 5H), 1.47-1.30 (m, 4H).

The compounds in Example 23 through Example 52 were prepared according to the procedure of Example 22 using the specified carbonyl compound and amine.

Example 23

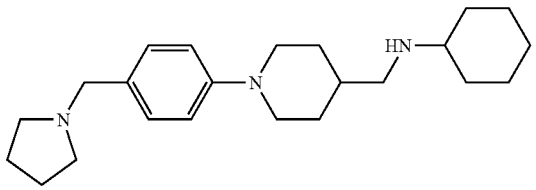

Cyclohexyl-{1-(4-pyrrolidin-1-ylmethyl-phenyl)-piperidin-4-ylmethyl}-amine

Prepared from the product of Example 16 and cyclohexylamine.

$^1$H NMR (400 MHz, CDCl$_3$): 7.19 (d, J=8.6 Hz, 2H), 6.90-6.87 (m, 2H), 3.66 (d, J=12.2 Hz, 2H), 3.52 (s, 2H), 2.71-2.64 (m, 2H), 2.55 (d, J=6.7 Hz, 4H), 2.49-2.43 (m, 4H), 2.42-2.36 (m, 1H), 1.90-1.53 (m, 11H), 1.41-1.01 (m, 8H).

Example 24

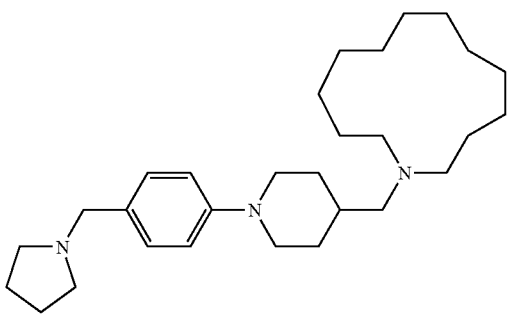

1-{1-(4-Pyrrolidin-1-ylmethyl-phenyl)-piperidin-4-ylmethyl}-azacyclotridecane

Prepared from the product of Example 16 and dodecamethyleneamine.

$^1$H NMR (400 MHz, CDCl$_3$): 7.19 (d, J=8.6 Hz, 2H), 6.89 (d, J=8.6 Hz, 2H), 3.65 (d, J=12.3 Hz, 2H), 3.53 (s, 2H), 2.71-2.63 (m, 2H), 2.49 (br s, 4H), 2.32-2.31 (m, 4H), 2.15 (d, J=6.9 Hz, 2H), 1.90 (d, J=13.0 Hz, 2H), 1.79-1.73 (m, 4H), 1.63-1.24 (m, 23H).

Example 25

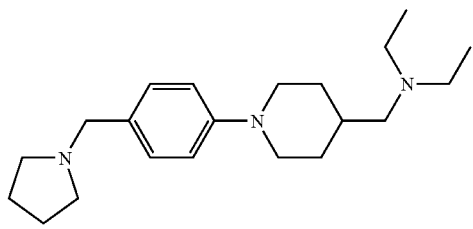

Diethyl-{1-(4-pyrrolidin-1-ylmethyl-phenyl)-piperidin-4-ylmethyl}-amine

Prepared from the product of Example 16 and diethylamine.

$^1$H NMR (400 MHz, CDCl$_3$): 7.19 (d, J=8.5 Hz, 2H), 6.89 (d, J=8.6 Hz, 2H), 3.65 (d, J=12.3 Hz, 2H), 3.52 (s, 2H), 2.70-2.64 (m, 2H), 2.53-2.48 (m, 8H), 2.25 (d, J=7.0 Hz, 2H), 1.86 (d, J=12.5 Hz, 2H), 1.78-1.73 (m, 4H), 1.58-1.51 (m, 1H), 1.36-1.26 (m, 2H), 1.01 (t, J=7.1 Hz, 6H).

Example 26

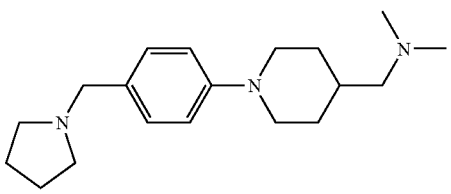

Dimethyl-{1-(4-pyrrolidin-1-ylmethyl-phenyl)-piperidin-4-ylmethyl}-amine

Prepared from the product of Example 16 and dimethylamine hydrochloride.

$^1$H NMR (400 MHz, CDCl$_3$): 7.19 (d, J=8.5 Hz, 2H), 6.89 (d, J=8.6 Hz, 2H), 3.66 (d, J=12.3 Hz, 2H), 3.53 (s, 2H), 2.71-2.64 (m, 2H), 2.48 (br s, 4H), 2.22 (s, 6H), 2.15 (d, J=7.2 Hz, 2H), 1.85 (d, J=13.0 Hz, 2H), 1.80-1.73 (m, 4H), 1.64-1.55 (m, 1H), 1.38-1.26 (m, 2H).

Example 27

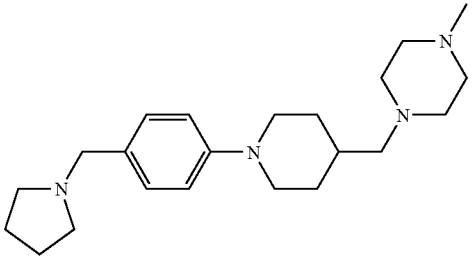

1-Methyl-4-{1-(4-pyrrolidin-1-ylmethyl-phenyl)-piperidin-4-ylmethyl}-piperazine

Prepared from the product of Example 16 and N-methylpiperazine.

$^1$H NMR (400 MHz, CDCl$_3$): 7.19 (d, J=8.5 Hz, 2H), 6.89 (d, J=8.5 Hz, 2H), 3.54 (s, 2H), 2.69-2.35 (m, 12H), 2.29 (s, 3H), 2.22 (d, J=7.2 Hz, 2H), 1.87-1.59 (m, 9H), 1.38-1.26 (m, 2H).

Example 28

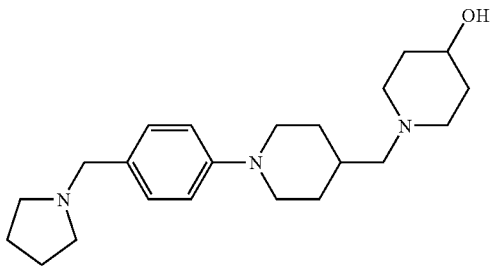

1-{1-(4-Pyrrolidin-1-ylmethyl-phenyl)-piperidin-4-ylmethyl}-piperidin-4-ol

Prepared from the product of Example 16 and 4-hydroxypiperidine.

$^1$H NMR (400 MHz, CDCl$_3$): 7.20 (d, J=8.5 Hz, 2H), 6.89 (d, J=8.5 Hz, 2H), 3.71-3.64 (m, 3H), 3.54 (s, 2H), 2.75-2.63 (m, 4H), 2.50 (br s, 4H), 2.19 (d, J=7.8 Hz, 2H), 2.09 (t, J=10.1 Hz, 2H), 1.91-1.54 (m, 12H), 1.38-1.24 (m, 3H).

Example 29

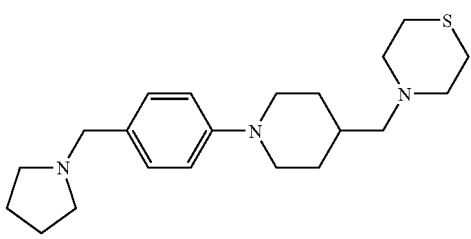

4-{1-(4-Pyrrolidin-1-ylmethyl-phenyl)-piperidin-4-ylmethyl}-thiomorpholine

Prepared from the product of Example 16 and thiomorpholine.

$^1$H NMR (400 MHz, CDCl$_3$): 7.20 (d, J=8.8 Hz, 2H), 6.89 (d, J=8.6 Hz, 2H), 3.65 (d, J=12.3 Hz, 2H), 3.53 (s, 2H), 3.14-3.10 (m, 1H), 2.71-2.58 (m, 10H), 2.52-2.46 (m, 4H), 2.22 (d, J=7.0 Hz, 2H), 1.87-1.74 (m, 6H), 1.68-1.56 (m, 2H), 1.31 (ddd, J=12.2 Hz, 12.2 Hz, 3.9 Hz, 2H).

Example 30

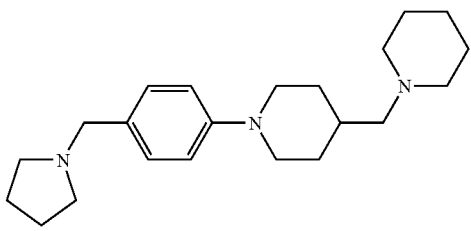

1-{1-(4-Pyrrolidin-1-ylmethyl-phenyl)-piperidin-4-ylmethyl}-piperidine

Prepared from the product of Example 16 and piperidine.

$^1$H NMR (400 MHz, CDCl$_3$): 7.19 (d, J=8.6 Hz, 2H), 6.89 (d, J=8.6 Hz, 2H), 3.65 (d, J=12.1 Hz, 2H), 3.53 (s, 2H), 2.65 (ddd, J=12.2, 12.2, 2.3 Hz, 2H), 2.50-2.45 (m, 4H), 2.37-2.29 (br s, 2H), 2.16 (d, J=7.3 Hz, 2H), 1.88-1.74 (m, 6H), 1.68-1.53 (m, 7H), 1.46-1.39 (m, 2H), 1.33 (dddd, J=12.2, 12.2, 12.2, 3.8 Hz, 2H).

Example 31

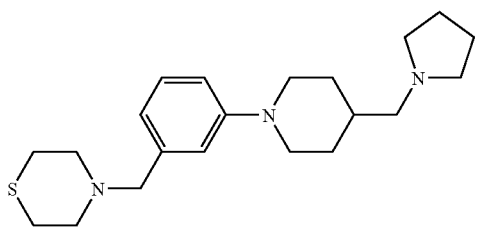

4-{1-(4-Pyrrolidin-1-ylmethyl-phenyl)-pieridin-4-ylmethyl}-morpholine

Prepared from the product of Example 16 and morpholine.

$^1$H NMR (400 MHz, CDCl$_3$): 7.20 (d, J=8.6 Hz, 2H), 6.89 (d, J=8.6 Hz, 2H), 3.71 (t, J=4.7 Hz, 4H), 3.66 (d, J=12.2 Hz, 2H), 3.53 (s, 2H), 2.69-2.63 (m, 2H), 2.48 (br s, 4H), 2.43-2.41 (m, 4H), 2.22 (d, J=7.1 Hz, 2H), 1.86 (d, J=12.4 Hz, 2H), 1.78-1.73 (m, 4H), 1.67-1.59 (m, 1H), 1.39-1.29 (m, 2H).

Example 32

4-{3-(4-Pyrrolidin-1-ylmethyl-piperidin-1-yl)-benzyl}-thiomorpholine

Prepared from the product of Example 20 and thiomorpholine.

$^1$H NMR (400 MHz, CDCl$_3$): 7.21-7.17 (m, 1H), 6.90 (s, 1H), 6.85-6.76 (m, 2H), 3.69 (d, J=12.3 Hz, 2H), 3.46 (s, 2H), 2.71-2.66 (m, 10H), 2.50 (br s, 4H), 2.36 (d, J=7.1 Hz, 2H), 1.90 (d, J=12.8 Hz, 2H), 1.82-1.75 (m, 4H), 1.62-1.57 (m, 1H), 1.42-1.32 (m, 2H).

Example 33

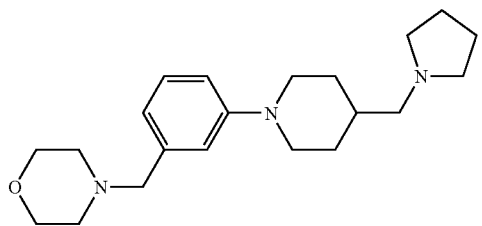

4-{3-(4-Pyrrolidin-1-ylmethyl-piperidin-1-yl)-benzyl}-morpholine

Prepared from the product of Example 20 and morpholine.

$^1$H NMR (400 MHz, CDCl$_3$): 7.21-7.17 (m, 1H), 6.92 (s, 1H), 6.85-6.78 (m, 2H), 3.72-3.67 (m, 6H), 3.45 (s, 2H), 2.72-2.65 (m, 2H), 2.49-2.44 (m, 8H), 2.36 (d, J=7.1 Hz, 2H), 1.90 (d, J=12.8 Hz, 2H), 1.82-1.75 (m, 4H), 1.67-1.58 (m, 1H), 1.42-1.32 (m, 2H).

Example 34

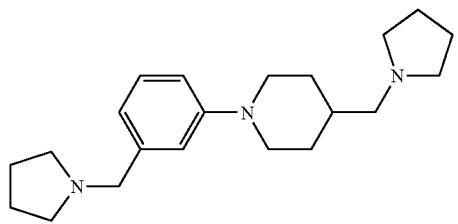

4-Pyrrolidin-1-ylmethyl-1-(3-pyrrolidin-1-ylmethyl-phenyl)-piperidine

Prepared from the product of Example 20 and pyrrolidine.

$^1$H NMR (400 MHz, CDCl$_3$): 7.20-7.16 (m, 1H), 6.93 (s, 1H), 6.84-6.78 (m, 2H), 3.69 (d, J=12.2 Hz, 2H), 3.57 (s, 2H), 2.71-2.64 (m, 2H), 2.50-2.49 (m, 8H), 2.35 (d, J=7.2 Hz, 2H), 1.88 (d, J=13.1 Hz, 2H), 1.79-1.57 (m, 9H), 1.41-1.25 (m, 2H).

Example 35

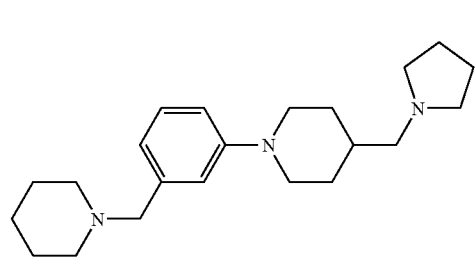

1-{3-(4-pyrrolidin-1-ylmethyl-piperidin-1-yl)-benzyl}-piperidine

Prepared from the product of Example 20 and piperidine.

$^1$H NMR (400 MHz, CDCl$_3$): 7.20-7.16 (m, 1H), 6.92 (s, 1H), 6.84-6.77 (m, 2H), 3.69 (d, J=12.3 Hz, 2H), 3.42 (s, 2H), 2.73-2.34 (m, 12H), 1.89 (d, J=12.9 Hz, 2H), 1.82-1.32 (m, 9H).

Example 36

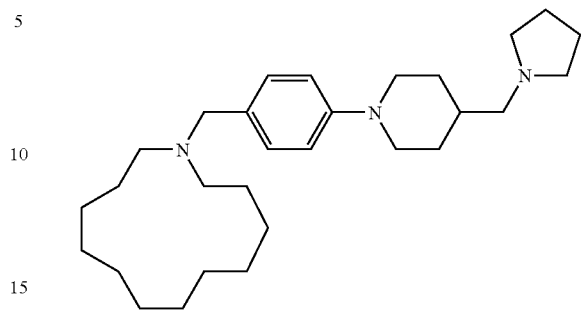

1-{4-(4-Pyrrolidin-1-ylmethyl-piperidin-1-yl)-benzyl}-azacyclotridecane

Prepared from the product of Example 9 and dodecamethyleneamine.

$^1$H NMR (400 MHz, CDCl$_3$): 7.19 (d, J=8.4 Hz, 2H), 6.89 (d, J=8.6 Hz, 2H), 3.67 (d, J=12.2 Hz, 2H), 3.39 (s, 2H), 2.69-2.63 (m, 4H), 2.49 (br s, 4H), 2.37-2.31 (m, 6H), 1.89 (d, J=12.1 Hz, 2H), 1.79-1.77 (m, 4H), 1.63-1.35 (m, 21H).

Example 37

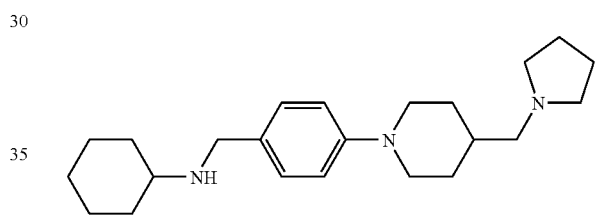

Cyclohexyl-{4-(4-pyrrolidin-1-ylmethyl-piperidin-1-yl)-benzyl}-amine

Prepared from the product of Example 9 and cyclohexylamine.

$^1$H NMR (400 MHz, CDCl$_3$): 7.18 (d, J=8.5 Hz, 2H), 6.90 (d, J=8.6 Hz, 2H), 3.71 (s, 2H), 3.66 (d, J=12.3 Hz, 2H), 2.69-2.63 (m, 2H), 2.50-2.46 (m, 5H), 2.35 (d, J=7.2 Hz, 2H), 1.90-1.59 (m, 11H), 1.39-1.12 (m, 8H).

Example 38

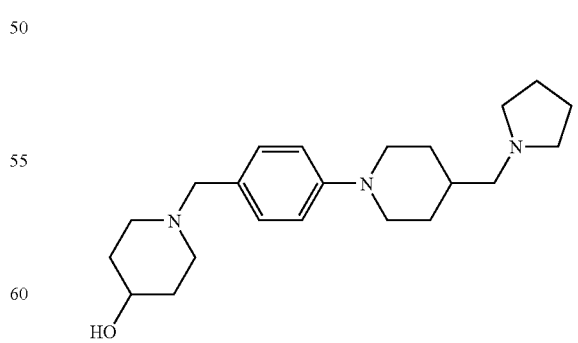

1-{4-(4-Pyrrolidin-1-ylmethyl-piperidin-1-yl)-benzyl}-piperidin-4-ol

Prepared from the product of Example 9 and 4-hydroxypiperidine.

¹H NMR (400 MHz, CDCl₃): 7.26-7.15 (m, 2H), 6.88 (d, J=8.5 Hz, 2H), 3.68-3.65 (m, 3H), 3.41 (s, 2H), 2.75-2.64 (m, 4H), 2.49-2.47 (m, 4H), 2.35 (d, J=7.1 Hz, 2H), 2.10 (t, J=9.0 Hz, 2H), 1.90-1.75 (m, 10H), 1.65-1.52 (m, 2H), 1.41-1.31 (m, 2H).

Example 39

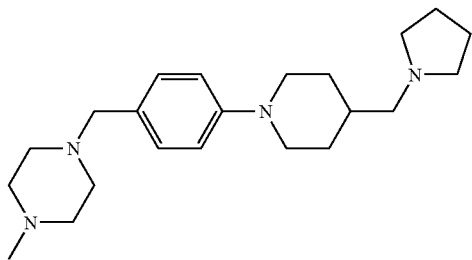

1-Methyl-4-{4-(4-pyrrolidin-1-ylmethyl-piperidin-1-yl)-benzyl}-piperazine

Prepared from the product of Example 9 and N-methylpiperazine.

¹H NMR (400 MHz, CDCl₃): 7.17 (d, J=8.5 Hz, 2H), 6.89 (d, J=8.6 Hz, 2H), 3.66 (d, J=12.2 Hz, 2H), 3.42 (s, 2H), 2.73-2.31 (m, 14H), 2.27 (s, 3H), 1.88 (br s, 4H), 1.82-1.75 (m, 4H), 1.65-1.57 (m, 1H), 1.41-1.31 (m, 2H).

Example 40

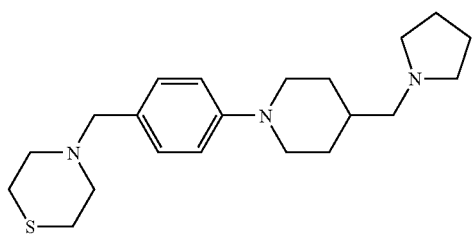

4-{4-(4-Pyrrolidin-1-ylmethyl-piperidin-1-yl)-benzyl}-thiomorpholine

Prepared from the product of Example 9 and thiomorpholine.

¹H NMR (400 MHz, CDCl₃): 7.15 (d, J=8.5 Hz, 2H), 6.89 (d, J=8.6 Hz, 2H), 3.67 (d, J=12.2 Hz, 2H), 3.43 (s, 2H), 2.73-2.59 (m, 10H), 2.49 (br s, 4H), 2.36 (d, J=7.2 Hz, 2H), 1.88 (d, J=13.3 Hz, 2H), 1.80-1.75 (m, 4H), 1.67-1.57 (m, 1H), 1.41-1.31 (m, 2H).

Example 41

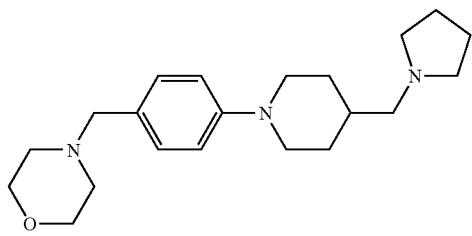

4-{4-(4-Pyrrolidin-1-ylmethyl-piperidin-1-yl)-benzyl}-morpholine

Prepared from the product of Example 9 and morpholine.

¹H NMR (400 MHz, CDCl₃): 7.18 (d, J=8.5 Hz, 2H), 6.89 (d, J=8.3 Hz, 2H), 3.71-3.65 (m, 6H), 3.40 (s, 2H), 2.73-2.61 (m, 2H), 2.49 (br s, 4H), 2.42 (bs, 4H), 2.36 (d, J=7.2 Hz, 2H), 1.88 (d, J=12.3 Hz, 2H), 1.80-1.75 (m, 4H), 1.66-1.57 (m, 1H), 1.41-1.31 (m, 2H).

Example 42

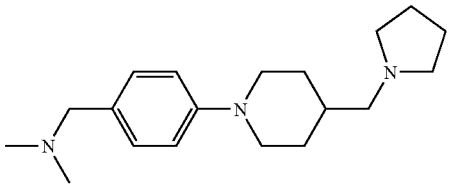

Dimethyl-{4-(4-pyrrolidin-1-ylmethyl-piperidin-1-yl)-benzyl}-amine

Prepared from the product of Example 9 and dimethylamine hydrochloride.

¹H NMR (400 MHz, CDCl₃): 7.16 (d, J=8.6 Hz, 2H), 6.91-6.88 (m, 2H), 3.67 (d, J=11.2 Hz, 2H), 3.33 (s, 2H), 2.70-2.64 (m, 2H), 2.52-2.47 (m, 4H), 2.35 (d, J=7.1 Hz, 2H), 2.21 (s, 6H), 1.89 (d, J=12.9 Hz, 2H), 1.82-1.76 (m, 4H), 1.65-1.56 (m, 1H), 1.42-1.32 (m, 2H).

Example 43

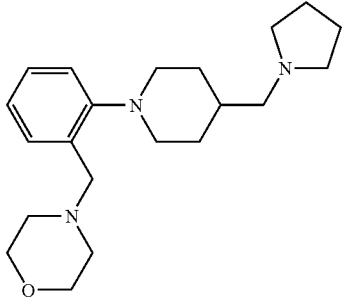

4-{2-(4-Pyrrolidin-1-ylmethyl-piperidin-1-yl)-benzyl}-morpholine

Prepared from the product of Example 17 and pyrrolidine.

¹H NMR (400 MHz, CDCl₃): 7.40 (dd, J=7.4, 1.6 Hz, 1H), 7.21 (dd, J=7.8, 1.5 Hz, 2H), 7.06 (dd, J=8.0, 1.0 Hz, 1H), 7.02 (dd, J=7.4, 1.7 Hz, 1H), 3.67 (t, J=4.7 Hz, 4H), 3.54 (s, 2H), 3.24-3.17 (m, 2H), 2.64 (ddd, J=11.7, 11.7, 2.1 Hz, 2H), 2.55-2.45 (m, 8H), 2.40 (m, 7.3 Hz, 2H), 1.90-1.77 (m, 6H), 1.67-1.55 (m, 1H), 1.45-1.33 (m, 2H).

Example 44

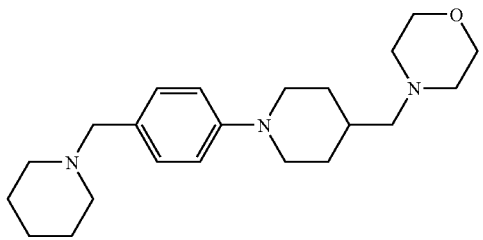

4-{1-(4-Piperidin-1-ylmethyl-phenyl)-piperidin-4-ylmethyl}-morpholine

Prepared from the product of Example 15 and morpholine.

$^1$H NMR (400 MHz, CDCl$_3$): 7.18 (d, J=8.5 Hz, 2H), 6.88 (d, J=8.6 Hz, 2H), 3.71 (t, J=4.7 Hz, 4H), 3.66 (d, J=12.3 Hz, 2H), 3.39 (s, 2H), 2.69-2.63 (m, 2H), 2.43-2.41 (m, 4H), 2.36 (br s, 4H), 2.22 (d, J=7.2 Hz, 2H), 1.85 (d, J=12.7 Hz, 2H), 1.66-1.53 (m, 5H), 1.42-1.29 (m, 4H).

Example 45

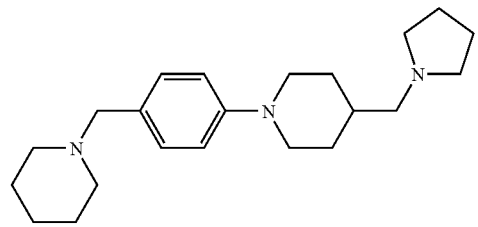

1-{4-(4-Pyrrolidin-1-ylmethyl-piperidin-1-yl)-benzyl}-piperidine

Prepared from the product of Example 15 and pyrrolidine.

$^1$H NMR (400 MHz, CDCl$_3$): 7.17 (d, J=8.6 Hz, 2H), 6.88 (d, J=8.8 Hz, 2H), 3.66 (d, J=12.3 Hz, 2H), 3.39 (s, 2H), 2.66 (ddd, J=12.2, 12.2, 2.5 Hz, 2H), 2.51-2.46 (m, 4H), 2.37-2.31 (m, 6H), 1.91-1.85 (m, 2H), 1.81-1.75 (m, 4H), 1.65-1.52 (m, 5H), 1.45-1.31 (m, 4H).

Example 46

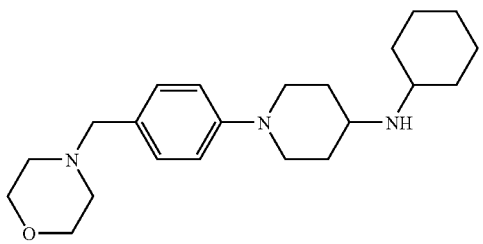

Cyclohexyl-{1-(4-morpholin-4-ylmethyl-phenyl)-piperidin-4-yl}-amine

Prepared from the product of Example 18 and cyclohexylamine.

$^1$H NMR (400 MHz, CDCl$_3$): 7.17 (d, J=8.6 Hz, 2H), 6.87 (d, J=8.8 Hz, 2H), 3.71-3.61 (m, 6H), 3.40 (s, 2H), 2.78-2.70 (m, 3H), 2.65-2.55 (m, 1H), 2.44-2.38 (m, 4H), 1.99-1.83 (m, 4H), 1.77-1.70 (m, 2H), 1.66-1.59 (m, 1H), 1.51-1.39 (m, 2H), 1.32-1.01 (m, 6H).

Example 47

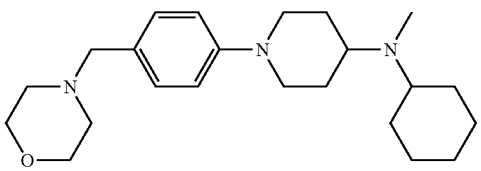

Cyclohexyl-methyl-{1-(4-morpholin-4-ylmethyl-phenyl)-piperidin-4-yl}-amine

Prepared from the product of Example 18 and N-methyl-N-cyclohexylamine.

$^1$H NMR (400 MHz, CDCl$_3$): 7.19 (d, J=8.8 Hz, 2H), 6.88 (d, J=8.8 Hz, 2H), 3.75-3.67 (m, 6H), 3.41 (s, 2H), 2.73-2.53 (m, 4H), 2.45-2.38 (m, 4H), 2.28 (s, 3H), 1.89-1.59 (m, 9H), 1.35-1.19 (m, 4H), 1.16-1.04 (m, 1H).

Example 48

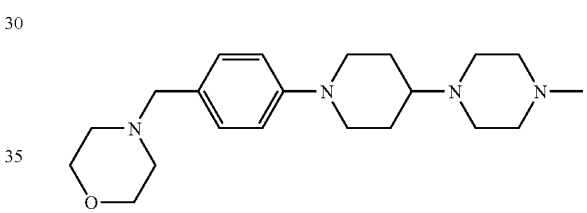

4-{4-{4-(4-Methyl-piperazin-1-yl)-piperidin-1-yl}-benzyl}-morpholine

Prepared from the product of Example 19 and N-methylpiperazine.

$^1$H NMR (400 MHz, CDCl$_3$): 7.17 (d, J=8.6 Hz, 2H), 6.87 (d, J=8.6 Hz, 2H), 3.76-3.66 (m, 6H), 3.40 (s, 2H), 2.69 (ddd, J=12.3, 12.3, 2.3 Hz, 2H), 2.65-2.45 (m, 6H), 2.44-2.31 (m, 7H), 2.29 (s, 3H), 1.97-1.90 (m, 2H), 1.72-1.60 (m, 2H).

Example 49

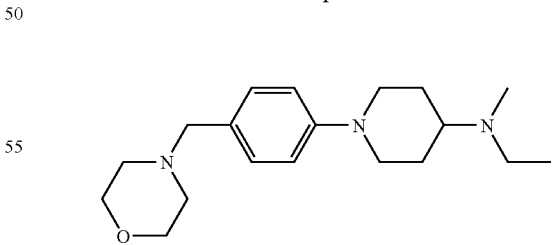

Ethyl-methyl-{1-(4-morpholin-4-ylmethyl-phenyl)-piperidin-4-yl}-amine

Prepared from the product of Example 19 and N-methylethylamine.

$^1$H NMR (400 MHz, CDCl$_3$): 7.18 (d, J=8.8 Hz, 2H), 6.88 (d, J=8.8 Hz, 2H), 3.76-3.67 (m, 6H), 3.49 (s, 3H), 3.41 (s, 2H), 2.68 (ddd, J=12.3, 12.3, 2.4 Hz, 2H), 2.57 (q, J=7.3 Hz, 2H), 2.54-2.46 (m, 1H), 2.45-2.40 (m, 4H), 1.90-1.84 (m, 2H), 1.74-1.62 (m, 2H), 1.08 (t, J=7.2 Hz, 3H).

Example 50

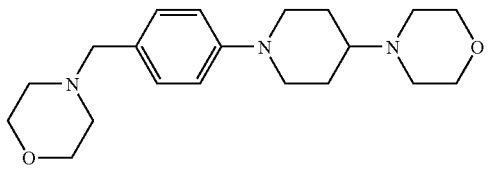

4-{1-(4-Morpholin-4-ylmethyl-phenyl)-piperidin-4-yl}-morpholine

Prepared from the product of Example 19 and morpholine.

$^1$H NMR (400 MHz, CDCl$_3$): 7.19 (d, J=8.6 Hz, 2H), 6.89 (d, J=8.8 Hz, 2H), 3.76-3.67 (m, 10H), 3.41 (s, 2H), 2.71 (ddd, J=12.2, 12.2, 2.4 Hz, 2H), 2.61-2.56 (m, 4H), 2.45-2.39 (m, 4H), 2.36-2.27 (m, 1H), 1.98-1.90 (m, 2H), 1.71-1.60 (m, 2H).

Example 51

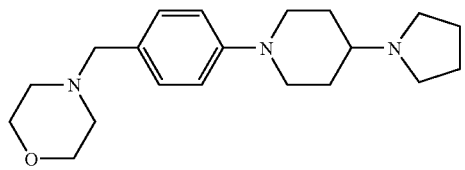

4-{4-(4-Pyrrolidin-1-yl-pieridin-1-yl)-benzyl}-morpholine

Prepared from the product of Example 19 and pyrrolidine.

$^1$H NMR (400 MHz, CDCl$_3$): 7.17 (d, J=8.6 Hz, 2H), 6.88 (d, J=8.6 Hz, 2H), 3.71-3.64 (m, 6H), 3.40 (s, 2H), 2.73 (ddd, J=12.3, 2.5 Hz, 2H), 2.62-2.57 (m, 4H), 2.44-2.37 (m, 4H), 2.15-2.06 (m, 1H), 2.02-1.95 (m, 2H), 1.82-1.77 (m, 4H), 1.72-1.61 (m, 2H).

Example 52

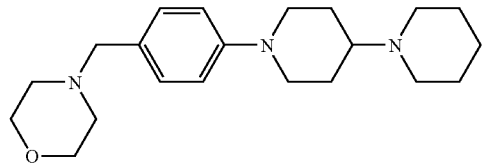

1'-(4-Morpholin-4-ylmethyl-phenyl)-{1,4'}bipiperidinyl

Prepared from the product of Example 19 and piperidine.

$^1$H NMR (400 MHz, CDCl$_3$): 7.17 (d, J=8.8 Hz, 2H), 6.88 (d, J=8.8 Hz, 2H), 3.77-3.67 (m, 6H), 3.41 (s, 2H), 2.67 (ddd, J=12.3, 12.3, 2.4 Hz, 2H), 2.56-2.51 (m, 4H), 2.44-2.33 (m, 5H), 1.94-1.87 (m, 2H), 1.75-1.57 (m, 6H), 1.48-1.41 (m, 2H).

Example 53

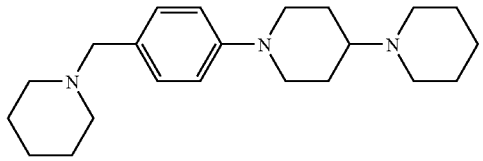

1'-(4-Piperidin-1-ylmethyl-phenyl)-{1,4'}bipiperidinyl

Prepared from the product of Example 5 and piperidine.

$^1$H NMR (400 MHz, CDCl$_3$): 7.18 (m, 2H), 6.88 (m, 2H), 3.65 (m, 2H), 3.51 (s, 2H), 2.65 (m, 2H), 2.50-2.44 (m, 8H), 2.34 (d, J=7.1 Hz, 2H), 1.87 (br m, 2H), 1.81-1.71 (m, 8H), 1.65-1.53 (m, 1H), 1.41-1.30 (m, 2H).

Example 54

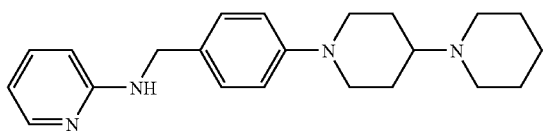

(4-{1,4'}Bipiperidinyl-1'-yl-benzyl)-pyridin-2-yl-amine

A solution of the product of Example 5 (109 mg), 2-aminopyridine (45 mg), and acetic acid (0.05 mL) in DCE (1 mL) was treated with sodium triacetoxyborohydride (127 mg). After 16 h, the resulting mixture was treated with 10% potassium hydroxide (1 mL), and extracted with DCM (2×1 mL). The combined organic phases were dried (MgSO$_4$) and chromatographed on silica gel (0-8% 2 M methanolic ammonia/DCM), giving the title compound (83 mg).

$^1$H NMR (400 MHz, CDCl$_3$): 8.10 (ddd, J=4.9, 1.8, 0.8 Hz, 1H), 7.39 (ddd, J=8.8, 7.0, 2.0 Hz, 1H), 7.23 (d, J=8.6 Hz, 2H), 6.90 (d, J=8.8 Hz, 2H), 6.57 (ddd, J=7.3, 5.1, 0.8 Hz, 1H), 6.37 (d, J=8.4 Hz, 1H), 4.77-4.71 (m, 1H), 4.39 (d, J=5.5 Hz, 2H), 3.76-3.70 (m, 2H), 2.68 (ddd, J=12.3, 12.3, 2.4 Hz, 2H), 2.56-2.51 (m, 4H), 2.42-2.34 (m, 1H), 1.94-1.87 (m, 2H), 1.74-1.56 (m, 6H), 1.47-1.41 (m, 2H).

The compounds of Example 55 through Example 59 were prepared according to the procedure of Example 54 using the specified carbonyl compound and aminoarene.

Example 55

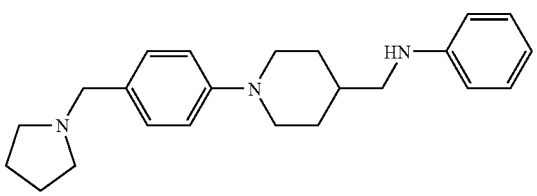

Phenyl-{1-(4-pyrrolidin-1-ylmethyl-phenyl)-piperidin-4-ylmethyl}-amine

Prepared from the product of Example 16 and aniline.

$^1$H NMR (400 MHz, CDCl$_3$): 7.21-7.16 (m, 4H), 6.89 (d, J=8.6 Hz, 2H), 6.71-6.61 (m, 3H), 3.75-3.67 (m, 3H), 3.53

(s, 2H), 3.08-3.06 (m, 2H), 2.72-2.65 (m, 2H), 2.48 (br s, 4H), 1.90 (d, J=12.3 Hz, 2H), 1.78-1.67 (m, 5H), 1.50-1.40 (m, 2H).

Example 56

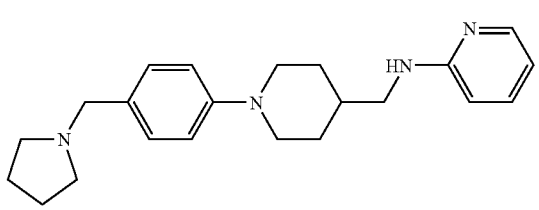

Pyridin-2-yl-{1-(4-pyrrolidin-1-ylmethyl-phenyl)-piperidin-4-ylmethyl}-amine

Prepared from the product of Example 16 and 2-aminopyridine.

$^1$H NMR (400 MHz, CDCl$_3$): 8.09-8.07 (m, 1H), 7.44-7.39 (m, 1H), 7.20 (d, J=8.6 Hz, 2H), 6.91-6.88 (m, 2H), 6.58-6.55 (m, 1H), 6.39 (d, J=8.5 Hz, 2H), 4.57 (brs, 1H), 3.69 (d, J=12.2 Hz, 2H), 3.53 (s, 2H), 3.22 (t, J=6.5 Hz, 2H), 2.72-2.65 (m, 2H), 2.50-2.47 (m, 4H), 1.92-1.70 (m, 5H), 1.50-1.40 (m, 2H).

Example 57

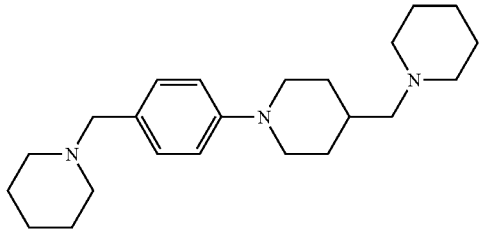

1-{1-(4-Piperidin-1-ylmethyl-phenyl)-piperidin-4-ylmethyl}-piperidine

A solution of the product of Example 21 (194.6 mg), piperidine (196 μL), and acetic acid (114 μL) in DCM (5 mL) was treated with sodium triacetoxyborohydride (570 mg). After 16 h, the resulting mixture was treated with 10% sodium hydroxide (10 mL), and the mixture was extracted with DCM (3×10 mL). The combined organic phases were dried (sodium sulfate) and concentrated under reduced pressure. Chromatography of the residue on silica gel (1-7% 2 M methanolic ammonia/DCM) gave the title compound (193.1 mg).

$^1$H NMR (400 MHz, CDCl$_3$): 7.16 (m, 2H), 6.87 (m, 2H), 3.73 (m, 2H), 3.39 (s, 2H), 2.70-2.65 (m, 2H), 2.57-2.49 (br m, 4H), 2.41-2.29 (br, 5H), 1.94-1.86 (br m, 2H), 1.75-1.51 (m, 10H), 1.48-1.37 (br m, 4H).

Example 58

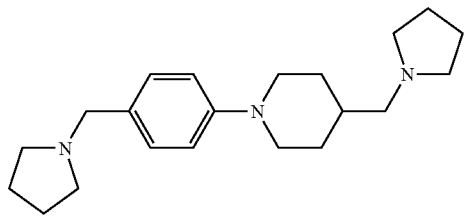

4-Pyrrolidin-1-ylmethyl-1-(4-pyrrolidin-1-ylmethyl-phenyl)-piperidine

A solution of the product of Example 21 (185.5 mg), pyrrolidine (160 μL), and acetic acid (114 μL) in DCM (5 mL) was treated with sodium triacetoxyborohydride (570 mg). After 16 h, the resulting mixture was treated with 10% sodium hydroxide (10 mL), and the mixture was extracted with DCM (3×10 mL). The combined organic phases were dried (sodium sulfate) and concentrated under reduced pressure. Chromatography of the residue on silica gel (1-7% 2 M methanolic ammonia/DCM) gave the title compound (114.1 mg).

$^1$H NMR (400 MHz, CDCl$_3$): 7.17 (m, 2H), 6.88 (m, 2H), 3.65 (m, 2H), 3.38 (s, 2H), 2.65 (m, 2H), 2.39-2.28 (br m, 8H), 2.16 (d, J=7.1 Hz, 2H) 1.84 (br m, 2H), 1.69-1.52 (m, 9H) 1.46-1.26 (m, 6H).

Example 59

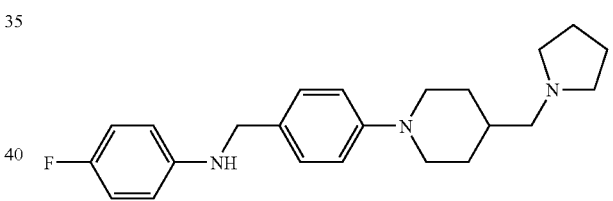

(4-Fluoro-phenyl)-{4-(4-pyrrolidin-1-ylmethyl-piperidin-1-yl)-benzyl}-amine

Prepared from the product of Example 9 and 4-fluoroaniline.

$^1$H NMR (400 MHz, CDCl$_3$): 7.23 (d, J=8.5 Hz, 2H), 6.92-6.84 (m, 4H), 6.58-6.55 (m, 2H), 4.17 (d, J=2.4 Hz, 2H), 3.80 (br s, 1H), 3.68 (d, J=12.3 Hz, 2H), 2.71-2.65 (m, 2H), 2.49 (br s, 4H), 2.35 (d, J=7.2 Hz, 2H), 1.88 (d, J=12.7 Hz, 2H), 1.82-1.77 (m, 4H), 1.65-1.57 (m, 1H), 1.42-1.31 (m, 2H).

Example 60

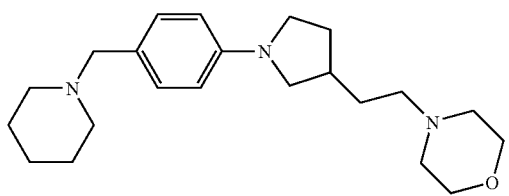

4-{2-{1-(4-Piperidin-1-ylmethyl-phenyl)-pyrrolidin-3-yl}-ethyl}-morpholine

A solution of the product of the product of Example 10 (144 mg), morpholine (0.05 mL), N-ethyl-N,N-diisopropylamine (0.17 mL), and trimethyl-(cyanomethyl)phosphonium iodide (243 mg) in propionitrile (1 mL) was heated in a 90° C. bath for 2 h. The resulting mixture was cooled to room temperature, treated with 10% aqueous potassium hydroxide (2 mL), and extracted with DCM (3×2 mL). The combined extracts were dried (MgSO$_4$) and chromatographed on silica gel (0-10% 2 M methanolic ammonia/DCM), giving the title compound as a yellow oil (113 mg).

$^1$H NMR (400 MHz, CDCl$_3$): 7.14 (d, J=8.4 Hz, 2H), 6.48 (d, J=8.6 Hz, 2H), 3.73 (t, J=4.7 Hz, 4H), 3.45 (dd, J=8.8, 7.6 Hz, 1H), 3.39 (s, 2H), 3.35 (ddd, J=9.0, 9.0, 3.1 Hz, 1H), 3.27 (ddd, J=8.8, 8.8, 7.0 Hz, 1H), 2.91 (dd, J=8.4, 8.4 Hz, 1H), 2.49-2.24 (m, 11H), 2.19-2.10 (m, 1H), 1.70-1.53 (m, 7H), 1.45-1.37 (m, 2H).

The compounds of Example 61 and Example 62 were prepared according to the procedure of Example 54 using the specified alcohol and secondary amine.

Example 61

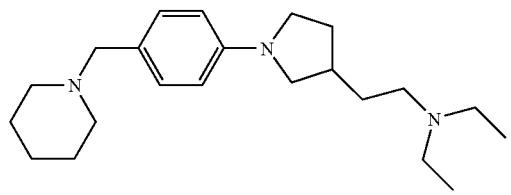

Diethyl-{2-{1-(4-piperidin-1-ylmethyl-phenyl)-pyrrolidin-3-yl}-ethyl}-amine

Prepared from the product of Example 10 and diethylamine.

$^1$H NMR (400 MHz, CDCl$_3$): 7.12 (d, J=8.4 Hz, 2H), 6.49 (d, J=8.6 Hz, 2H), 3.45 (dd, J=8.2, 8.0 Hz, 1H), 3.34 (ddd, J=9.0, 9.0, 3.1 Hz, 1H), 3.27 (ddd, J=9.0, 9.0, 6.9 Hz, 1H), 2.90 (dd, J=8.5, 8.5 Hz, 1H), 2.57-2.46 (m, 6H), 2.40-2.31 (m, 4H), 2.30-2.22 (m, 2H), 2.19-2.11 (m, 1H), 1.69-1.52 (m, 8H), 1.45-1.37 (m, 2H), 1.03 (t, J=7.1 Hz, 6H).

Example 62

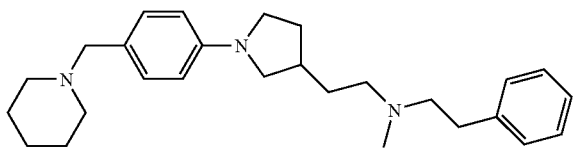

Methyl-phenethyl-{2-{1-(4-piperidin-1-ylmethyl-phenyl)-pyrrolidin-3-yl}-ethyl}-amine Prepared from the product of Example 10 and N-methylphenethylamine.

$^1$H NMR (400 MHz, CDCl$_3$): 7.31-7.26 (m, 2H), 7.23-7.19 (m, 3H), 7.14 (d, J=8.6 Hz, 2H), 6.48 (d, J=8.6 Hz, 2H), 3.43 (dd, J=8.8, 7.6 Hz, 1H), 3.34 (ddd, J=9.0, 9.0, 3.1 Hz, 1H), 3.26 (ddd, J=8.8, 8.8, 6.8 Hz, 1H), 2.89 (dd, J=8.5, 8.5 Hz, 1H), 2.81-2.76 (m, 2H), 2.65-2.59 (m, 2H), 2.46 (ddd, J=8.4, 7.3, 2.2 Hz, 2H), 2.46-2.32 (m, 4H), 2.32 (s, 3H), 2.31-2.20 (m, 2H), 2.17-2.08 (m, 1H), 1.68-1.52 (m, 8H), 1.45-1.37 (m, 2H).

The compounds of Example 63 through Example 67 were prepared according to the procedure of Example 6 using the specified fluorobenzaldehyde.

Example 63

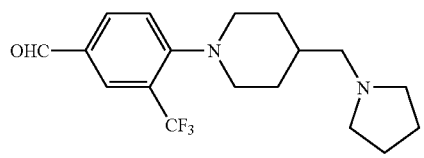

4-(4-Pyrrolidin-1-ylmethyl-piperidin-1-yl)-3-trifluoromethyl-benzaldehyde

Prepared from the product of Example 4 and 4-fluoro-3-trifluoromethyl-benzaldehyde.

Example 64

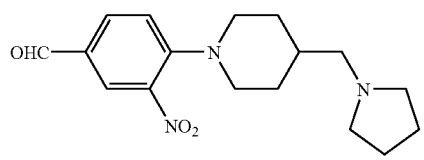

3-Nitro-4-(4-pyrrolidin-1-ylmethyl-piperidin-1-yl)-benzaldehyde

Prepared from the product of Example 4 and 4-fluoro-3-nitro-benzaldehyde.

Example 65

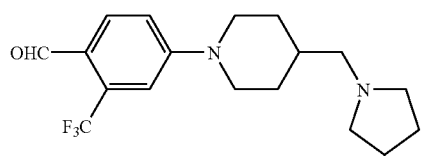

4-(4-Pyrrolidin-1-ylmethyl-piperidin-1-yl)-2-trifluoromethyl-benzaldehyde

Prepared from the product of Example 4 and 4-fluoro-2-trifluoromethyl-benzaldehyde.

Example 66

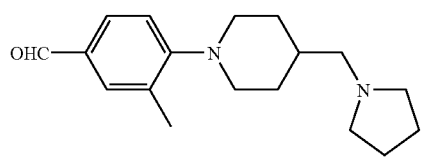

3-Methyl-4-(4-pyrrolidin-1-ylmethyl-piperidin-1-yl)-benzaldehyde

Prepared from the product of Example 4 and 4-fluoro-3-methyl-benzaldehyde.

Example 67

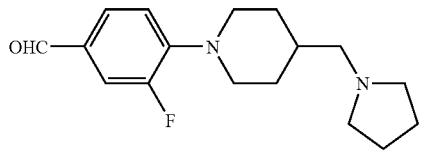

3-Fluoro-4-(4-pyrrolidin-1-ylmethyl-piperidin-1-yl)-benzaldehyde

Prepared from the product of Example 4 and 3,4-difluorobenzaldehyde.

The compounds of Example 68 through 81 were prepared according to the procedure of Example 22 from the specified carbonyl compound and amine.

Example 68

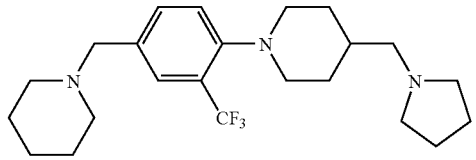

1-[4-(4-Pyrrolidin-1-ylmethyl-piperidin-1-yl)-3-trifluoromethyl-benzyl]-piperidine Prepared from the product of Example 63 and piperidine.
$^1$H NMR (400 MHz, CDCl$_3$): 7.43 (d, J=1.9 Hz, 1H), 7.35 (dd, J=8.2, 1.6 Hz, 1H), 7.17 (d, J=8.4 Hz, 1H), 3.34 (s, 2H), 2.97 (d, J=11.5 Hz, 2H), 2.59 (tt, J=11.3, 2.0 Hz, 2H), 2.48-2.40 (m, 4H), 2.33-2.22 (m, 6H), 1.77-1.66 (m, 6H), 1.55-1.43 (m, 5H), 1.39-1.26 (m, 4H).

Example 69

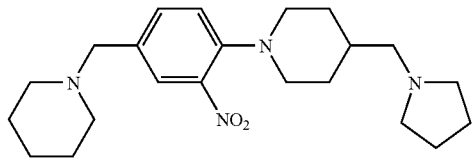

1-(2-Nitro-4-pyrrolidin-1-ylmethyl-phenyl)-4-pyrrolidin-1-ylmethyl-piperidine

Prepared from the product of Example 64 and piperidine.
$^1$H NMR (400 MHz, CDCl$_3$): 7.68 (d, J=2.0, 1H), 7.4 (dd, J=8.4, 2.2 Hz, 1H), 7.06 (d, 8.4 Hz, 1H), 3.40 (s, 2H), 3.26 (d, J=12.3 Hz, 2H), 2.79 (tt, J=11.9, 2.2 Hz, 2H), 2.54-2.44 (m, 4H), 2.42-2.26 (m, 6H), 1.88-1.74 (m, 6H), 1.6-1.5 (m, 5H), 1.48-1.36 (m, 4H).

Example 70

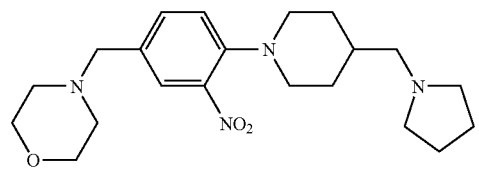

4-[3-Nitro-4-(4-pyrrolidin-1-ylmethyl-piperidin-1-yl)-benzyl]-morpholine

Prepared from the product of Example 64 and morpholine.
$^1$H NMR (400 MHz, CDCl$_3$): 7.71 (d, J=2.0 Hz, 1H), 7.74 (dd, J=8.4, 2.2 Hz, 1H), 7.06 (d, J=8.6, 1H), 3.69 (t, J=4.5 Hz, 4H), 3.43 (s, 2H), 3.26 (d, J=12.3, 2H), 2.79 (tt, J=12.0, 2.1 Hz, 2H), 2.54-2.45 (m, 4H), 2.45-2.39 (m, 4H), 2.39-2.32 (m, 2H), 1.88-1.72 (m, 6H), 1.68-1.34 (m, 1H), 1.48-1.34 (m, 2H).

Example 71

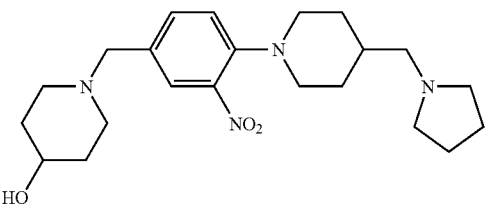

1-[3-Nitro-4-(4-pyrrolidin-1-ylmethyl-piperidin-1-yl)-benzyl]-piperidin-4-ol

Prepared from the product of Example 64 and 4-hydroxypiperidine.
$^1$H NMR (400 MHz, CDCl$_3$): 7.69 (d, J=2.0 Hz, 1H), 7.40 (dd, J=8.4, 2.1 Hz, 1H), 7.07 (d, J=8.4 Hz, 1H), 3.70 (m, 1H), 3.43 (s, 2H), 3.26 (d, J=12.0 Hz, 2H), 2.79 (tt, J=12.0, 2.4 Hz, 2H), 2.73-2.70 (m, 2H), 2.50-2.45 (m, 4H), 2.36 (d, J=6.8 Hz, 2H), 2.14 (t, J=10.4 Hz, 2H), 1.90-1.75 (m, 8H), 1.62-1.54 (m, 4H), 1.46-1.39 (m, 2H).

Example 72

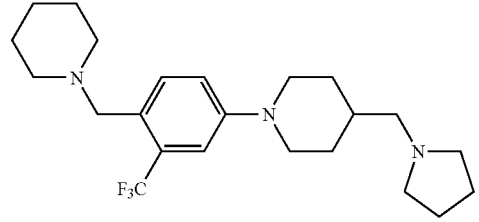

1-[4-(4-Pyrrolidin-1-ylmethyl-piperidin-1-yl)-2-trifluoromethyl-benzyl]-piperidine Prepared from the product of Example 65 and 4-hydroxypiperidine.
$^1$H NMR (400 MHz, CDCl$_3$): 7.60 (d, J=8.6 Hz, 1H), 7.13 (d, J=2.6 Hz, 1H), 7.04 (dd, J=8.6, 2.5 Hz, 1H), 3.68 (d, J=12.3 Hz, 2H), 3.66 (s, 2H), 2.70 (tt, J=12.2, 2.5 Hz, 2H), 2.5-2.48 (m, 4H), 2.4-2.3 (m, 6H), 1.91 (d, J=1.1, 2H), 1.85-1.70 (m, 4H), 1.70-1.50 (m, 5H), 1.50-1.20 (m, 4H).

Example 73

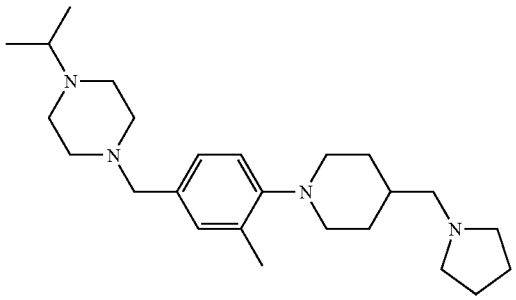

1-Isopropyl-4-[3-methyl-4-(4-pyrrolidin-1-ylmethyl-piperidin-1-yl)-benzyl]-piperazine Prepared from the product of Example 66 and 1-isopropylpiperazine.

¹H NMR (400 MHz, CDCl₃): 7.10 (d, J=1.6 Hz, 1H), 7.06 (dd, J=8.0, 1.9 Hz, 1H), 6.93 (d, J=8.0 Hz, 1H), 3.42 (s, 2H), 3.10 (d, J=9.1 Hz, 2H), 2.7-2.2 (m, 15H), 2.1-1.7 (m, 11H), 1.66-1.53 (m, 1H), 1.5-1.3 (m, 2H), 1.04 (d, J=6.5 Hz, 6H).

Example 74

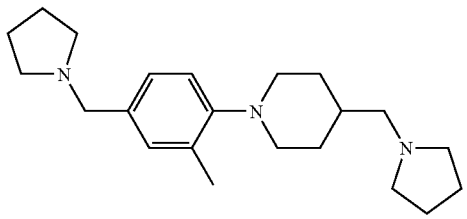

1-(2-Methyl-4-pyrrolidin-1-ylmethyl-phenyl)-4-pyrrolidin-1-ylmethyl-pyrrolidine

Prepared from the product of Example 66 and pyrrolidine.

¹H NMR (400 MHz, CDCl₃): 7.13 (d, J=2.0 Hz, 1H), 7.07 (dd, J=8.2, 2.0 Hz, 1H), 6.93 (d, J=8.2 Hz, 1H), 3.52 (s, 2H), 3.10 (d, J=12.1 Hz, 2H), 2.59 (tt, J=12.1, 2.2 Hz, 2H), 2.54-2.44 (m, 8H), 2.41-2.37 (m, 2H), 2.26 (s, 3H), 1.89-1-81 (m, 2H), 1.81-1.72 (m, 8H), 1.65-1.52 (m, 1H), 1.45-1.31 (m, 2H).

Example 75

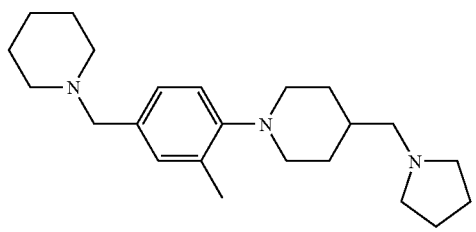

1-[3-Methyl-4-(4-pyrrolidin-1-ylmethyl-piperidin-1-yl)-benzyl]-pyrrolidine

Prepared from the product of Example 66 and piperidine.

¹H NMR (400 MHz, CDCl₃): 7.10 (d, J=1.8 Hz, 1H), 7.06 (dd, J=8.0, 1.8 Hz, 1H), 6.93 (d, J=8.0 Hz, 1H), 3.38 (s, 2H), 3.11 (d, 2H), 2.65-2.54 (m, 2H), 2.54-2.43 (m, 4H), 2.42-2.29 (m, 6H), 2.27 (s, 3H), 1, 90-1.81 (m, 2H), 1.81-1.71 (m, 4H), 1.66-1.50 (m, 5H), 1.47-1.31 (m, 4H).

Example 76

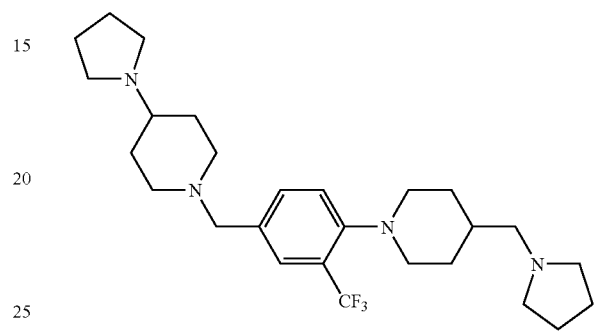

1-{1-[4-(4-Pyrrolidin-1-yl-piperidin-1-ylmethyl)-2-trifluoromethyl-phenyl]-piperidin-4-ylmethyl}-pyrrolidine Prepared from the product of Example 63 and 4-N-pyrrolidinylpiperidine.

¹H NMR (400 MHz, CDCl₃): 7.52 (d, J=1.5 Hz, 1H), 7.44 (d, J=8.2 Hz, 1H), 7.28-7.25 (m, 1H), 3.45 (s, 2H), 3.05 (d, J=11.4 Hz, 2H), 2.84 (d, J=11.7 Hz, 2H), 2.68 (t, J=11.3 Hz, 2H), 2.63-2.44 (m, 8H), 2.38 (d, J=7.0 Hz, 2H), 2.10-1.91 (m, 3H), 1.91-1.70 (m, 12H), 1.49-1.33 (m, 2H).

Example 77

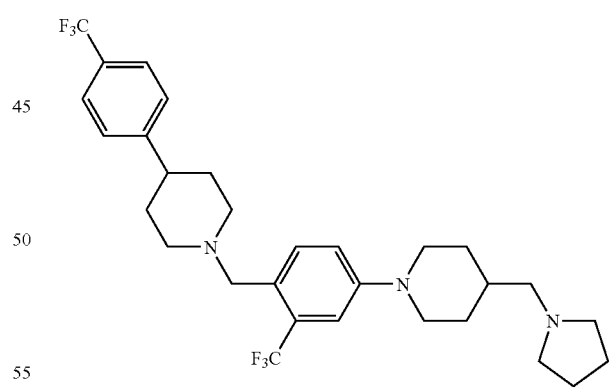

1-(1-{3-Trifluoromethyl-4-[4-(4-trifluoromethyl-phenyl)-piperidin-1-ylmethyl]-phenyl}-piperidin-4-ylmethyl)-pyrrolidine Prepared from the product of Example 65 and 4-(4-trifluouromethylphenyl)-piperidine.

¹H NMR (500 MHz, CDCl₃): 7.62 (d, J=8.6 Hz, 1H), 7.54 (d, J=8.0 Hz, 2H), 7.34 (d, J=8.2 Hz, 2H), 7.14 (d, J=2.5 Hz, 1H), 7.01 (dd, J=8.1, 2.5 Hz, 1H), 3.70 (d, J=12.3 Hz, 2H), 3.58 (s, 2H), 2.98 (d, J=11.7 Hz, 2H), 2.88-2.34 (m, 8H), 2.31-1.56 (m, 13H), 1.52-1.05 (m, 3H).

Example 78

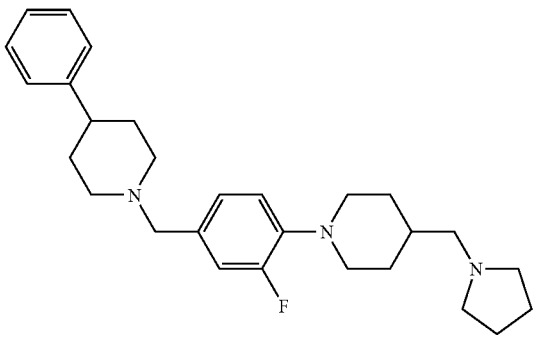

1-{1-[2-Fluoro-4-(4-phenyl-piperidin-1-ylmethyl)-phenyl]-piperidin-4-ylmethyl}-pyrrolidine Prepared from the product of Example 67 and 4-phenylpiperidine.

$^1$H NMR (500 MHz, CDCl$_3$): 7.37-7.16 (m, 5H), 7.12-6.87 (m, 3H), 3.53-3.41 (m, 4H), 3.01 (d, J=11.5 Hz, 2H), 2.67 (t, J=11.5, 9.9 Hz, 2H), 2.58-2.45 (m, 5H), 2.40 (d, J=7.1, 2H), 2.14-2.01 (m, 2H), 1.97-1.87 (m, 2H), 1.86-1.73 (m, 8H), 1.69-1.56 (m, 1H), 1.54-1.41 (m, 2H).

Example 79

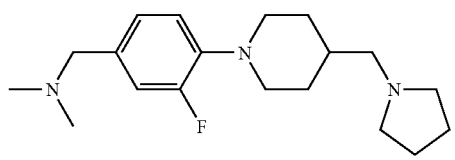

[3-Fluoro-4-(4-pyrrolidin-1-ylmethyl-piperidin-1-yl)-benzyl]-dimethyl-amine

Prepared from the product of Example 67 and dimethylamine hydrochloride.

$^1$H NMR (500 MHz, CDCl$_3$): 7.00-6.93 (m, 2H), 6.90-6.87 (m, 1H), 3.46-3.40 (m, 2H), 3.33 (s, 2H), 2.67-2.59 (m, 2H), 2.57-2.54 (m, 4H), 2.38 (d, J=7.1 Hz, 2H), 2.21 (s, 6H), 1.91-1.84 (m, 2H), 1.81-1.75 (m, 4H), 1.66-1.55 (m, 1H), 1.49-1.38 (m, 2H).

Example 80

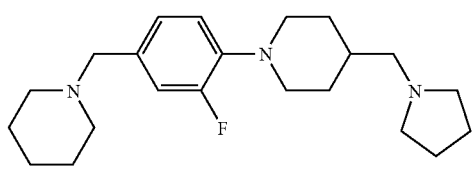

1-[3-Fluoro-4-(4-pyrrolidin-1-ylmethyl-piperidin-1-yl)-benzyl]-piperidine

Prepared from the product of Example 67 and piperidine.

$^1$H NMR (500 MHz, CDCl$_3$): 6.94-6.87 (m, 2H), 6.80 (t, J=8.6, 1H), 3.35 (d, J=12.0 Hz, 2H), 3.30 (s, 2H), 2.57-2.43 (m, 2H), 2.43-2.27 (m, 11H), 1.73-1.70 (m, 6H), 1.51-1.34 (m, 8H).

Example 81

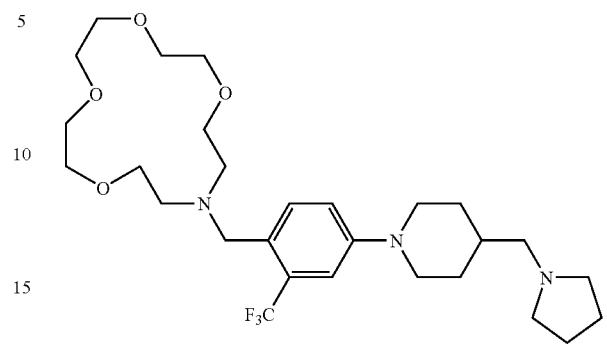

13-[4-(4-pyrrolidin-1-ylmethyl-piperidin-1-yl)-2-trifluoromethyl-benzyl]-1,4,7,10-tetraoxa-13-aza-cyclopentadecane Ditrifluoromethanesulfonate Prepared from the product of Example 65 and 1,4,7,10-tetraoxa-13-aza-cyclopentadecane. The crude material was purified by HPLC (Column: Phenomenex, Synergi Max-RP C-12; 4 micron particle size; 100 mm×21.2 mm (ID) mm. Gradient System: 10% water: acetonitrile to 99% water: acetonitrile containing 0.05% TFA over 0-19 minutes) to provide the target compound as the ditrifluoromethanesulfonate salt.

$^1$H NMR (500 MHz, CD$_3$OD): 7.68 (d, J=8.7 Hz, 1H), 7.29 (d, J=2.6 Hz, 1H), 7.26 (dd, J=8.7, 2.6 Hz, 1H), 3.95-2.92 (m, 31H), 2.17-1.93 (m, 8H), 1.45-1.40 (m, 2H).

Example 82

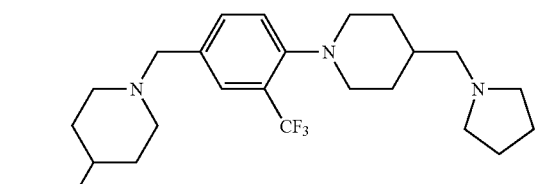

{1-[4-(4-Pyrrolidin-1-ylmethyl-piperidin-1-yl)-3-trifluoromethyl-benzyl]-piperidin-4-yl}-methanol Prepared from the product of Example 63 and 4-hydroxymethylpiperidine.

$^1$H NMR (500 MHz, CDCl$_3$): 7.78-7.14 (m, 3H), 4.30-4.11 (m, 1H), 3.52-3.44 (m, 2H), 3.15-2.49 (m, 7H), 2.06-1.60 (m, 11H), 1.56-0.75 (m, 12H).

Biological Methods

In Vitro

Transfection of Cells with Human Histamine Receptor

A 10 cm tissue culture dish with a confluent monolayer of SK-N-MC cells was split two days prior to transfection. Using sterile technique the media was removed and the cells were detached from the dish by the addition of trypsin. One fifth of the cells were then placed onto a new 10 cm dish. Cells were grown in a 37° C. incubator with 5% CO$_2$ in Minimal Essential Media Eagle with 10% Fetal Bovine Serum. After two days cells were approximately 80% confluent. These were removed from the dish with trypsin and pelleted in a clinical centrifuge. The pellet was then re-suspended in 400 µL complete media and transferred to an electroporation cuvette with a 0.4 cm gap between the electrodes. One microgram of supercoiled $H_3$ receptor cDNA was added to the cells and mixed. The voltage for the electroporation was set at 0.25 kV, the capacitance was set at 960 µF. After electroporation the cells were diluted into 10 mL complete media and plated onto four 10 cm dishes. Because of the variability in the efficiency of electroporation, four different concentrations of cells were plated. The ratios used were; 1:20, 1:10, 1:5, with the remainder of the cells being added to the fourth dish. The cells were allowed to recover for 24 h before adding the selection media (complete media with 600 µg/mL G418). After 10 days dishes were analyzed for surviving colonies of cells. Dishes with well-isolated colonies were used. Cells from individual colonies were isolated and tested. SK-N-MC cells were used because they give efficient coupling for inhibition of adenylate cyclase. The clones that gave the most robust inhibition of adenylate cyclase in response to histamine were used for further study.

{$^3$H}-N-methylhistamine Binding

Cell pellets from histamine $H_3$ receptor-expressing SK-N-MC cells were homogenized in 20 mM Tris HCl/0.5 mM EDTA. Supernatants from an 800 g spin were collected, recentrifuged at 30,000 g for 30 min. Pellets were re-homogenized in 50 mM Tris/5 mM EDTA (pH 7.4). Membranes were incubated with 0.8 nM {$^3$H}-N-methylhistamine plus/minus test compounds for 45 min at 25° C. and harvested by rapid filtration over GF/C glass fiber filters (pretreated with 0.3% polyethylenimine) followed by four washes with ice-cold buffer. Filters were dried, added to 4 mL scintillation cocktail and then counted on a liquid scintillation counter. Non-specific binding was defined with 10 µM histamine. The $pK_i$ values were calculated based on a $K_d$ of 800 pM and a ligand concentration ({L}) of 800 pM according to the formula:

$$K_i = (IC_{50})/(1+({L}/(K_d)))$$

$K_i$ values for exemplary compounds of the invention are listed in the below:

| EX | $K_i$ (nM) |
|---|---|
| 22 | 4500 |
| 23 | 0.9 |
| 24 | 23 |
| 25 | 0.8 |
| 26 | 1.7 |
| 27 | 1.4 |
| 28 | 0.8 |
| 29 | 2 |
| 30 | 1.0 |
| 31 | 2.0 |
| 32 | 9.0 |
| 33 | 20 |
| 34 | 6.0 |
| 35 | 10 |
| 36 | 6.0 |
| 37 | 2.0 |
| 38 | 5.0 |
| 39 | 6.0 |
| 40 | 4.0 |
| 41 | 12 |
| 42 | 5.0 |
| 43 | 4800 |

-continued

| EX | $K_i$ (nM) |
|---|---|
| 44 | 5.0 |
| 45 | 2.0 |
| 46 | 28 |
| 47 | 5.8 |
| 48 | 1000 |
| 49 | 14 |
| 50 | 272 |
| 51 | 17 |
| 52 | 5.5 |
| 53 | 2.7 |
| 54 | 8.4 |
| 55 | 8.0 |
| 56 | 3.0 |
| 57 | 2.5 |
| 58 | 0.6 |
| 59 | 48 |
| 60 | 1.1 |
| 61 | 0.8 |
| 62 | 1.3 |
| 68 | 14 |
| 69 | 2 |
| 70 | 36 |
| 71 | 5 |
| 72 | 8 |
| 73 | 16 |
| 74 | 1 |
| 75 | 6 |
| 76 | 9 |
| 77 | 160 |
| 78 | 7 |
| 79 | 4 |
| 80 | 4 |
| 81 | 34 |
| 82 | 170 |

F. Other Embodiments

The features and advantages of the invention will be apparent to one of ordinary skill in view of the discussion, examples, embodiments, and claims relating to the invention. The invention also contemplates variations and adaptations, based on the disclosure herein concerning the key features and advantages of the invention, and within the abilities of one of ordinary skill.

What is claimed is:
1. A compound of formula (I):

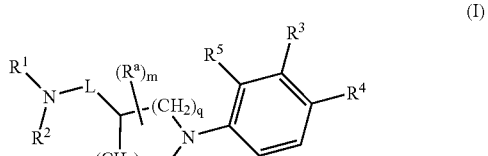

wherein

L is a direct bond, or an optionally $C_{1-4}$alkyl substituted radical selected from the group consisting of $C_{1-4}$alkylene or $C_{3-4}$alkenylene wherein $NR^1R^2$ is attached to an $sp^3$ hybridized carbon, $C_{3-4}$alkynylene wherein $NR^1R^2$ is attached to an $sp^3$ hybridized carbon, $C_{2-4}$alkylidene wherein $NR^1R^2$ is attached to an $sp^3$ hybridized carbon, aryloxy wherein $NR^1R^2$ is not attached to the oxygen, arylthio wherein $NR^1R^2$ is not attached to the sulfur, $C_{2-4}$alkoxy wherein $NR^1R^2$ is not attached to the oxygen or a carbon attached to the oxygen, $C_{2-4}$alkylthio wherein NR$^1$R$^2$ is not attached to the sulfur or a carbon attached to the sulfur, and —C$_{2-3}$alkyl-X—C$_{1-2}$alkyl- wherein X is O, S or NH and wherein NR$^1$R$^2$ is not attached to a carbon attached to X;

p is 0, 1 or 2;

q is 1 or 2; provided that 2≦p+q≦4;

R$^1$ and R$^2$ taken together with the nitrogen to which they are attached form piperidinyl or pyrrolidinyl;

wherein R$^1$ and R$^2$ are optionally and independently substituted with 1-3 substituents selected from the group consisting of tert-butyloxycarbonyl, hydroxy, halo, nitro, amino, cyano, carboxamide, C$_{1-6}$ alkyl, C$_{1-6}$ acyl, 5-9-membered heterocyclyl, —N(C$_{1-6}$ alkyl)(5-9 membered heterocyclyl), —NH(5-9 membered heterocyclyl), —O(5-9 membered heterocyclyl), (5-9 membered heterocyclyl)C$_{1-3}$ alkylene, C$_{1-2}$-hydroxyalkylene, C$_{1-6}$ alkoxy, (C$_{3-6}$ cycloalkyl)-O—, phenyl, (phenyl)C$_{1-3}$ alkylene, and (phenyl)C$_{1-3}$ alkylene-O—; and wherein each of the preceding substituents of R$^1$ and R$^2$ may optionally have between 1 and 3 substituents independently selected from the group consisting of trifluoromethyl, halo, nitro, cyano, hydroxy, and C$_{1-3}$ alkyl;

one of R$^3$, R$^4$ and R$^5$ is G and the other two independently are hydrogen, fluoro, chloro, bromo, nitro, trifluoromethyl, methyl, or C$_{1-3}$ alkoxy;

G is L$^2$Q;

L$^2$ is unbranched —(CH$_2$)$_n$— wherein n is an integer from 1 to 7;

Q is a N-linked heterocyclyl which is piperidinyl or pyrrolidinyl;

wherein Q is optionally substituted with 1-3 substituents selected (in addition to the preceding paragraph) from the group consisting of tert-butyloxycarbonyl, hydroxy, halo, nitro, amino, cyano, carboxamide, C$_{1-6}$ alkyl, C$_{1-6}$ acyl, 5-9-membered heterocyclyl, —N(C$_{1-6}$ alkyl)(5-9 membered heterocyclyl), —NH(5-9 membered heterocyclyl), —O(5-9 membered heterocyclyl), (5-9 membered heterocyclyl)C$_{1-3}$ alkylene, C$_{1-2}$-hydroxyalkylene, C$_{1-6}$ alkoxy, (C$_{3-6}$ cycloalkyl)-O—, phenyl, (phenyl)C$_{1-3}$ alkylene, and (phenyl)C$_{1-3}$ alkylene-O—; and where said substituent groups of Q may optionally have between 1 and 3 substituents independently selected from trifluoromethyl, halo, nitro, cyano, hydroxy, and C$_{1-3}$ alkyl;

R$^a$ are independently C$_{1-3}$ alkyl, triflouromethyl;

m is 0, 1, 2 or 3; and wherein each of the above alkyl, alkylene, alkenyl, heterocyclyl, cycloalkyl, carbocyclyl, and aryl groups may each be independently and optionally substituted with between 1 and 3 substituents independently selected from methoxy, halo, amino, nitro, hydroxy, and C$_{1-3}$ alkyl;

or a pharmaceutically acceptable acid addition, alkali metal or alkaline earth metal salt thereof.

2. A compound of claim 1, wherein NR$^1$R$^2$ taken together is optionally substituted with between 1 and 3 substituents selected from hydroxy, halo, carboxamide, C$_{1-6}$ alkyl, C$_{1-6}$ acyl, 5-9 membered heterocyclyl, —N(C$_{1-6}$ alkyl)(5-9 membered heterocyclyl), —NH(5-9 membered heterocyclyl), —O(5-9 membered heterocyclyl), (5-9 membered heterocyclyl)C$_{1-3}$ alkylene, C$_{1-2}$-hydroxyalkylene, C$_{1-6}$ alkoxy, (C$_{3-6}$ cycloalkyl)-O—, phenyl, (phenyl)C$_{1-3}$ alkylene, and (phenyl)C$_{1-3}$ alkylene-O— where each of above heterocyclyl, phenyl, and alkyl groups may be optionally substituted with from 1 to 3 substituents independently selected from trifluoromethyl, halo, nitro, cyano, hydroxy, and C$_{1-3}$ alkyl.

3. A compound of claim 1, wherein NR$^1$R$^2$ taken together is substituted with a substituent selected from the group consisting of pyridyl, pyrimidyl, furyl, thiofuryl, imidazolyl, (imidazolyl)C$_{1-6}$ alkylene, oxazolyl, thiazolyl, 2,3-dihydro-indolyl, benzimidazolyl, 2-oxobenzimidazolyl, (tetrazolyl)C$_{1-6}$ alkylene, tetrazolyl, (triazolyl)C$_{1-6}$ alkylene, triazolyl, (pyrrolyl)C$_{1-6}$ alkylene, pyrrolidinyl, and pyrrolyl.

4. A compound of claim 1, wherein one of R$^3$ and R$^4$ is G.

5. A compound of claim 1, wherein R$^4$ is G.

6. A compound of claim 4, wherein R$^3$ is G.

7. A compound of claim 1, wherein q is 2 and p is 1.

8. A compound of claim 1, wherein q is 1 and p is 1.

9. A compound of claim 1, wherein q is 2 and p is 2.

10. A compound of claim 1, wherein L is —CH$_2$—.

11. A compound of claim 1, wherein L is a direct bond.

12. A compound of claim 1, wherein L is —CH$_2$CH$_2$—.

13. A compound of claim 1, wherein L$^2$ is —CH$_2$—.

14. A compound of claim 1, wherein Q is optionally substituted with between 1 and 3 substituents selected from hydroxy, halo, carboxamide, C$_{1-6}$ alkyl, C$_{1-6}$ acyl, 5-9 membered or 6-9 membered heterocyclyl, —N(C$_{1-6}$ alkyl)(5-9 membered or 6-9 membered heterocyclyl), —NH(5-9 membered or 6-9 membered heterocyclyl), —O(5-9 or 6-9 membered heterocyclyl), (5-9 membered or 6-9 membered heterocyclyl)C$_{1-3}$ alkylene, C$_{1-2}$-hydroxyalkylene, C$_{1-6}$ alkoxy, (C$_{3-6}$ cycloalkyl)-O—, phenyl, (phenyl)C$_{1-3}$ alkylene, and (phenyl)C$_{1-3}$ alkylene-O— where each of above heterocyclyl, phenyl, and alkyl groups may be optionally substituted with from 1 to 3 substituents independently selected from trifluoromethyl, halo, nitro, cyano, hydroxy, and C$_{1-3}$ alkyl.

15. A compound of claim 14, wherein Q is substituted with a substituent comprising a 5-9 membered heterocyclyl group selected from: pyridyl, pyrimidyl, furyl, thiofuryl, imidazolyl, (imidazolyl)C$_{1-6}$ alkylene, oxazolyl, thiazolyl, 2,3-dihydro-indolyl, benzimidazolyl, 2-oxobenzimidazolyl, (tetrazolyl)C$_{1-6}$ alkylene, tetrazolyl, (triazolyl)C$_{1-6}$ alkylene, triazolyl, (pyrrolyl)C$_{1-6}$ alkylene, pyrrolidinyl, and pyrrolyl.

16. A compound of claim 1, wherein:

R$^1$ and R$^2$ taken together with the nitrogen to which they are attached, form piperidinyl or pyrrolidinyl;

one of R$^3$, R$^4$, and R$^5$ is G and the two remaining are H;

G is L$^2$Q;

L$^2$ is methylene;

Q is a N-linked heterocyclyl which is piperidinyl or pyrrolidinyl;

wherein each of the above alkyl, alkylene, alkenyl, alkenylene, heterocyclyl, and carbocyclyl groups may each be independently and optionally substituted with between 1 and 3 substituents selected from methoxy, halo, amino, nitro, hydroxyl, and C$_{1-3}$ alkyl;

wherein substituents of Q can be further selected from tert-butyloxycarbonyl, hydroxy, halo, nitro, amino, cyano, carboxamide, 5-9-membered heterocyclyl, —NH(6-membered heterocyclyl), —O(6-membered heterocyclyl), C$_2$-hydroxyalkylene, phenyl, benzyl and, where each of above heterocyclyl, phenyl, and alkyl substituent groups of Q may be optionally substituted with trifluoromethyl;

or a pharmaceutically acceptable acceptable acid addition, alkali metal or alkaline earth metal salt thereof.

17. A compound of claim 1, wherein n is 1, p is 1 and q is 2.

18. A compound of claim 1, wherein n is 1, p is 2 and q is 2.

19. A compound of claim 1, wherein Q is piperidinyl or substituted piperidinyl.

20. A compound of claim 1 wherein R$^a$ is hydrogen.

21. A compound of claim 1 selected from the group consisting of
- 1-{1-(4-Pyrrolidin-1-ylmethyl-phenyl)-piperidin-4-ylmethyl}-piperidin-4-ol;
- 1-{1-(4-Pyrrolidin-1-ylmethyl-phenyl)-piperidin-4-ylmethyl}-piperidine;
- 4-Pyrrolidin-1-ylmethyl-1-(3-pyrrolidin-1-ylmethyl-phenyl)-piperidine;
- 1-{3-(4-Pyrrolidin-1-ylmethyl-piperidin-1-yl)-benzyl}-piperidine;
- 1-{4-(4-Pyrrolidin-1-ylmethyl-piperidin-1-yl)-benzyl}-piperidin-4-ol;
- 1-{4-(4-Pyrrolidin-1-ylmethyl-piperidin-1-yl)-benzyl}-piperidine;
- 1'-(4-Piperidin-1-ylmethyl-phenyl)-{1,4'}bipiperidinyl;
- 1-{1-(4-Piperidin-1-ylmethyl-phenyl)-piperidin-4-ylmethyl}-piperidine;
- 4-Pyrrolidin-1-ylmethyl-1-(4-pyrrolidin-1-ylmethyl-phenyl)-piperidine;
- 1-[4-(4-Pyrrolidin-1-ylmethyl-piperidin-1-yl)-3-trifluoromethyl-benzyl]-piperidine;
- 1-(2-Nitro-4-pyrrolidin-1-ylmethyl-phenyl)-4-pyrrolidin-1-ylmethyl-piperidine;
- 1-[3-Nitro-4-(4-pyrrolidin-1-ylmethyl-piperidin-1-yl)-benzyl]-piperidin-4-ol;
- 1-[4-(4-Pyrrolidin-1-ylmethyl-piperidin-1-yl)-2-trifluoromethyl-benzyl]-piperidine;
- 1-(2-Methyl-4-pyrrolidin-1-ylmethyl-phenyl)-4-pyrrolidin-1-ylmethyl-pyrrolidine;
- 1-[3-Methyl-4-(4-pyrrolidin-1-ylmethyl-piperidin-1-yl)-benzyl]-pyrrolidine;
- 1-{[4-(4-Pyrrolidin-1-yl-piperidin-1-ylmethyl)-2-trifluoromethyl-phenyl]-piperidin-4-ylmethyl}-pyrrolidine;
- 1-(1-{3-Trifluoromethyl-4-[4-(4-trifluoromethyl-phenyl)-piperidin-1-ylmethyl]-phenyl}-piperidin-4-ylmethyl)-pyrrolidine;
- 1-{1-[2-Fluoro-4-(4-phenyl-piperidin-1-ylmethyl)-phenyl]-piperidin-4-ylmethyl}-pyrrolidine;
- 1-[3-Fluoro-4-(4-pyrrolidin-1-ylmethyl-piperidin-1-yl)-benzyl]-piperidine; and
- {1-[4-(4-Pyrrolidin-1-ylmethyl-piperidin-1-yl)-3-trifluoromethyl-benzyl]-piperidin-4-yl}-methanol.

22. A pharmaceutical composition, comprising a compound of claim 1 and a pharmaceutically-acceptable excipient.

* * * * *